US011912970B2

(12) United States Patent
Zhang et al.

(10) Patent No.: US 11,912,970 B2
(45) Date of Patent: Feb. 27, 2024

(54) UNIVERSAL MICROFLUIDIC CULTURE SYSTEM TO ANALYZE AND CONTROL CELL DYNAMICS

(71) Applicant: The University of Chicago, Chicago, IL (US)

(72) Inventors: Ce Zhang, Chicago, IL (US); Savas Tay, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 174 days.

(21) Appl. No.: 16/614,174

(22) PCT Filed: May 15, 2018

(86) PCT No.: PCT/US2018/032727
§ 371 (c)(1),
(2) Date: Nov. 15, 2019

(87) PCT Pub. No.: WO2018/213282
PCT Pub. Date: Nov. 22, 2018

(65) Prior Publication Data
US 2022/0041966 A1 Feb. 10, 2022

Related U.S. Application Data

(60) Provisional application No. 62/506,362, filed on May 15, 2017.

(51) Int. Cl.
*C12M 3/06* (2006.01)
*C12M 1/00* (2006.01)
*C12M 1/02* (2006.01)
*C12M 1/26* (2006.01)
*C12M 1/34* (2006.01)
*C12M 1/36* (2006.01)

(52) U.S. Cl.
CPC ............ *C12M 23/16* (2013.01); *C12M 23/34* (2013.01); *C12M 23/40* (2013.01); *C12M 27/00* (2013.01); *C12M 29/00* (2013.01); *C12M 33/00* (2013.01); *C12M 41/32* (2013.01); *C12M 41/48* (2013.01)

(58) Field of Classification Search
CPC ...... C12M 23/16; C12M 23/34; C12M 23/40; C12M 27/00; C12M 29/00; C12M 33/00; C12M 41/32; C12M 41/48
USPC ....................................................... 435/288.7
See application file for complete search history.

(56) References Cited

U.S. PATENT DOCUMENTS

| | | | |
|---|---|---|---|
| 8,936,764 B2 | 1/2015 | Enzelberger et al. | |
| 9,381,512 B2 | 7/2016 | Cohen et al. | |
| 2003/0196695 A1 | 10/2003 | O'Connor | |
| 2005/0019792 A1* | 1/2005 | McBride ........... | B01L 3/502715 435/6.19 |

(Continued)

OTHER PUBLICATIONS

Basak & Taylor, "Identification of Self-Replicating Multipotent Progenitors in the Embryonic Nervous System by High Notch activity and Hes5 Expression," *European Journal of Neuroscience*, 25(4): 1006-1022, 2007.

(Continued)

*Primary Examiner* — Michael L Hobbs
*Assistant Examiner* — Lenora A Abel
(74) *Attorney, Agent, or Firm* — Norton Rose Fulbright US LLP

(57) ABSTRACT

Microfluidic devices, systems, and methods.

26 Claims, 76 Drawing Sheets

(56) References Cited

U.S. PATENT DOCUMENTS

| | | | |
|---|---|---|---|
| 2007/0275455 A1* | 11/2007 | Hung | F16K 99/0059 156/228 |
| 2014/0318633 A1 | 10/2014 | Facer et al. | |
| 2017/0007998 A1 | 1/2017 | Fraden et al. | |

OTHER PUBLICATIONS

Cao, et al., "Amicrofluidic Device for Epigenomic Profiling Using 100 Cells," *Nature Methods*, 12(10), 959-962, 2015.

Dorshkind, "Not a Split Decision for Human Hematopoiesis," *Nature Immunology*, 11, 569-570, 2010.

Ghasemi-Dehkordi, et al., Effects of Feeder Layers, Culture Media, Conditional Media, Growth Factors, and Passages Number on Stem Cell Optimization, *PNAS India Sect. B—Biol. Sci.* 85(3), 711-717, 2015.

Giachino, et al., Isolation and Manipulation of Mammalian Neural Stem Cells in Vitro. *Methods in Molecular Biology*, 482, 143-158, 2009.

Gomez-Sjoberg, et al., "Versatile, fully automated, microfluidic cell culture system," *Analytical Chemistry*, 79, 8557-8563, 2007.

International Search Report and Written Opinion Issued in Corresponding PCT Application No. PCT/US2018/032727, dated Aug. 13, 2018.

Jeong, et al., "Wireless Optofluidic Systems for Programmable in Vivo Pharmacology and Optogenetics," *Cell*, 162, 662-674, 2015.

Judge, et al., "Sequence-Dependent Stimulation of the Mammalian Innate Immune Response by Synthetic siRNA," *Nature Biotechnology*, 23, 457-462, 2005.

Kellogg & Tay, "Noise Facilitates Transcriptional Control Under Dynamic Inputs," *Cell*, 160, 381-392, 2015.

Klein, et al., "Droplet Barcoding for Single-Cell Transcriptomics Applied to Embryonic Stem Cells," *Cell*, 161, 1187-1201, 2015.

Kolch, et al., "The Dynamic Control of Signal Transduction Networks in Cancer Cells," *Nature Reviews Cancer*, 15, 515-527, 2015.

Lecault, et al., "High-Throughput Analysis of Single Hematopoietic Stem Cell Proliferation in Microfluidic Cell Culture Arrays," *Nature Methods*, 8, 581-U93, 2011.

Ludwig, et al., "Derivation of Human Embryonic Stem Cells in Defined Conditions," *Nature Biotechnology*, 24, 185-187, 2006.

Luni, et al., "High-Efficiency Cellular Reprogramming with Microfluidics," *Nature Methods*, 13, 446-452, 2016.

Mehling & Tay, "Microfluidic Cell Culture," *Current Opinion in Biotechnology*, 25, 95-102, 2014.

Mohabbat, et al., "Anti-Tumour Necrosis Factor Treatment of Inflammatory Bowel Disease in Liver Transplant Recipients," *Alimentary Pharmacology and Therapeutics*, 36, 569-574, 2012.

Occhetta, et al., High-Throughput Microfluidic Platform for 3D Cultures of Mesenchymal Stem Cells, Towards Engineering Developmental Processes. *Science Reports*, 5, 10288, 2015.

Ohtsuka, et al., "Roles of the Basic Helix-Loop-Helix Genes Hes1 and Hes5 in Expansion of Neural Stem Cells of the Developing Brain," *Journal of Biological Chemistry*, 276, 30467-30474, 2001.

Otify, et al., "Transdifferentiation of Bone Marrow Mesenchymal Stem Cells into Neural Cells via Cerebrospinal Fluid," *Biomedicine and Biotechnology*, 2, 66-79, 2014.

Sarioglu, et al., "A Microfluidic Device for Label-Free, Physical Capture of Circulating Tumor Cell Clusters," *Nature Methods*, 12, 1-10, 2015.

Tay, et al., "Single-cell Nf-kappaB Dynamics Reveal Digital Activation and Analogue Information Processing," *Nature*, 466, 267-271, 2010.

Unger, et al. "Monolithic Microfabricated Valves and Pumps by Multilayer Soft Lithography," *Science*,. 288, 113-116, 2000.

Wolfe & Ahsan, "Shear Stress During Early Embryonic Stem Cell Differentiation Promotes Hematopoietic and Endothelial Phenotypes," *Biotechnology and Bioengineering*, 110, 1231-1242, 2013.

Xiong, et al., "Selective Neuronal Differentiation of Neural Stem Cells Induced by Nanosecond Microplasma Agitation," *Stem Cell Res.* 12, 387-399, 2014.

Ying, et al., "BMP Induction of Id Proteins Suppresses Differentiation and Sustains Embryonic Stem Cell Self-Renewal in Collaboration With STAT3," *Cell*, 115, 281-292, 2003.

\* cited by examiner

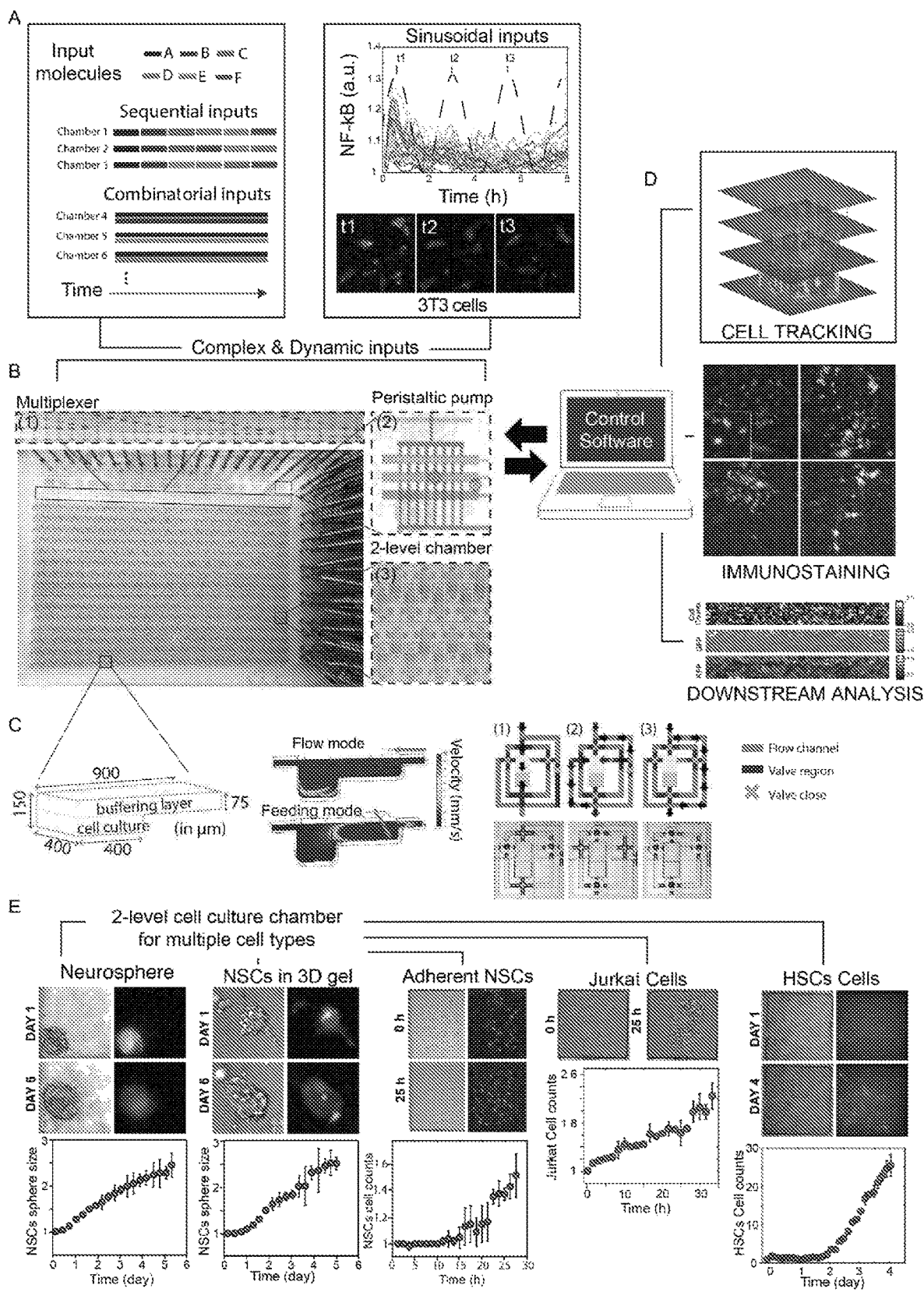
FIG. 1(A-E)

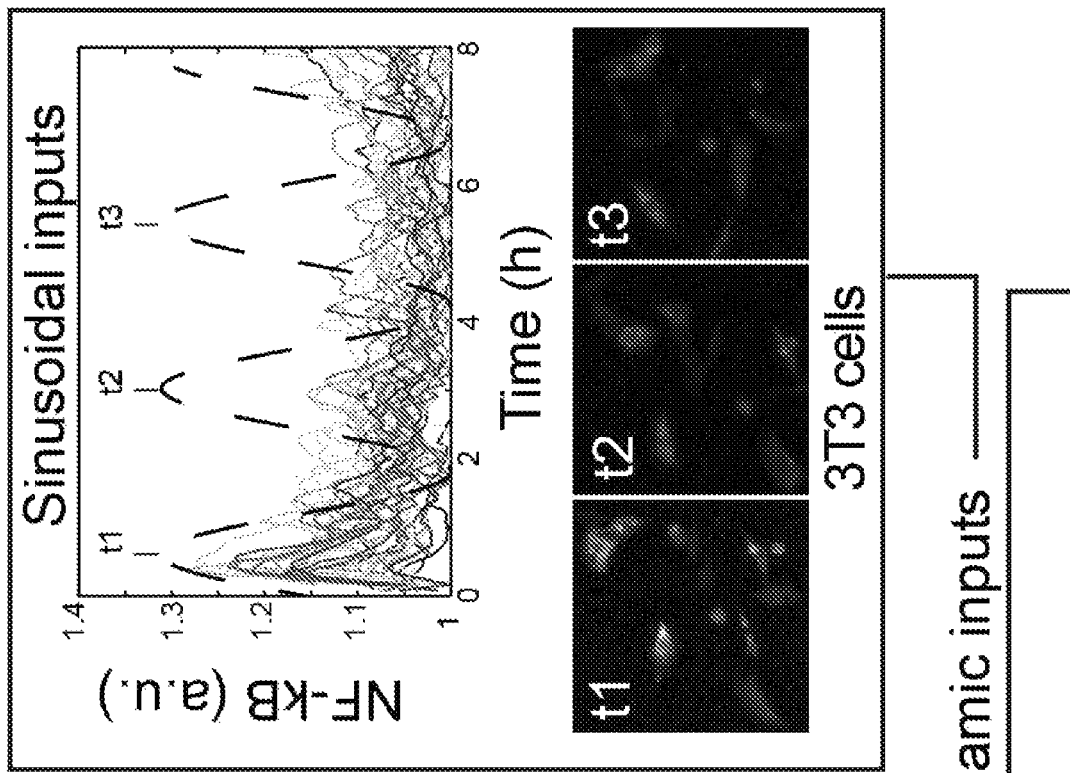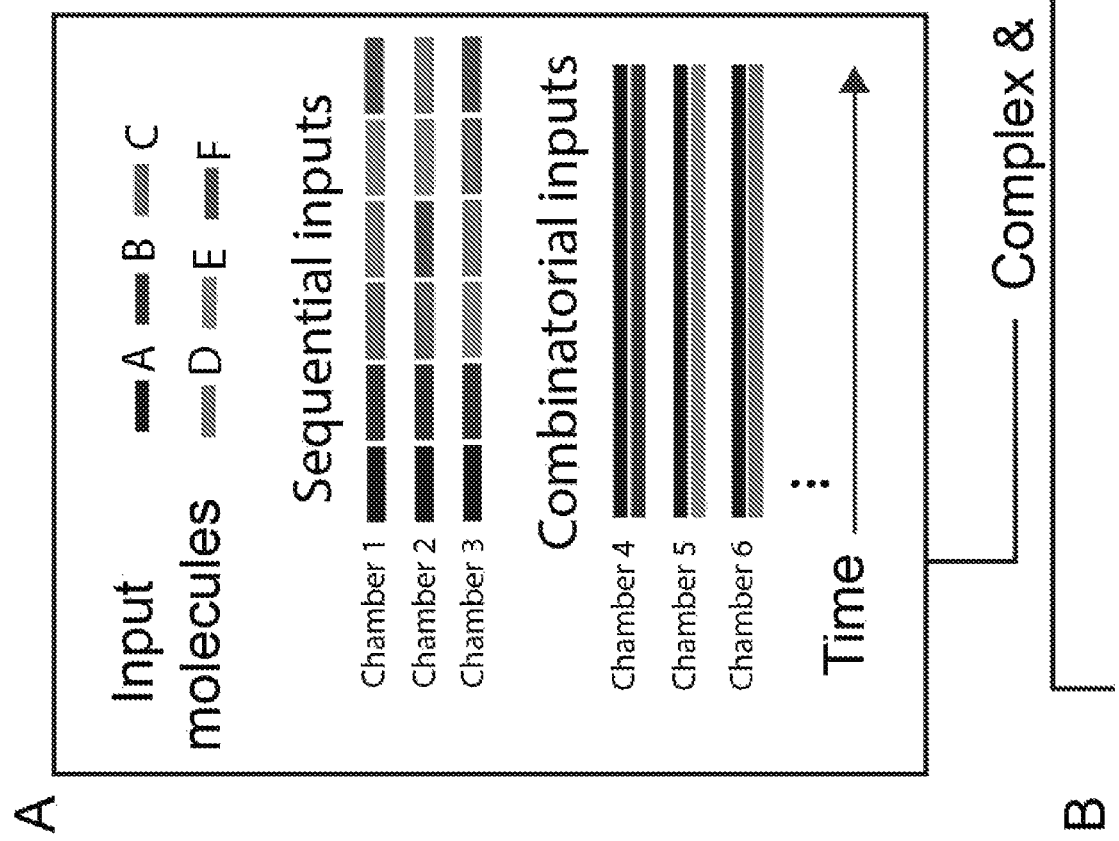
FIG. 1A

Single ligand stimulation

| | Cell no. | Hes-5 |
|---|---|---|
| Jagged | ▼ 26% | — |
| DLL | — | — |
| EGF | ▼ 40% | ▲ 8% |
| PACAP | ▲ 388% | ▼ 19% |
| CXCL | ▲ 162% | ▼ 28% |
| PDGF | ▲ 100% | ▲ 30% |

Combinatorial stimulation

| | Cell no. | Hes-5 |
|---|---|---|
| Jagged | ▲ 27% | ▲ 6% |
| DLL | ▲ 33% | — |
| EGF | ▲ 33% | ▲ 6% |
| PACAP | ▲ 55% | — |
| CXCL | ▲ 26% | — |
| PDGF | ▲ 26% | ▲ 6% |

Sequential stimulation — Cell number

| | d1 | d2 | d3 | d4 | d5 | d6 |
|---|---|---|---|---|---|---|
| Jagged | ▲ 11% | — | ▼ 5% | — | — | — |
| DLL | ▼ 10% | — | ▼ 5% | — | — | — |
| EGF | ▼ 7% | ▲ 9% | ▲ 8% | — | ▲ 11% | ▲ 11% |
| PACAP | ▲ 15% | ▼ 13% | — | ▼ 7% | ▲ 7% | ▼ 6% |
| CXCL | — | — | ▼ 7% | — | ▲ 7% | ▼ 7% |
| PDGF | ▼ 15% | ▲ 8% | — | — | — | — |

Sequential stimulation — Hes-5

| | d1 | d2 | d3 | d4 | d5 | d6 |
|---|---|---|---|---|---|---|
| Jagged | ▼ 5% | ▲ 16% | ▲ 22% | — | — | — |
| DLL | ▲ 8% | ▲ 23% | ▲ 12% | — | — | — |
| EGF | ▼ 13% | ▲ 8% | ▲ 6% | ▲ 12% | ▲ 14% | ▲ 13% |
| PACAP | ▲ 5% | ▲ 9% | ▲ 6% | ▲ 8% | ▲ 14% | ▲ 15% |
| CXCL | ▲ 18% | — | — | ▲ 10% | ▲ 7% | ▲ 10% |
| PDGF | ▲ 27% | — | — | ▲ 7% | ▲ 6% | — |

FIG. 8C-1

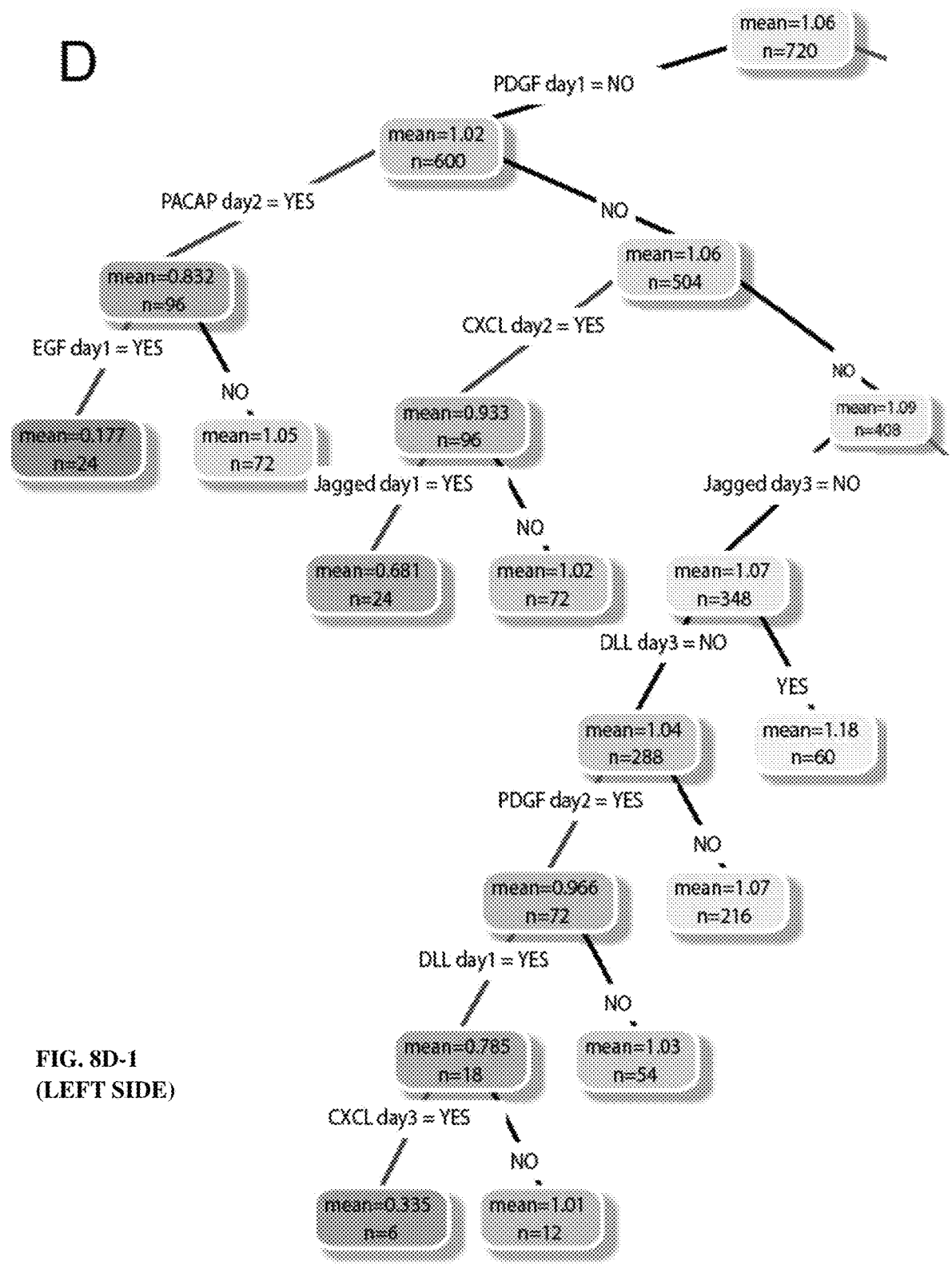
FIG. 8D-1 (LEFT SIDE)

(RIGHT SIDE)

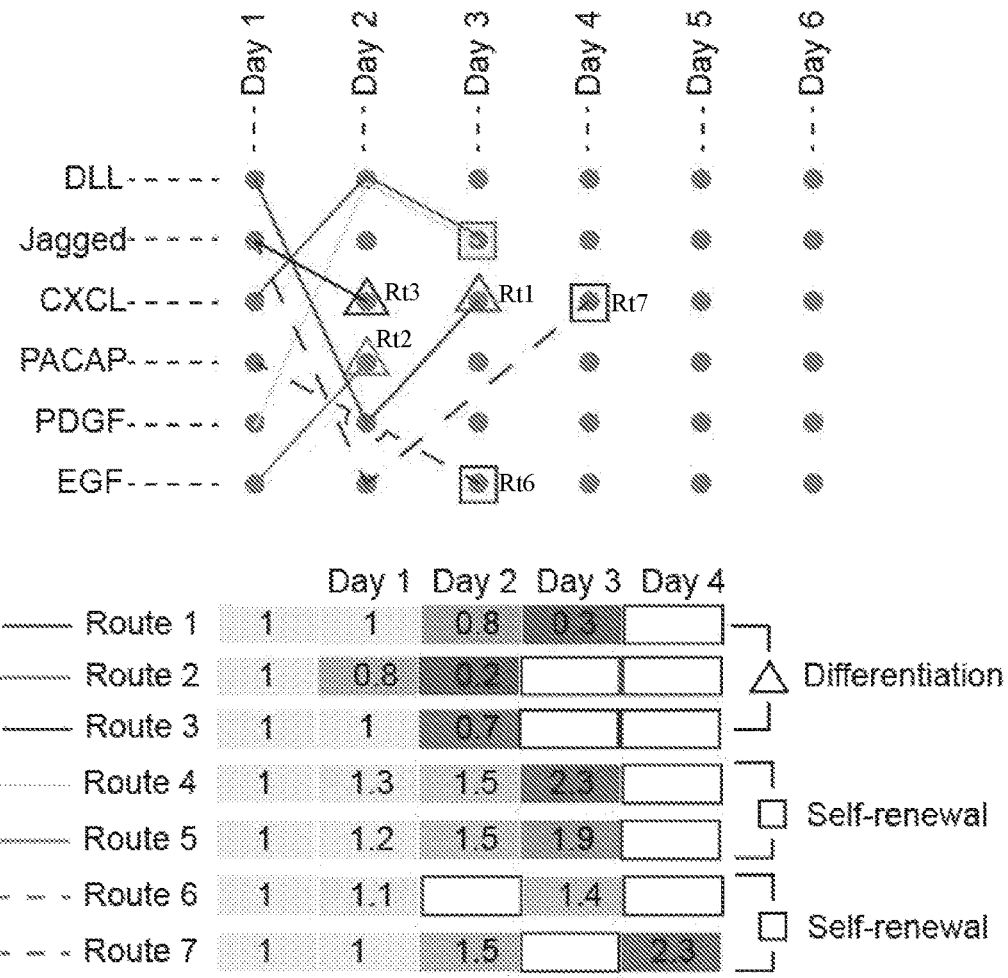

1. PDGF at day 1 ⇒ self-renewal
2. (PDGF at day 1) and (DLL at day 2) and (Jagged at day 3) ⇒ self-renewal
3. (EGF at day 1) and (PACAP at day 2) ⇒ differentiation
4. CXCL at day 1 ⇒ self-renewal
5. PACAP at day 1 ⇒ cell proliferation
6. (PACAP at day 1) and (EGF at day 3) ⇒ cell proliferation
7. (Jagged at day 1) and (EGF at day 2) and (CXCL at day 4) ⇒ cell proliferation
8. DLL at day 1 ⇒ differentiation
9. PACAP ⇒ self-renewal
10. PDGF ⇒ self-renewal
11. PDGF and not DLL and not CXCL ⇒ self-renewal

FIG. 8E

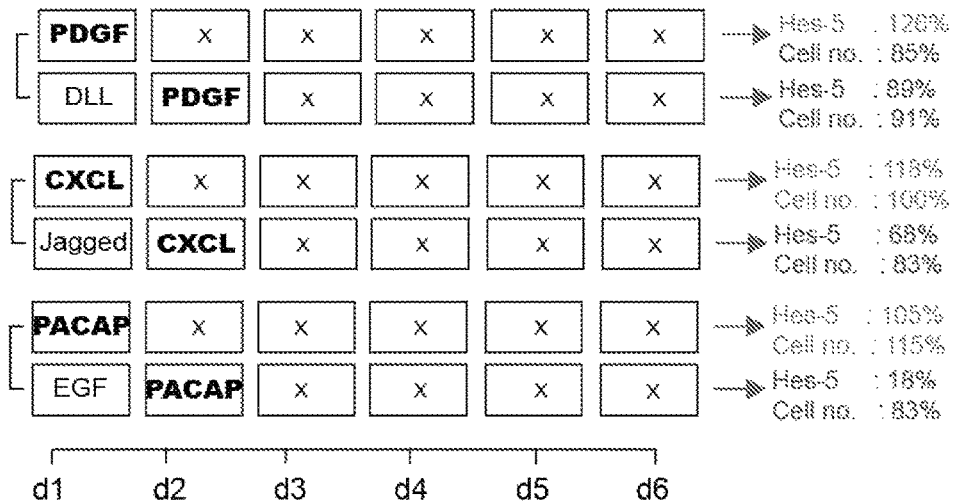
FIG. 9F
FIG. 9F
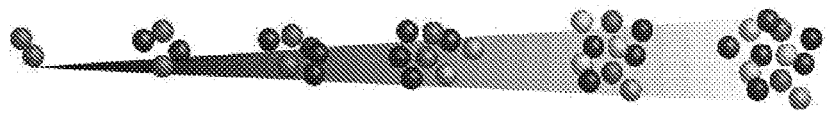
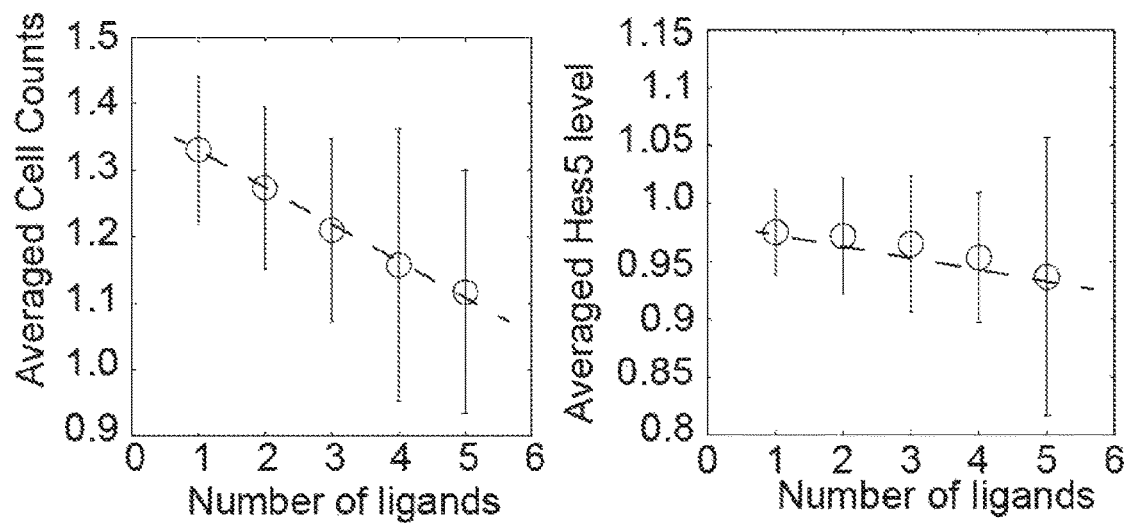
FIG. 9G

H 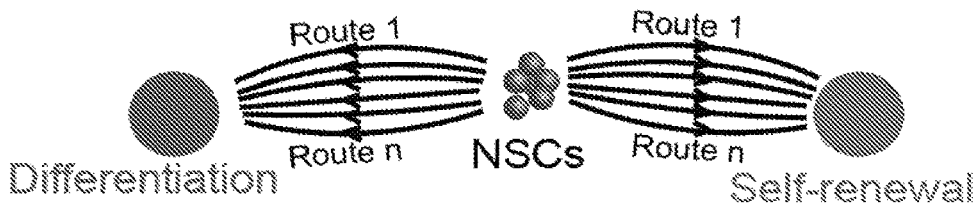

Differentiation

| Combination | Cell no. | Hes-5 |
|---|---|---|
| Jagged + DLL | 68% | 70% |
| Jagged + PACAP + CXCL + PDGF | 70% | 80% |
| EGF + CXCL | 60% | 80% |

Sequential

| | | |
|---|---|---|
| EGF >CXCL >Jagged > PACAP > PDGF > DLL | 14% | 0% |
| EGF > PACAP > CXCL > PDGF > DLL > Jagged | 26% | 0% |
| EGF > PACAP > CXCL > DLL >PDGF > Jagged | 21% | 0% |
| EGF > PACAP > CXCL > Jagged >DLL >PDGF | 6% | 0% |

Self-renewal

| Combination | Cell no. | Hes-5 |
|---|---|---|
| Jagged + EGF + PACAP + PDGF | 150% | 120% |
| Jagged + DLL + EGF + PACAP + CXCL | 140% | 120% |
| Jagged + PACAP + PDGF | 200% | 122% |
| PACAP + PDGF | 200% | 129% |

Sequential

| | | |
|---|---|---|
| PACAP >EGF >Jagged >CXCL >DLL >PDGF | 196% | 102% |
| PDGF >DLL >Jagged >EGF >PACAP >CXCL | 467% | 368% |

FIG. 9H

Combinatorial inputs
J - Jagged; D - DLL; E - EGF; PA - PACAP; C - CXCL; PD - PDGF

| | | | | |
|---|---|---|---|---|
| J+D+E+PA+C+PD | D+PA+C+PD | J+D+PD | J+PA+C | D+PD |
| D+E+PA+C+PD | D+E+C+PD | J+D+C | D+PA+C | J+PD |
| J+D+E+PA+PD | D+E+PA+PD | J+E+PD | D+E+PA | E+PD |
| J+D+E+PA+C | D+E+PA+C | J+C+PD | E+PA+C | PA+PD |
| J+D+E+C+PD | J+PA+C+PD | D+E+C | E+PA+PD | C+PD |
| J+E+PA+C+PD | J+E+C+PD | D+E+PD | PA+C+PD | J+PA |
| J+D+C+C+PD | J+D+C+PD | D+C+PD | J+D | D+PA |
| J+D+E+PD | J+D+E+PD | E+C+PD | J+E | E+PA |
| J+E+PA+PD | J+D+E+C | J+D+PA | J+C | PA+C |
| J+D+PA+PD | J+D+E+PA | J+D+E | D+E | |
| J+E+PA+C | J+D+E+PA | J+PA+PD | D+C | |
| J+D+PA+C | J+E+C | D+PA+PD | E+C | |
| E+PA+C+PD | J+E+PA | | | |

A
Decision tree analysis on NSCs proliferation (combinatorial input)
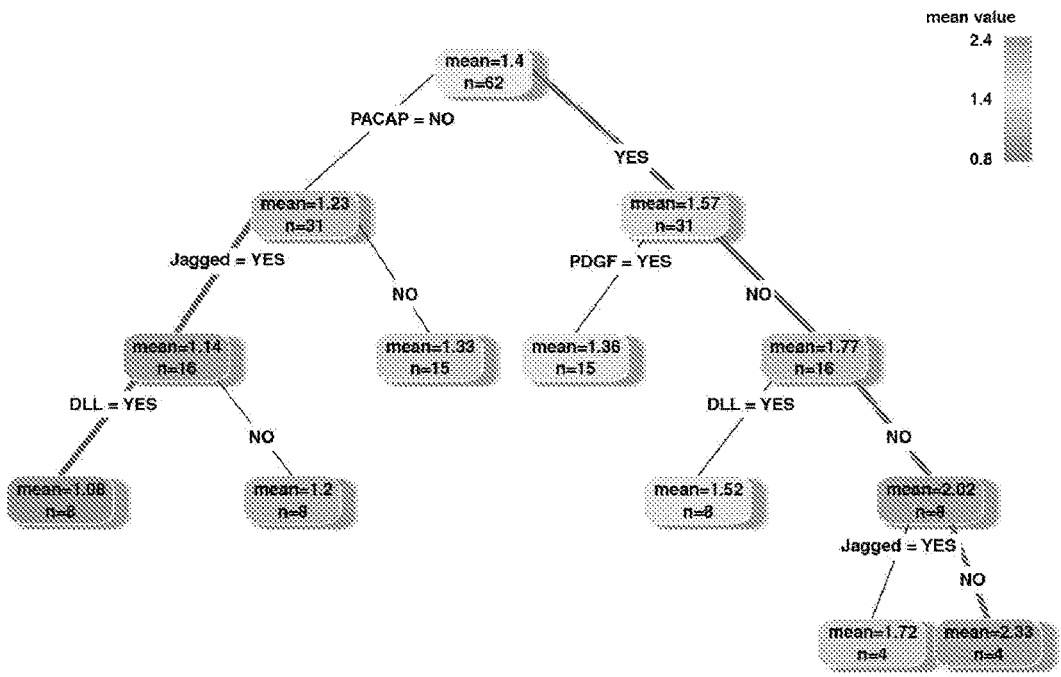
B
Decision tree analysis based on Hes5-GFP expression (combinatorial input)
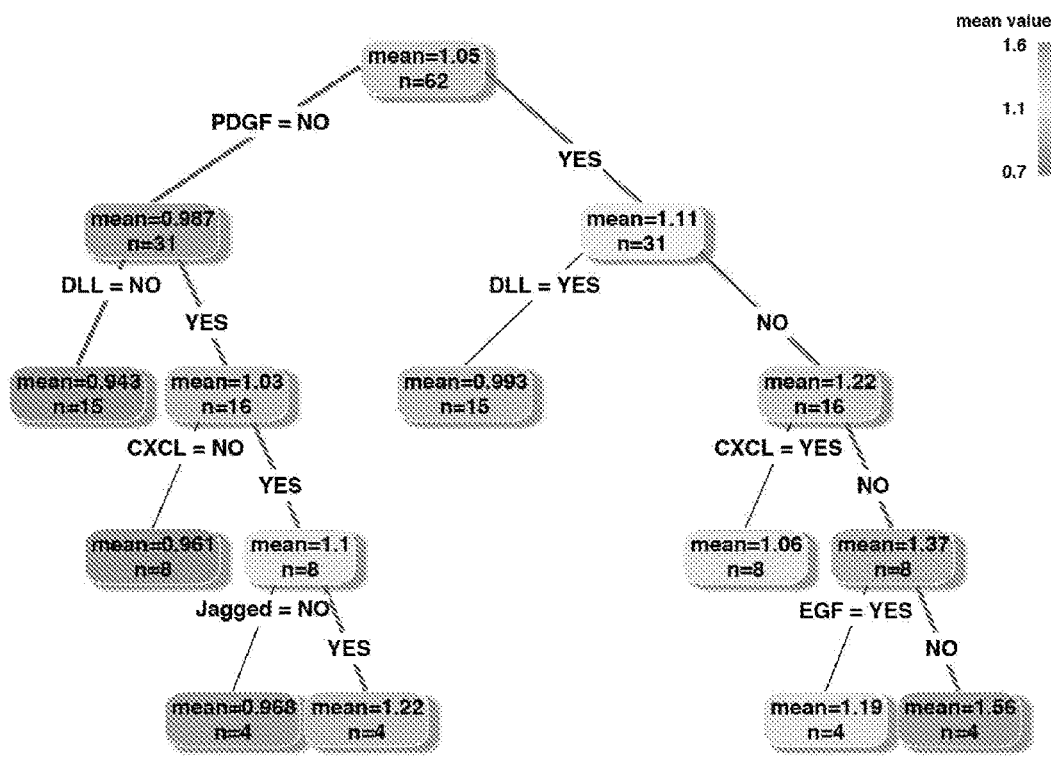
FIG. 18

FIG. 22-1

| Ligands combination | Cell counts (all) | Cell counts (Hes5$^+$) | Cell counts (Dcx$^+$) | Hes5-GFP | Dcx-RFP |
|---|---|---|---|---|---|
| 8,11,12,9,7,10 | 0.8 | 0.7 | 0.9 | 1.0 | 1.3 |
| 11,10,7,9,8,12 | 0.6 | 0.4 | 0.8 | 1.1 | 1.1 |
| 11,9,12,7,10,8 | 0.8 | 0.9 | 0.7 | 1.1 | 1.0 |
| 12,10,11,8,9,7 | 0.5 | 0.4 | 0.5 | 1.2 | 0.9 |
| 10,9,8,12,11,7 | 1.4 | 1.1 | 2.0 | 1.0 | 0.9 |
| 10,9,7,8,12,11 | 1.2 | 0.9 | 1.3 | 1.0 | 0.7 |
| 8,12,10,9,7,11 | 1.2 | 1.0 | 1.4 | 1.0 | 0.7 |
| 12,8,11,9,10,7 | 1.1 | 1.0 | 1.3 | 1.2 | 0.7 |
| 8,10,12,11,7,9 | 1.0 | 0.7 | 1.1 | 1.0 | 0.7 |
| 9,8,11,12,10,7 | 0.5 | 0.4 | 0.5 | 1.0 | 1.7 |
| 12,10,8,7,11,9 | 0.9 | 0.7 | 0.8 | 1.2 | 0.9 |
| 10,11,8,9,7,12 | 0.7 | 0.7 | 0.5 | 1.1 | 1.2 |
| 11,7,12,9,10,8 | 0.7 | 1.0 | 0.3 | 1.1 | 1.7 |
| 10,9,8,11,12,7 | 0.4 | 0.4 | 0.5 | 1.0 | 0.8 |
| 8,10,9,7,12,11 | 0.6 | 0.8 | 0.6 | 1.0 | 1.3 |
| 10,9,11,7,8,12 | 0.8 | 0.4 | 1.2 | 1.0 | 0.8 |
| 9,11,7,10,8,12 | 0.6 | 0.2 | 1.4 | 0.0 | 0.7 |
| 10,9,11,12,8,7 | 0.7 | 0.6 | 1.6 | 1.0 | 0.7 |
| 10,7,11,12,8,9 | 1.0 | 0.6 | 2.1 | 1.0 | 0.7 |
| 11,8,9,12,7,10 | 1.1 | 0.7 | 2.3 | 1.1 | 0.7 |
| 10,7,9,8,12,11 | 1.5 | 1.3 | 1.8 | 1.0 | 0.7 |
| 8,9,10,11,7,12 | 0.5 | 0.6 | 0.6 | 1.0 | 0.0 |
| 11,9,12,10,7,8 | 1.0 | 1.0 | 1.0 | 1.1 | 0.8 |
| 10,11,7,9,8,12 | 1.3 | 0.8 | 2.8 | 1.1 | 0.7 |
| 11,7,12,10,8,9 | 1.0 | 0.8 | 1.1 | 1.1 | 0.9 |
| 10,11,9,7,12,8 | 0.9 | 0.7 | 1.1 | 1.1 | 0.9 |
| 10,12,11,9,7,8 | 1.1 | 0.8 | 1.4 | 1.1 | 0.8 |
| 9,11,12,7,10,8 | 1.1 | 1.2 | 1.4 | 1.0 | 0.7 |
| 12,10,9,8,7,11 | 0.5 | 0.7 | 0.4 | 1.2 | 1.0 |
| 12,8,9,10,7,11 | 0.5 | 0.6 | 0.2 | 1.2 | 1.1 |
| 11,12,9,7,8,10 | 1.3 | 1.1 | 1.3 | 1.2 | 0.9 |
| 11,10,9,7,8,12 | 0.9 | 1.2 | 0.2 | 1.1 | 1.0 |
| 8,9,10,7,12,11 | 0.6 | 0.5 | 2.0 | 1.0 | 1.2 |
| 12,8,9,11,7,10 | 1.2 | 1.2 | 0.9 | 1.2 | 1.0 |
| 10,12,8,11,9,7 | 1.5 | 1.1 | 1.5 | 1.0 | 0.8 |
| 11,9,10,12,8,7 | 0.9 | 1.2 | 0.5 | 1.1 | 1.1 |
| 10,7,12,11,9,8 | 1.6 | 1.2 | 2.1 | 1.0 | 0.7 |
| 10,9,7,11,8,12 | 2.0 | 2.2 | 0.6 | 1.0 | 2.2 |
| 10,7,11,8,12,9 | 2.2 | 2.7 | 1.5 | 1.0 | 0.8 |
| 12,8,9,7,10,11 | 0.9 | 0.6 | 1.1 | 1.2 | 0.8 |
| 11,9,7,12,10,8 | 1.4 | 1.2 | 1.7 | 1.1 | 0.9 |
| 10,9,12,7,11,8 | 0.8 | 0.9 | 0.6 | 1.0 | 1.0 |

FIG. 22-2

| Ligands combination | Cell counts (all) | Cell counts (Hes5+) | Cell counts (Dcx+) | Hes5-GFP | Dcx-RFP |
|---|---|---|---|---|---|
| 9,11,8,7,10,12 | 1.7 | 1.4 | 1.6 | 0.9 | 0.7 |
| 10,11,7,12,8,9 | 0.7 | 0.6 | 0.7 | 1.1 | 0.8 |
| 9,11,12,10,7,8 | 1.0 | 0.9 | 1.2 | 1.0 | 0.8 |
| 10,9,8,11,7,12 | 1.0 | 0.9 | 1.0 | 1.0 | 1.3 |
| 10,8,12,11,7,9 | 1.4 | 1.5 | 0.9 | 1.0 | 0.7 |
| 11,8,10,9,12,7 | 1.3 | 1.2 | 1.1 | 1.1 | 0.9 |
| 11,7,10,9,8,12 | 1.0 | 1.6 | 0.6 | 1.1 | 1.2 |
| 11,7,12,10,9,8 | 0.5 | 1.1 | 0.4 | 1.1 | 0.9 |
| 9,7,10,8,12,11 | 0.3 | 0.3 | 0.7 | 1.0 | 1.1 |
| 12,10,9,11,7,8 | 0.8 | 0.7 | 0.6 | 1.2 | 0.7 |
| 12,9,8,7,10,11 | 1.1 | 1.3 | 0.9 | 1.2 | 0.9 |
| 11,10,8,9,7,12 | 1.1 | 0.7 | 1.4 | 1.1 | 0.9 |
| 10,11,12,8,7,9 | 1.0 | 0.7 | 2.0 | 1.1 | 0.8 |
| 10,12,7,11,8,9 | 1.2 | 1.1 | 1.4 | 1.0 | 0.8 |
| 12,7,10,9,11,8 | 2.1 | 1.6 | 2.5 | 1.2 | 0.8 |
| 8,9,11,10,7,12 | 1.4 | 1.4 | 1.5 | 1.0 | 1.0 |
| 12,8,11,9,7,10 | 0.3 | 0.3 | 0.2 | 1.2 | 0.8 |
| 9,11,7,10,12,8 | 0.1 | 0.1 | 0.3 | 0.0 | 0.0 |
| 9,12,10,8,7,11 | 1.3 | 1.1 | 1.3 | 1.1 | 0.9 |
| 9,12,11,8,10,7 | 1.6 | 1.2 | 1.4 | 1.1 | 0.6 |
| 12,9,11,10,7,8 | 0.3 | 0.2 | 0.4 | 1.2 | 0.9 |
| 8,12,11,9,10,7 | 1.1 | 1.3 | 0.9 | 1.0 | 0.9 |
| 12,7,10,8,11,9 | 0.5 | 0.4 | 0.5 | 1.2 | 1.0 |
| 11,10,8,7,9,12 | 0.3 | 0.5 | 0.3 | 1.1 | 0.9 |
| 11,9,10,7,8,12 | 0.8 | 1.1 | 0.7 | 1.1 | 1.2 |
| 9,10,11,12,8,7 | 0.3 | 0.2 | 0.4 | 0.0 | 2.3 |
| 11,10,8,12,9,7 | 0.8 | 0.6 | 0.8 | 1.1 | 0.9 |
| 12,11,7,10,9,8 | 0.7 | 0.6 | 0.8 | 1.3 | 1.1 |
| 11,8,12,10,9,7 | 0.9 | 0.7 | 1.8 | 1.1 | 1.0 |
| 9,8,10,7,11,12 | 1.0 | 0.8 | 1.0 | 1.1 | 0.9 |
| 8,10,9,12,11,7 | 1.8 | 2.4 | 1.3 | 1.0 | 0.9 |
| 11,12,9,7,10,8 | 0.2 | 0.2 | 0.2 | 1.2 | 1.0 |
| 12,7,10,11,9,8 | 0.3 | 0.3 | 0.3 | 1.2 | 0.7 |
| 9,10,11,12,7,8 | 0.7 | 0.2 | 1.1 | 0.0 | 0.0 |
| 8,12,10,7,11,9 | 1.3 | 0.9 | 1.4 | 1.0 | 0.6 |
| 10,11,12,7,9,8 | 0.4 | 0.4 | 0.5 | 1.1 | 0.7 |
| 10,11,8,7,9,12 | 0.9 | 0.4 | 1.3 | 1.1 | 0.9 |
| 11,10,8,12,7,9 | 0.4 | 0.3 | 0.7 | 1.1 | 0.6 |
| 11,9,7,8,10,12 | 0.5 | 0.4 | 0.6 | 1.1 | 0.9 |
| 11,8,12,7,9,10 | 0.8 | 0.8 | 0.3 | 1.1 | 49.4 |
| 8,9,12,10,7,11 | 1.3 | 1.1 | 1.3 | 1.0 | 0.9 |
| 8,10,12,11,9,7 | 1.1 | 1.2 | 0.9 | 1.0 | 1.2 |

FIG. 22-3

| Ligands combination | Cell counts (all) | Cell counts (Hes5+) | Cell counts (Dcx+) | Hes5-GFP | Dcx-RFP |
|---|---|---|---|---|---|
| 8,12,9,10,7,11 | 1.5 | 3.8 | 0.8 | 1.0 | 1.1 |
| 11,8,9,10,12,7 | 0.9 | 1.1 | 0.8 | 1.1 | 1.0 |
| 10,12,9,11,7,8 | 1.4 | 1.0 | 2.9 | 1.0 | 0.8 |
| 12,7,11,10,9,8 | 0.5 | 0.6 | 0.3 | 1.2 | 0.9 |
| 10,9,11,7,12,8 | 0.8 | 0.4 | 4.7 | 1.0 | 0.7 |
| 9,8,10,7,12,11 | 1.1 | 1.3 | 0.9 | 1.1 | 1.0 |
| 8,10,12,9,7,11 | 1.1 | 1.2 | 0.8 | 1.0 | 0.0 |
| 11,10,12,7,9,8 | 0.4 | 0.4 | 0.3 | 1.1 | 0.0 |
| 10,11,12,9,7,8 | 0.4 | 0.3 | 0.5 | 1.1 | 1.0 |
| 8,12,10,7,9,11 | 1.1 | 1.5 | 0.8 | 1.0 | 1.0 |
| 10,9,7,12,8,11 | 0.3 | 0.2 | 0.4 | 1.0 | 0.7 |
| 10,8,11,7,12,9 | 0.3 | 0.3 | 1.1 | 1.0 | 0.0 |
| 9,12,10,7,8,11 | 0.4 | 0.5 | 0.3 | 1.1 | 0.0 |
| 10,8,12,9,7,11 | 1.1 | 0.5 | 1.8 | 1.0 | 0.7 |
| 9,10,11,8,12,7 | 0.2 | 0.0 | 0.4 | 0.0 | 0.9 |
| 8,11,10,7,12,9 | 0.7 | 0.7 | 0.7 | 1.0 | 1.1 |
| 8,10,9,11,7,12 | 1.2 | 1.3 | 0.8 | 1.0 | 1.2 |
| 11,10,12,9,8,7 | 0.7 | 0.4 | 1.6 | 1.1 | 0.8 |
| 10,8,12,7,9,11 | 1.4 | 0.9 | 1.5 | 1.0 | 0.8 |
| 11,8,10,9,7,12 | 0.6 | 0.5 | 0.6 | 1.1 | 0.8 |
| 9,11,10,7,12,8 | 1.8 | 1.9 | 1.5 | 1.0 | 1.0 |
| 10,12,8,7,11,9 | 1.5 | 1.0 | 2.1 | 1.0 | 0.9 |
| 12,8,10,9,7,11 | 0.5 | 0.5 | 0.5 | 1.2 | 1.1 |
| 10,9,8,12,7,11 | 1.0 | 0.9 | 1.2 | 1.0 | 0.9 |
| 10,7,9,11,12,8 | 2.0 | 1.6 | 2.9 | 1.0 | 0.8 |
| 10,8,9,12,11,7 | 2.4 | 1.8 | 3.4 | 1.0 | 0.9 |
| 9,11,10,8,12,7 | 1.0 | 1.1 | 0.7 | 1.0 | 0.9 |
| 8,9,12,7,10,11 | 0.7 | 0.6 | 1.0 | 1.0 | 0.9 |
| 10,9,12,11,8,7 | 1.3 | 0.6 | 3.2 | 1.0 | 0.7 |
| 10,8,9,7,11,12 | 1.1 | 0.9 | 3.5 | 1.0 | 0.6 |
| 10,8,11,9,12,7 | 0.7 | 0.8 | 0.4 | 1.0 | 0.9 |
| 10,8,11,9,7,12 | 1.4 | 1.1 | 2.0 | 1.0 | 0.8 |
| 10,7,12,8,9,11 | 0.5 | 0.3 | 0.7 | 1.0 | 0.8 |
| 12,8,9,11,10,7 | 0.4 | 0.3 | 0.6 | 1.2 | 0.9 |
| 10,11,8,12,9,7 | 1.5 | 1.7 | 0.7 | 1.1 | 0.9 |
| 10,7,11,8,9,12 | 1.4 | 1.4 | 1.2 | 1.0 | 0.8 |
| 12,9,10,7,11,8 | 0.9 | 0.8 | 1.2 | 1.2 | 1.5 |
| 12,9,7,11,10,8 | 1.5 | 0.8 | 2.7 | 1.2 | 0.8 |
| 8,11,9,10,7,12 | 0.9 | 0.9 | 1.1 | 1.0 | 0.9 |
| 9,7,11,10,12,8 | 1.3 | 1.2 | 1.8 | 1.0 | 0.8 |
| 12,8,11,10,9,7 | 1.1 | 1.0 | 1.7 | 1.2 | 0.8 |
| 10,11,9,12,7,8 | 1.5 | 1.3 | 1.4 | 1.1 | 0.7 |

FIG. 22-4

| Ligands combination | Cell counts (all) | Cell counts (Hes5$^+$) | Cell counts (Dcx$^+$) | Hes5-GFP | Dcx-RFP |
|---|---|---|---|---|---|
| 11,10,12,9,7,8 | 0.7 | 0.7 | 0.8 | 1.1 | 0.7 |
| 9,11,8,12,7,10 | 0.8 | 2.4 | 0.5 | 1.0 | 0.9 |
| 9,10,7,8,12,11 | 1.0 | 0.7 | 1.0 | 1.1 | 1.0 |
| 9,12,11,10,8,7 | 0.6 | 0.5 | 0.7 | 1.1 | 0.7 |
| 8,9,11,12,10,7 | 0.8 | 0.6 | 0.8 | 1.0 | 0.8 |
| 10,9,12,8,7,11 | 1.5 | 0.9 | 2.5 | 1.0 | 0.7 |
| 10,12,7,8,11,9 | 0.5 | 1.1 | 0.4 | 1.0 | 0.9 |
| 10,9,12,8,11,7 | 1.1 | 0.7 | 1.9 | 1.0 | 0.8 |
| 9,10,11,8,7,12 | 0.5 | 0.1 | 1.7 | 0.0 | 0.9 |
| 9,12,11,7,10,8 | 0.8 | 0.8 | 0.8 | 1.1 | 0.9 |
| 12,10,7,9,11,8 | 0.2 | 0.3 | 0.2 | 1.2 | 1.0 |
| 12,9,7,10,11,8 | 0.5 | 3.5 | 0.0 | 1.2 | 0.0 |
| 9,12,8,7,11,10 | 0.8 | 0.7 | 0.8 | 1.1 | 1.0 |
| 12,10,7,8,11,9 | 0.3 | 0.3 | 0.2 | 1.2 | 0.9 |
| 9,10,11,7,8,12 | 0.1 | 0.0 | 0.1 | 0.0 | 0.0 |
| 9,12,10,11,7,8 | 0.9 | 0.8 | 1.0 | 1.1 | 0.9 |
| 9,12,8,11,10,7 | 1.1 | 1.4 | 1.0 | 1.1 | 0.8 |
| 12,7,11,10,8,9 | 0.4 | 0.4 | 0.4 | 1.2 | 0.6 |
| 11,12,8,10,9,7 | 0.5 | 0.5 | 0.7 | 1.2 | 0.7 |
| 10,9,11,12,7,8 | 0.2 | 0.2 | 0.3 | 1.0 | 0.9 |
| 12,8,10,11,9,7 | 0.3 | 0.4 | 0.3 | 1.2 | 1.1 |
| 11,7,9,10,8,12 | 0.6 | 0.6 | 0.7 | 1.1 | 1.1 |
| 12,10,11,9,8,7 | 0.3 | 0.3 | 0.6 | 1.3 | 0.6 |
| 11,7,10,9,12,8 | 1.0 | 0.9 | 1.7 | 1.1 | 0.7 |
| 12,9,8,10,11,7 | 0.3 | 0.3 | 0.3 | 1.2 | 0.9 |
| 12,7,9,11,10,8 | 0.7 | 0.5 | 0.8 | 1.2 | 0.8 |
| 11,12,10,7,8,9 | 0.6 | 0.6 | 0.5 | 1.2 | 1.1 |
| 8,12,9,7,11,10 | 2.0 | 1.1 | 6.3 | 1.0 | 1.0 |
| 11,7,10,12,9,8 | 0.7 | 0.4 | 2.6 | 1.1 | 0.9 |
| 9,10,11,7,12,8 | 0.1 | 0.0 | 0.2 | 0.0 | 1.1 |
| 12,9,11,10,8,7 | 0.3 | 0.2 | 0.3 | 1.2 | 0.9 |
| 9,10,12,11,8,7 | 1.1 | 0.0 | 2.3 | 0.0 | 0.8 |
| 10,11,8,9,12,7 | 1.7 | 1.6 | 1.8 | 1.1 | 0.8 |
| 10,12,11,9,8,7 | 0.7 | 0.7 | 0.8 | 1.1 | 0.7 |
| 11,8,12,9,10,7 | 0.7 | 0.8 | 0.7 | 1.1 | 0.8 |
| 10,12,9,7,11,8 | 0.5 | 0.5 | 0.6 | 1.0 | 0.8 |
| 10,9,11,8,7,12 | 0.9 | 1.2 | 1.1 | 1.0 | 0.9 |
| 11,9,7,10,12,8 | 1.1 | 1.4 | 0.3 | 1.1 | 51.0 |
| 9,12,11,7,8,10 | 1.4 | 1.5 | 1.2 | 1.1 | 0.8 |
| 11,7,9,12,8,10 | 0.5 | 0.4 | 0.9 | 1.1 | 0.7 |
| 8,12,9,7,10,11 | 1.6 | 1.5 | 2.2 | 1.0 | 1.0 |
| 11,10,12,8,7,9 | 1.0 | 1.3 | 0.8 | 1.1 | 1.0 |

FIG. 22-5

| Ligands combination | Cell counts (all) | Cell counts (Hes5$^+$) | Cell counts (Dcx$^+$) | Hes5-GFP | Dcx-RFP |
|---|---|---|---|---|---|
| 11,8,9,7,10,12 | 1.1 | 0.8 | 3.0 | 1.1 | 0.8 |
| 8,11,12,10,7,9 | 1.0 | 0.8 | 1.2 | 1.0 | 1.1 |
| 12,9,10,8,7,11 | 0.3 | 0.3 | 0.3 | 1.2 | 0.9 |
| 10,8,11,12,7,9 | 1.1 | 0.6 | 2.9 | 1.0 | 0.7 |
| 12,10,8,11,7,9 | 0.8 | 0.5 | 1.9 | 1.2 | 0.9 |
| 9,7,12,10,8,11 | 1.5 | 1.6 | 1.4 | 1.0 | 1.0 |
| 12,7,10,9,8,11 | 0.5 | 0.3 | 0.8 | 1.2 | 0.9 |
| 10,7,12,11,8,9 | 0.6 | 0.5 | 10.7 | 1.0 | 0.6 |
| 9,11,10,12,8,7 | 0.2 | 0.2 | 0.4 | 1.0 | 0.7 |
| 8,11,12,9,10,7 | 1.1 | 1.1 | 0.8 | 1.0 | 1.1 |
| 9,11,12,8,7,10 | 0.4 | 0.4 | 0.2 | 1.0 | 1.2 |
| 9,11,8,10,7,12 | 0.8 | 0.5 | 1.0 | 0.9 | 0.7 |
| 9,7,10,12,8,11 | 1.3 | 1.1 | 1.4 | 1.0 | 0.7 |
| 9,7,12,10,11,8 | 1.0 | 1.4 | 1.1 | 1.0 | 1.0 |
| 11,12,8,9,10,7 | 1.0 | 0.7 | 2.2 | 1.2 | 0.9 |
| 10,9,11,8,12,7 | 1.4 | 0.9 | 1.8 | 1.0 | 0.8 |
| 8,10,9,7,11,12 | 3.6 | 4.0 | 2.8 | 1.0 | 1.1 |
| 11,12,10,9,7,8 | 1.1 | 0.7 | 1.6 | 1.2 | 0.8 |
| 10,7,12,9,11,8 | 1.6 | 1.7 | 1.0 | 1.0 | 0.9 |
| 8,11,12,10,9,7 | 1.3 | 1.1 | 1.4 | 1.0 | 0.9 |
| 10,12,8,9,7,11 | 1.3 | 0.8 | 2.1 | 1.0 | 0.9 |
| 9,11,12,8,10,7 | 1.5 | 1.3 | 2.1 | 1.0 | 0.8 |
| 11,10,7,12,8,9 | 0.4 | 0.3 | 0.4 | 1.1 | 1.0 |
| 9,7,11,8,10,12 | 1.2 | 1.0 | 1.3 | 1.0 | 0.9 |
| 10,9,8,7,11,12 | 1.1 | 1.0 | 1.1 | 1.0 | 0.9 |
| 9,11,10,12,7,8 | 2.4 | 2.3 | 2.9 | 1.0 | 0.8 |
| 10,8,9,11,12,7 | 0.9 | 0.8 | 0.8 | 1.0 | 0.8 |
| 10,7,9,12,11,8 | 2.6 | 2.1 | 3.0 | 1.0 | 0.7 |
| 9,8,12,11,10,7 | 1.1 | 1.5 | 0.9 | 1.1 | 1.1 |
| 10,11,9,8,7,12 | 1.5 | 0.8 | 2.8 | 1.1 | 0.7 |
| 10,8,9,7,12,11 | 2.3 | 2.1 | 3.4 | 1.0 | 0.7 |
| 10,7,12,9,8,11 | 1.2 | 0.8 | 2.1 | 1.0 | 0.8 |
| 10,7,11,9,8,12 | 0.7 | 0.7 | 0.6 | 1.0 | 0.9 |
| 9,11,7,12,8,10 | 0.6 | 0.3 | 0.7 | 0.9 | 0.9 |
| 11,8,9,12,10,7 | 1.1 | 1.4 | 0.7 | 1.1 | 1.0 |
| 10,7,9,11,8,12 | 2.3 | 3.2 | 1.2 | 1.0 | 0.8 |
| 9,8,12,7,11,10 | 0.0 | 0.0 | 0.0 | 1.0 | 1.0 |
| 12,9,8,10,7,11 | 0.6 | 0.6 | 0.6 | 1.2 | 1.3 |
| 11,7,9,8,10,12 | 1.8 | 2.0 | 1.7 | 1.1 | 0.9 |
| 8,9,10,7,11,12 | 0.7 | 0.4 | 1.1 | 1.0 | 1.1 |
| 9,10,12,11,7,8 | 1.2 | 0.4 | 1.9 | 0.0 | 0.8 |
| 12,11,7,8,10,9 | 1.2 | 0.7 | 2.1 | 1.3 | 0.7 |

FIG. 22-6

| Ligands combination | Cell counts (all) | Cell counts (Hes5+) | Cell counts (Dcx+) | Hes5-GFP | Dcx-RFP |
|---|---|---|---|---|---|
| 8,10,12,9,11,7 | 2.4 | 2.1 | 3.0 | 1.0 | 1.0 |
| 11,12,10,8,9,7 | 1.2 | 1.0 | 2.1 | 1.2 | 0.7 |
| 12,9,10,7,8,11 | 0.9 | 0.7 | 0.9 | 1.2 | 0.8 |
| 10,8,12,11,9,7 | 1.7 | 1.7 | 1.7 | 1.0 | 0.8 |
| 9,7,10,11,12,8 | 0.7 | 0.9 | 0.6 | 1.0 | 1.1 |
| 8,12,10,11,9,7 | 1.7 | 3.4 | 1.4 | 1.0 | 1.0 |
| 10,9,7,12,11,8 | 1.8 | 1.0 | 3.3 | 1.0 | 0.8 |
| 8,10,11,7,12,9 | 0.9 | 0.7 | 1.1 | 1.0 | 0.9 |
| 10,8,12,7,11,9 | 0.8 | 3.9 | 0.6 | 1.0 | 0.9 |
| 10,7,12,8,11,9 | 1.3 | 1.1 | 1.4 | 1.0 | 0.8 |
| 9,10,12,8,11,7 | 0.2 | 0.1 | 0.5 | 0.0 | 1.0 |
| 12,10,8,7,9,11 | 0.4 | 0.6 | 0.5 | 1.2 | 0.9 |
| 11,12,7,8,9,10 | 1.1 | 0.7 | 2.1 | 1.1 | 0.9 |
| 11,12,8,9,7,10 | 0.4 | 0.6 | 0.2 | 1.2 | 0.8 |
| 12,10,9,7,8,11 | 1.1 | 0.5 | 1.4 | 1.2 | 0.7 |
| 12,10,11,8,7,9 | 0.2 | 0.3 | 0.2 | 1.2 | 0.8 |
| 11,10,7,9,12,8 | 0.5 | 0.9 | 0.4 | 1.1 | 0.7 |
| 11,12,9,8,7,10 | 0.7 | 0.6 | 0.7 | 1.2 | 0.8 |
| 11,9,12,8,7,10 | 0.7 | 1.2 | 0.6 | 1.1 | 0.9 |
| 9,10,12,8,7,11 | 0.3 | 0.1 | 0.4 | 0.0 | 1.0 |
| 10,9,12,11,7,8 | 0.5 | 0.7 | 0.4 | 1.0 | 1.0 |
| 11,9,12,10,8,7 | 0.6 | 0.7 | 0.5 | 1.1 | 0.9 |
| 10,11,12,8,9,7 | 1.1 | 1.2 | 1.2 | 1.1 | 0.8 |
| 9,12,11,10,7,8 | 0.7 | 1.0 | 0.6 | 1.1 | 1.0 |
| 12,10,7,8,9,11 | 0.6 | 0.7 | 0.7 | 1.2 | 0.7 |
| 11,10,12,8,9,7 | 1.8 | 0.9 | 4.1 | 1.1 | 0.7 |
| 9,12,7,11,8,10 | 0.7 | 0.7 | 0.6 | 1.1 | 1.3 |
| 8,11,12,7,10,9 | 0.6 | 0.8 | 0.4 | 1.0 | 1.2 |
| 8,11,9,7,10,12 | 1.1 | 0.9 | 1.1 | 1.0 | 1.0 |
| 12,9,10,8,11,7 | 0.5 | 0.6 | 0.3 | 1.2 | 1.1 |
| 8,9,12,10,11,7 | 0.7 | 0.7 | 0.8 | 1.0 | 1.1 |
| 10,11,12,9,8,7 | 0.5 | 0.3 | 0.6 | 1.1 | 0.9 |
| 10,8,11,12,9,7 | 1.6 | 0.9 | 2.2 | 1.0 | 0.8 |
| 9,8,12,10,11,7 | 0.9 | 1.2 | 0.8 | 1.1 | 1.1 |
| 8,12,10,9,11,7 | 0.9 | 1.0 | 0.7 | 1.0 | 1.1 |
| 9,12,10,7,11,8 | 0.6 | 0.7 | 0.4 | 1.1 | 0.0 |
| 9,7,10,12,11,8 | 0.8 | 0.8 | 0.8 | 1.0 | 1.1 |
| 12,8,11,7,9,10 | 0.5 | 0.4 | 1.0 | 1.2 | 0.8 |
| 12,7,11,9,10,8 | 0.7 | 0.4 | 1.5 | 1.2 | 0.7 |
| 12,7,9,10,8,11 | 0.5 | 0.2 | 1.0 | 1.2 | 0.8 |
| 11,12,9,10,7,8 | 1.2 | 0.9 | 2.1 | 1.2 | 0.8 |
| 9,8,10,11,7,12 | 0.6 | 0.5 | 0.6 | 1.1 | 1.0 |

FIG. 22-7

| Ligands combination | Cell counts (all) | Cell counts (Hes5$^+$) | Cell counts (Dcx$^+$) | Hes5-GFP | Dcx-RFP |
|---|---|---|---|---|---|
| 11,12,7,10,9,8 | 0.3 | 0.3 | 0.3 | 1.1 | 1.2 |
| 9,8,11,12,7,10 | 0.9 | 0.7 | 0.9 | 1.0 | 1.0 |
| 11,12,9,8,10,7 | 1.4 | 0.9 | 1.9 | 1.2 | 0.8 |
| 10,11,8,7,12,9 | 1.5 | 1.4 | 1.5 | 1.1 | 0.8 |
| 12,10,9,11,8,7 | 0.2 | 0.1 | 0.4 | 1.2 | 1.3 |
| 10,7,11,9,12,8 | 0.7 | 0.7 | 0.5 | 1.0 | 0.9 |
| 12,9,7,11,8,10 | 1.3 | 0.9 | 1.3 | 1.2 | 0.8 |
| 12,8,11,7,10,9 | 1.5 | 0.7 | 2.5 | 1.2 | 0.8 |
| 9,7,11,10,8,12 | 0.8 | 0.9 | 0.9 | 1.0 | 1.1 |
| 11,7,10,12,8,9 | 0.8 | 0.6 | 0.9 | 1.1 | 0.9 |
| 10,7,9,8,11,12 | 2.2 | 1.8 | 4.3 | 1.0 | 0.7 |
| 12,7,10,11,8,9 | 1.2 | 1.2 | 0.9 | 1.2 | 0.9 |
| 11,9,8,7,10,12 | 0.7 | 0.8 | 0.4 | 1.1 | 0.9 |
| 8,10,11,12,9,7 | 0.7 | 0.6 | 0.6 | 1.0 | 1.0 |
| 11,8,10,12,9,7 | 1.0 | 0.8 | 0.8 | 1.1 | 1.0 |
| 10,9,12,7,8,11 | 2.4 | 2.0 | 3.7 | 1.0 | 0.7 |
| 12,9,7,8,10,11 | 0.6 | 0.2 | 1.9 | 1.2 | 0.8 |
| 11,9,10,12,7,8 | 0.4 | 0.4 | 0.4 | 1.1 | 0.8 |
| 8,11,9,12,10,7 | 0.9 | 0.8 | 1.0 | 1.0 | 1.0 |
| 11,8,10,12,7,9 | 1.4 | 1.4 | 2.1 | 1.1 | 0.6 |
| 10,8,9,12,7,11 | 1.7 | 1.3 | 2.2 | 1.0 | 0.7 |
| 8,9,12,11,10,7 | 0.8 | 0.9 | 0.6 | 1.0 | 1.1 |
| 12,9,11,7,10,8 | 1.2 | 0.9 | 1.8 | 1.2 | 0.8 |
| 10,12,11,8,9,7 | 0.8 | 0.3 | 1.2 | 1.1 | 0.8 |
| 8,9,10,11,12,7 | 0.9 | 1.0 | 0.7 | 1.0 | 0.9 |
| 9,7,10,11,8,12 | 0.9 | 0.9 | 0.5 | 1.0 | 1.2 |
| 10,12,8,9,11,7 | 0.3 | 0.4 | 0.2 | 1.0 | 0.9 |
| 11,8,12,10,7,9 | 1.7 | 1.3 | 1.3 | 1.1 | 0.9 |
| 11,7,12,8,10,9 | 2.1 | 0.9 | 9.7 | 1.1 | 0.8 |
| 11,12,10,8,7,9 | 1.3 | 1.7 | 1.3 | 1.2 | 0.8 |
| 12,9,7,8,11,10 | 0.7 | 0.6 | 0.8 | 1.2 | 0.8 |
| 9,10,12,7,8,11 | 0.6 | 0.3 | 0.7 | 0.0 | 0.8 |
| 12,10,7,9,8,11 | 0.5 | 0.5 | 0.8 | 1.2 | 0.8 |
| 9,12,8,10,11,7 | 1.1 | 0.9 | 2.0 | 1.1 | 1.1 |
| 8,9,12,11,7,10 | 1.0 | 0.9 | 1.0 | 1.0 | 1.1 |
| 12,8,9,7,11,10 | 0.3 | 0.4 | 0.4 | 1.2 | 0.8 |
| 12,7,10,8,9,11 | 0.6 | 0.6 | 0.7 | 1.2 | 0.8 |
| 11,12,7,10,8,9 | 1.8 | 0.9 | 3.0 | 1.1 | 0.7 |
| 11,7,12,9,8,10 | 0.5 | 0.5 | 0.5 | 1.1 | 0.7 |
| 11,12,8,10,7,9 | 0.5 | 0.5 | 0.6 | 1.2 | 0.9 |
| 11,12,8,7,10,9 | 0.7 | 0.7 | 0.7 | 1.2 | 0.9 |
| 11,10,9,8,7,12 | 0.4 | 0.3 | 0.7 | 1.1 | 0.9 |

FIG. 22-8

| Ligands combination | Cell counts (all) | Cell counts (Hes5$^+$) | Cell counts (Dcx$^+$) | Hes5-GFP | Dcx-RFP |
|---|---|---|---|---|---|
| 10,9,7,11,12,8 | 0.3 | 0.1 | 0.5 | 1.0 | 1.0 |
| 9,11,8,12,10,7 | 2.4 | 1.7 | 5.5 | 1.0 | 0.6 |
| 9,11,8,7,12,10 | 0.7 | 0.6 | 0.6 | 0.9 | 0.7 |
| 12,8,10,9,11,7 | 0.3 | 0.3 | 0.4 | 1.2 | 1.0 |
| 11,10,7,8,12,9 | 0.6 | 0.7 | 0.6 | 1.1 | 0.7 |
| 10,11,9,12,8,7 | 0.4 | 0.6 | 0.2 | 1.1 | 0.9 |
| 11,10,8,7,12,9 | 1.3 | 1.1 | 1.6 | 1.1 | 0.7 |
| 10,11,9,8,12,7 | 1.8 | 1.4 | 3.1 | 1.1 | 0.7 |
| 10,12,7,11,9,8 | 1.1 | 1.4 | 0.3 | 1.0 | 1.4 |
| 9,11,10,8,7,12 | 0.8 | 1.2 | 0.0 | 1.0 | 0.0 |
| 11,12,7,8,10,9 | 2.7 | 1.6 | 11.3 | 1.1 | 0.8 |
| 11,10,9,12,7,8 | 1.0 | 0.8 | 1.1 | 1.1 | 0.7 |
| 12,10,7,11,9,8 | 1.1 | 0.5 | 1.7 | 1.2 | 0.9 |
| 11,9,12,8,10,7 | 1.1 | 0.7 | 2.0 | 1.1 | 0.9 |
| 9,12,7,10,11,8 | 0.7 | 0.6 | 0.9 | 1.1 | 0.9 |
| 10,12,11,7,9,8 | 2.9 | 1.3 | 4.8 | 1.1 | 0.6 |
| 12,10,7,11,8,9 | 1.1 | 1.3 | 0.5 | 1.2 | 1.6 |
| 11,9,7,10,8,12 | 2.5 | 2.8 | 1.4 | 1.1 | 1.2 |
| 9,12,7,11,10,8 | 1.2 | 1.3 | 1.0 | 1.1 | 1.0 |
| 12,10,8,9,7,11 | 1.4 | 1.6 | 1.2 | 1.2 | 0.9 |
| 8,11,12,7,9,10 | 0.6 | 1.6 | 0.4 | 1.0 | 1.1 |
| 9,12,8,10,7,11 | 0.7 | 1.0 | 0.8 | 1.1 | 1.0 |
| 9,12,10,11,8,7 | 1.0 | 1.1 | 0.9 | 1.1 | 1.0 |
| 9,12,10,8,11,7 | 1.9 | 1.5 | 3.2 | 1.1 | 0.8 |
| 9,8,12,11,7,10 | 0.7 | 0.9 | 0.5 | 1.1 | 1.1 |
| 11,9,7,8,12,10 | 2.2 | 1.1 | 2.7 | 1.1 | 0.8 |
| 10,11,7,12,9,8 | 2.4 | 2.2 | 2.1 | 1.1 | 0.7 |
| 9,10,7,8,11,12 | 0.9 | 1.0 | 0.7 | 1.1 | 0.7 |
| 12,10,11,9,7,8 | 0.8 | 0.6 | 0.8 | 1.2 | 0.8 |
| 9,10,7,11,8,12 | 1.5 | 1.5 | 1.5 | 1.1 | 1.0 |
| 8,11,9,10,12,7 | 0.9 | 0.9 | 0.8 | 1.0 | 1.0 |
| 12,8,10,11,7,9 | 0.5 | 0.5 | 0.9 | 1.2 | 0.6 |
| 12,9,11,8,10,7 | 0.8 | 0.7 | 1.4 | 1.2 | 0.7 |
| 11,8,10,7,12,9 | 0.9 | 0.8 | 1.2 | 1.1 | 0.8 |
| 9,12,8,11,7,10 | 1.1 | 1.2 | 0.8 | 1.1 | 0.0 |
| 11,9,8,12,7,10 | 0.9 | 0.6 | 1.5 | 1.1 | 0.8 |
| 11,9,8,10,7,12 | 1.1 | 0.7 | 2.0 | 1.1 | 0.8 |
| 10,11,7,8,12,9 | 0.7 | 0.6 | 1.2 | 1.1 | 0.7 |
| 10,7,9,12,8,11 | 1.1 | 1.3 | 0.9 | 1.0 | 0.8 |
| 8,11,10,12,9,7 | 1.0 | 1.1 | 0.7 | 1.0 | 0.0 |
| 10,12,11,7,8,9 | 2.3 | 1.9 | 2.3 | 1.1 | 0.7 |
| 10,12,9,8,11,7 | 0.5 | 0.5 | 0.5 | 1.0 | 0.8 |

FIG. 22-9

| Ligands combination | Cell counts (all) | Cell counts (Hes5+) | Cell counts (Dcx+) | Hes5-GFP | Dcx-RFP |
|---|---|---|---|---|---|
| 12,10,8,9,11,7 | 0.4 | 0.2 | 0.4 | 1.2 | 0.7 |
| 11,10,9,8,12,7 | 0.9 | 0.9 | 1.0 | 1.1 | 0.7 |
| 12,10,11,7,9,8 | 0.7 | 0.6 | 0.8 | 1.2 | 0.8 |
| 12,10,11,7,8,9 | 1.1 | 1.0 | 1.0 | 1.2 | 0.8 |
| 9,11,7,8,12,10 | 0.6 | 0.8 | 0.4 | 0.9 | 0.7 |
| 9,11,7,8,10,12 | 1.7 | 1.7 | 1.7 | 0.9 | 0.6 |
| 12,9,8,7,11,10 | 0.5 | 0.4 | 0.9 | 1.2 | 0.7 |
| 10,11,8,12,7,9 | 0.9 | 0.9 | 0.9 | 1.1 | 0.6 |
| 9,11,7,12,10,8 | 1.6 | 1.4 | 1.6 | 0.9 | 0.7 |
| 11,10,9,7,12,8 | 1.9 | 1.4 | 2.4 | 1.1 | 0.8 |
| 11,9,12,7,8,10 | 1.3 | 0.9 | 4.7 | 1.1 | 0.9 |
| 9,8,10,12,11,7 | 0.8 | 1.0 | 0.6 | 1.1 | 1.1 |
| 8,11,10,12,7,9 | 0.9 | 0.8 | 0.7 | 1.0 | 1.1 |
| 12,11,7,10,8,9 | 0.7 | 0.4 | 1.2 | 1.3 | 0.8 |
| 9,8,11,10,7,12 | 1.0 | 1.0 | 1.2 | 1.0 | 1.0 |
| 12,10,9,7,11,8 | 1.0 | 0.8 | 1.2 | 1.2 | 0.9 |
| 12,10,8,11,9,7 | 0.6 | 0.7 | 0.5 | 1.2 | 0.9 |
| 10,11,12,7,8,9 | 0.9 | 1.0 | 0.8 | 1.1 | 0.9 |
| 8,10,11,12,7,9 | 1.0 | 1.1 | 1.0 | 1.0 | 1.0 |
| 9,8,12,7,10,11 | 0.9 | 1.0 | 0.6 | 1.0 | 1.1 |
| 10,9,8,7,12,11 | 1.2 | 0.7 | 1.6 | 1.0 | 0.8 |
| 10,8,11,7,9,12 | 0.9 | 0.9 | 1.0 | 1.0 | 0.8 |
| 9,8,12,10,7,11 | 1.8 | 1.4 | 3.1 | 1.1 | 1.0 |
| 11,9,10,8,12,7 | 1.4 | 0.9 | 3.0 | 1.1 | 0.8 |
| 10,12,11,8,7,9 | 2.0 | 1.8 | 2.3 | 1.1 | 1.0 |
| 8,9,11,7,12,10 | 1.2 | 1.6 | 0.7 | 1.0 | 1.1 |
| 9,12,8,7,10,11 | 0.7 | 0.7 | 0.7 | 1.1 | 0.9 |
| 9,8,11,7,10,12 | 0.6 | 0.8 | 0.4 | 1.0 | 0.0 |
| 12,8,10,7,9,11 | 0.8 | 0.7 | 1.2 | 1.2 | 0.7 |
| 10,12,9,8,7,11 | 0.8 | 0.8 | 0.7 | 1.0 | 0.8 |
| 8,11,10,7,9,12 | 1.0 | 1.2 | 0.5 | 1.0 | 1.0 |
| 9,8,10,11,12,7 | 0.8 | 1.2 | 0.5 | 1.1 | 1.1 |
| 12,9,11,8,7,10 | 0.6 | 0.6 | 0.5 | 1.2 | 1.1 |
| 12,8,11,10,7,9 | 0.9 | 0.8 | 1.5 | 1.2 | 0.7 |
| 9,12,7,8,11,10 | 0.8 | 1.4 | 0.6 | 1.1 | 1.1 |
| 11,9,8,12,10,7 | 3.5 | 0.6 | 11.3 | 1.1 | 0.7 |
| 10,11,9,7,8,12 | 0.7 | 0.9 | 0.7 | 1.1 | 0.8 |
| 8,10,11,7,9,12 | 0.6 | 1.0 | 0.4 | 1.0 | 0.0 |
| 12,7,9,11,8,10 | 0.5 | 0.6 | 0.6 | 1.2 | 0.9 |
| 9,11,12,10,8,7 | 0.7 | 1.2 | 0.8 | 1.0 | 0.7 |
| 12,7,9,8,10,11 | 1.0 | 1.0 | 0.9 | 1.2 | 0.8 |
| 11,12,8,7,9,10 | 0.8 | 0.8 | 0.9 | 1.1 | 0.9 |

FIG. 22-10

| Ligands combination | Cell counts (all) | Cell counts (Hes5$^+$) | Cell counts (Dcx$^+$) | Hes5-GFP | Dcx-RFP |
|---|---|---|---|---|---|
| 8,10,9,12,7,11 | 0.8 | 0.9 | 0.6 | 1.0 | 1.1 |
| 8,9,10,12,11,7 | 0.6 | 0.7 | 0.6 | 1.0 | 1.0 |
| 8,9,11,12,7,10 | 0.9 | 1.0 | 0.7 | 1.0 | 1.1 |
| 9,10,12,7,11,8 | 0.3 | 0.2 | 1.5 | 0.0 | 0.4 |
| 8,11,10,9,7,12 | 1.0 | 1.3 | 0.4 | 1.0 | 1.3 |
| 8,9,10,12,7,11 | 0.6 | 1.1 | 0.1 | 1.0 | 0.0 |
| 11,7,10,8,9,12 | 0.6 | 0.3 | 0.9 | 1.1 | 0.8 |
| 10,12,7,9,11,8 | 1.7 | 0.4 | 3.6 | 1.0 | 0.6 |
| 9,12,7,8,10,11 | 0.6 | 0.8 | 0.5 | 1.1 | 1.2 |
| 12,9,8,11,10,7 | 1.1 | 0.2 | 2.7 | 1.2 | 0.8 |
| 12,7,9,8,11,10 | 0.5 | 0.2 | 0.9 | 1.2 | 0.8 |
| 8,11,9,7,12,10 | 1.2 | 1.7 | 0.8 | 1.0 | 1.0 |
| 8,12,9,10,11,7 | 0.5 | 0.5 | 0.4 | 1.0 | 1.0 |
| 11,9,7,12,8,10 | 1.1 | 0.8 | 1.7 | 1.1 | 0.8 |
| 10,11,7,8,9,12 | 0.5 | 0.6 | 0.5 | 1.1 | 0.8 |
| 9,11,8,10,12,7 | 1.8 | 2.1 | 1.3 | 0.9 | 0.7 |
| 11,9,8,7,12,10 | 0.4 | 0.4 | 0.5 | 1.1 | 0.8 |
| 11,7,9,8,12,10 | 0.6 | 0.5 | 1.0 | 1.1 | 0.7 |
| 11,9,10,8,7,12 | 1.0 | 1.0 | 0.7 | 1.1 | 0.9 |
| 11,10,7,8,9,12 | 0.3 | 0.3 | 1.2 | 1.1 | 0.7 |
| 11,8,12,9,7,10 | 0.4 | 0.1 | 0.8 | 1.1 | 0.8 |
| 9,8,10,12,7,11 | 0.4 | 0.4 | 0.5 | 1.1 | 1.2 |
| 8,12,9,11,10,7 | 0.8 | 0.9 | 0.7 | 1.0 | 1.1 |
| 11,12,10,9,8,7 | 1.6 | 1.0 | 3.5 | 1.2 | 0.7 |
| 10,8,9,11,7,12 | 2.9 | 2.7 | 2.7 | 1.0 | 0.7 |
| 8,10,11,9,12,7 | 0.8 | 1.0 | 0.8 | 1.0 | 1.1 |
| 10,12,9,7,8,11 | 1.3 | 1.0 | 2.3 | 1.0 | 0.7 |
| 10,7,11,12,9,8 | 1.1 | 1.1 | 1.3 | 1.0 | 0.7 |
| 8,9,11,7,10,12 | 0.6 | 1.0 | 0.3 | 1.0 | 1.2 |
| 12,8,10,7,11,9 | 0.5 | 0.3 | 0.7 | 1.2 | 0.8 |
| 10,9,7,8,11,12 | 1.8 | 0.8 | 2.4 | 1.0 | 0.8 |
| 9,12,7,10,8,11 | 0.7 | 0.8 | 0.6 | 1.1 | 1.1 |
| 10,11,7,9,12,8 | 0.8 | 0.6 | 1.5 | 1.1 | 0.8 |
| 9,11,12,7,8,10 | 1.3 | 1.5 | 0.7 | 1.0 | 0.6 |
| 8,10,11,9,7,12 | 1.0 | 0.9 | 1.1 | 1.0 | 0.0 |
| 8,10,12,7,11,9 | 0.9 | 0.7 | 1.8 | 1.0 | 0.0 |
| 8,9,11,10,12,7 | 1.0 | 1.1 | 0.9 | 1.0 | 1.2 |
| 8,9,12,7,11,10 | 2.5 | 0.8 | 7.2 | 1.0 | 0.7 |
| 12,7,9,10,11,8 | 1.1 | 1.1 | 1.0 | 1.2 | 0.9 |
| 11,8,9,7,12,10 | 0.9 | 1.1 | 0.5 | 1.1 | 0.8 |
| 8,12,9,11,7,10 | 0.7 | 0.5 | 0.9 | 1.0 | 0.0 |
| 8,11,9,12,7,10 | 0.5 | 0.6 | 0.6 | 1.0 | 0.0 |

FIG. 22-11

| Ligands combination | Cell counts (all) | Cell counts (Hes5$^+$) | Cell counts (Dcx$^+$) | Hes5-GFP | Dcx-RFP |
|---|---|---|---|---|---|
| 11,12,9,10,8,7 | 1.6 | 1.3 | 1.9 | 1.2 | 0.8 |
| 11,12,7,9,8,10 | 1.9 | 1.9 | 1.2 | 1.1 | 1.0 |
| 8,10,12,7,9,11 | 0.7 | 0.8 | 0.6 | 1.0 | 1.1 |
| 9,10,8,12,11,7 | 0.9 | 0.4 | 0.9 | 0.0 | 0.9 |
| 9,10,8,12,7,11 | 0.5 | 0.4 | 0.5 | 0.0 | 0.9 |
| 9,8,11,7,12,10 | 1.0 | 1.5 | 0.4 | 1.0 | 0.0 |
| 12,9,10,11,8,7 | 1.2 | 1.3 | 0.4 | 1.2 | 0.0 |
| 9,8,11,10,12,7 | 0.7 | 0.7 | 0.7 | 1.0 | 1.0 |
| 8,11,10,9,12,7 | 0.9 | 0.7 | 1.1 | 1.0 | 1.0 |
| 10,12,7,9,8,11 | 1.4 | 2.9 | 1.1 | 1.0 | 0.6 |
| 12,9,7,10,8,11 | 0.6 | 0.7 | 0.4 | 1.2 | 1.0 |
| 12,9,10,11,7,8 | 1.8 | 2.7 | 1.1 | 1.2 | 0.8 |
| 11,10,8,9,12,7 | 1.1 | 1.3 | 0.7 | 1.1 | 0.9 |
| 9,10,8,11,12,7 | 1.6 | 0.8 | 2.4 | 0.0 | 0.7 |
| 12,7,11,9,8,10 | 1.3 | 1.0 | 2.8 | 1.2 | 0.9 |
| 11,8,10,7,9,12 | 1.2 | 1.2 | 1.0 | 1.1 | 0.8 |
| 8,12,10,11,7,9 | 0.7 | 0.6 | 0.8 | 1.0 | 1.0 |
| 11,7,9,12,10,8 | 1.1 | 1.4 | 0.8 | 1.1 | 0.8 |
| 9,10,8,11,7,12 | 1.0 | 0.1 | 1.9 | 0.0 | 0.8 |
| 9,7,10,8,11,12 | 1.4 | 1.6 | 1.3 | 1.0 | 1.1 |
| 11,7,10,8,12,9 | 0.8 | 0.9 | 0.6 | 1.1 | 0.7 |
| 9,10,8,7,11,12 | 0.4 | 0.2 | 0.8 | 0.0 | 0.7 |
| 11,10,9,12,8,7 | 0.7 | 0.8 | 0.7 | 1.1 | 0.8 |
| 8,10,9,11,12,7 | 0.8 | 0.6 | 1.2 | 1.0 | 0.6 |
| 12,9,8,11,7,10 | 0.4 | 0.4 | 0.7 | 1.2 | 0.9 |
| 12,8,9,10,11,7 | 1.5 | 0.8 | 3.0 | 1.2 | 0.6 |
| 11,7,9,10,12,8 | 1.5 | 1.4 | 1.3 | 1.1 | 0.7 |
| 9,10,8,7,12,11 | 2.1 | 0.2 | 4.6 | 0.0 | 0.6 |
| 11,12,7,9,10,8 | 0.6 | 0.3 | 0.7 | 1.1 | 0.8 |
| 11,9,10,7,12,8 | 1.7 | 1.7 | 1.9 | 1.1 | 0.7 |
| 11,9,8,10,12,7 | 1.2 | 0.7 | 1.9 | 1.1 | 0.7 |
| 11,7,12,8,9,10 | 0.7 | 1.0 | 0.5 | 1.1 | 0.5 |
| 11,12,10,7,9,8 | 1.3 | 0.3 | 2.4 | 1.2 | 0.7 |
| 11,10,12,7,8,9 | 1.1 | 0.8 | 1.0 | 1.1 | 0.8 |
| 11,8,12,7,10,9 | 1.5 | 1.0 | 2.6 | 1.1 | 0.8 |
| 10,8,12,9,11,7 | 0.9 | 0.8 | 1.3 | 1.0 | 0.6 |
| 11,8,9,10,7,12 | 0.8 | 1.2 | 0.6 | 1.1 | 0.6 |
| 9,10,7,12,8,11 | 2.5 | 0.2 | 6.1 | 0.0 | 0.8 |
| 10,12,8,7,9,11 | 0.8 | 0.9 | 0.9 | 1.0 | 0.6 |
| 9,11,10,7,8,12 | 1.2 | 1.0 | 2.7 | 1.0 | 0.6 |
| 9,10,7,11,12,8 | 0.7 | 0.6 | 1.5 | 1.1 | 0.5 |
| 12,9,11,7,8,10 | 0.8 | 0.4 | 4.0 | 1.2 | 0.7 |

FIG. 22-12

| Ligands combination | Cell counts (all) | Cell counts (Hes5+) | Cell counts (Dcx+) | Hes5-GFP | Dcx-RFP |
|---|---|---|---|---|---|
| 12,7,11,8,9,10 | 1.6 | 1.6 | 1.8 | 1.2 | 0.9 |
| 9,12,11,8,7,10 | 1.2 | 1.0 | 1.6 | 1.1 | 1.0 |
| 10,12,7,8,9,11 | 0.3 | 0.3 | 0.4 | 1.0 | 0.6 |
| 12,10,9,8,11,7 | 0.8 | 0.9 | 1.2 | 1.2 | 0.8 |
| 9,7,11,8,12,10 | 1.0 | 1.0 | 0.9 | 1.0 | 0.9 |
| 12,7,11,8,10,9 | 1.8 | 1.2 | 3.3 | 1.2 | 0.8 |
| 11,10,7,12,9,8 | 1.5 | 0.7 | 5.1 | 1.1 | 0.6 |
| 9,10,7,12,11,8 | 1.3 | 0.0 | 1.6 | 0.0 | 1.1 |
| 10,12,9,11,8,7 | 0.6 | 0.7 | 0.6 | 1.0 | 0.8 |
| 10,12,8,11,7,9 | 1.1 | 0.7 | 1.6 | 1.0 | 0.7 |
| 7,10,9,11,12,8 | 0.6 | 0.5 | 0.7 | 1.0 | 0.8 |
| 12,8,7,9,11,10 | 0.8 | 0.5 | 1.1 | 1.2 | 1.0 |
| 8,10,7,9,11,12 | 0.8 | 0.7 | 0.9 | 1.1 | 1.5 |
| 7,9,12,8,11,10 | 1.6 | 1.1 | 1.8 | 1.0 | 0.9 |
| 10,7,8,9,12,11 | 0.8 | 1.0 | 0.6 | 1.1 | 1.1 |
| 7,12,10,9,11,8 | 0.9 | 0.8 | 0.8 | 1.0 | 1.0 |
| 7,12,10,8,9,11 | 1.3 | 1.2 | 1.3 | 1.0 | 1.3 |
| 8,10,7,11,9,12 | 0.9 | 0.8 | 1.0 | 1.1 | 1.7 |
| 12,11,7,8,9,10 | 1.0 | 1.4 | 1.0 | 0.9 | 1.1 |
| 7,10,8,11,9,12 | 0.9 | 0.9 | 0.8 | 1.3 | 0.9 |
| 7,10,11,9,12,8 | 1.4 | 1.2 | 1.1 | 1.0 | 1.1 |
| 7,9,10,12,11,8 | 1.5 | 1.1 | 1.9 | 1.0 | 0.7 |
| 10,7,8,12,9,11 | 1.1 | 0.9 | 1.2 | 1.1 | 0.6 |
| 7,8,12,9,10,11 | 1.0 | 0.7 | 1.2 | 1.3 | 0.8 |
| 8,10,7,9,12,11 | 0.9 | 0.9 | 0.9 | 1.1 | 0.9 |
| 7,10,12,8,11,9 | 0.9 | 1.0 | 0.8 | 1.0 | 0.9 |
| 7,12,9,11,10,8 | 1.7 | 1.9 | 1.3 | 0.9 | 1.5 |
| 12,11,7,9,8,10 | 1.2 | 1.5 | 0.9 | 0.9 | 1.0 |
| 7,11,10,8,9,12 | 1.5 | 1.6 | 1.4 | 1.0 | 0.8 |
| 7,11,12,10,8,9 | 0.6 | 0.2 | 1.4 | 0.0 | 0.7 |
| 7,10,12,8,9,11 | 1.2 | 1.1 | 1.5 | 1.0 | 1.0 |
| 8,12,11,9,7,10 | 1.2 | 0.9 | 1.5 | 0.0 | 1.1 |
| 7,10,9,8,11,12 | 1.0 | 0.9 | 1.3 | 1.0 | 0.9 |
| 7,12,9,8,10,11 | 0.9 | 1.0 | 0.6 | 1.0 | 1.1 |
| 9,7,8,10,11,12 | 0.8 | 0.7 | 1.1 | 1.1 | 1.1 |
| 7,10,11,12,8,9 | 0.3 | 0.2 | 0.2 | 1.0 | 0.0 |
| 7,9,8,12,10,11 | 1.5 | 1.0 | 1.7 | 1.3 | 0.9 |
| 7,8,11,12,9,10 | 0.9 | 0.9 | 1.1 | 1.3 | 0.8 |
| 9,7,8,10,12,11 | 0.4 | 0.4 | 0.3 | 1.5 | 0.0 |
| 12,8,7,11,10,9 | 0.6 | 0.5 | 1.0 | 1.2 | 0.9 |
| 7,12,8,9,10,11 | 1.1 | 0.8 | 1.8 | 1.3 | 0.7 |
| 7,11,9,12,8,10 | 1.1 | 1.2 | 0.9 | 1.0 | 0.9 |

FIG. 22-13

| Ligands combination | Cell counts (all) | Cell counts (Hes5$^+$) | Cell counts (Dcx$^+$) | Hes5-GFP | Dcx-RFP |
|---|---|---|---|---|---|
| 8,11,7,12,10,9 | 0.7 | 0.3 | 0.8 | 1.1 | 1.0 |
| 8,9,7,11,12,10 | 0.6 | 0.3 | 1.0 | 1.5 | 1.0 |
| 11,8,7,9,12,10 | 0.8 | 0.8 | 0.8 | 2.1 | 3.1 |
| 9,8,7,11,10,12 | 0.7 | 0.4 | 1.2 | 1.6 | 1.2 |
| 12,8,7,11,9,10 | 0.7 | 0.9 | 0.6 | 3.7 | 2.9 |
| 12,8,7,10,9,11 | 1.6 | 2.4 | 1.0 | 2.9 | 2.4 |
| 12,7,8,9,11,10 | 3.0 | 2.1 | 6.0 | 1.2 | 1.0 |
| 7,10,8,12,11,9 | 0.5 | 0.4 | 0.6 | 1.3 | 1.1 |
| 7,8,10,11,9,12 | 1.4 | 3.0 | 0.1 | 1.3 | 0.0 |
| 12,11,8,7,10,9 | 1.3 | 1.1 | 1.2 | 0.9 | 1.0 |
| 7,11,12,10,9,8 | 0.1 | 0.1 | 0.3 | 0.0 | 0.0 |
| 12,11,8,10,7,9 | 1.8 | 2.2 | 1.2 | 0.9 | 0.6 |
| 7,8,12,10,9,11 | 0.4 | 0.3 | 0.5 | 1.3 | 0.7 |
| 12,11,8,7,9,10 | 0.5 | 0.5 | 0.6 | 1.3 | 0.7 |
| 8,11,7,9,10,12 | 0.3 | 0.3 | 0.3 | 1.5 | 1.2 |
| 7,9,12,10,8,11 | 1.3 | 1.9 | 1.0 | 1.0 | 1.1 |
| 11,7,8,10,9,12 | 1.8 | 2.0 | 1.4 | 1.1 | 1.0 |
| 7,9,8,11,10,12 | 0.3 | 0.3 | 0.4 | 1.3 | 1.0 |
| 7,11,8,9,10,12 | 0.9 | 1.0 | 0.9 | 1.1 | 1.0 |
| 7,8,9,12,10,11 | 0.6 | 0.3 | 1.1 | 1.3 | 0.8 |
| 7,10,11,9,8,12 | 0.3 | 0.2 | 0.4 | 0.0 | 2.3 |
| 12,11,8,9,7,10 | 0.3 | 0.3 | 0.3 | 1.3 | 0.9 |
| 7,8,12,10,11,9 | 0.8 | 0.8 | 0.8 | 1.1 | 1.1 |
| 10,8,7,12,9,11 | 0.3 | 0.1 | 0.8 | 1.6 | 0.9 |
| 8,7,11,12,10,9 | 0.5 | 0.3 | 1.1 | 1.4 | 0.8 |
| 7,12,10,8,11,9 | 2.4 | 1.7 | 3.2 | 1.0 | 0.8 |
| 7,9,11,12,10,8 | 1.2 | 1.2 | 1.1 | 1.0 | 0.9 |
| 7,8,10,12,11,9 | 0.4 | 0.2 | 0.5 | 1.3 | 1.0 |
| 10,7,8,11,9,12 | 0.9 | 0.8 | 0.9 | 1.1 | 1.1 |
| 7,12,9,8,11,10 | 1.9 | 1.3 | 3.6 | 1.0 | 0.6 |
| 8,7,12,9,10,11 | 1.0 | 1.0 | 1.1 | 1.1 | 0.8 |
| 7,10,11,12,9,8 | 0.9 | 0.8 | 0.9 | 1.0 | 1.1 |
| 11,8,7,10,9,12 | 0.3 | 0.2 | 0.5 | 1.9 | 1.5 |
| 8,7,12,9,11,10 | 0.3 | 0.2 | 0.4 | 1.4 | 1.0 |
| 7,12,9,10,11,8 | 1.2 | 1.4 | 0.5 | 1.0 | 1.9 |
| 7,11,9,8,10,12 | 1.1 | 1.1 | 1.2 | 1.0 | 1.0 |
| 8,10,7,11,12,9 | 0.4 | 0.3 | 1.0 | 1.5 | 1.0 |
| 8,7,9,12,10,11 | 0.6 | 0.4 | 1.3 | 1.4 | 0.7 |
| 8,9,7,11,10,12 | 0.7 | 0.7 | 0.8 | 1.1 | 1.0 |
| 7,10,9,12,8,11 | 1.3 | 1.7 | 1.2 | 1.0 | 1.1 |
| 7,10,11,8,9,12 | 0.2 | 0.0 | 0.4 | 0.0 | 0.9 |
| 7,10,12,11,9,8 | 1.3 | 2.0 | 1.1 | 1.0 | 1.1 |

FIG. 22-14

| Ligands combination | Cell counts (all) | Cell counts (Hes5+) | Cell counts (Dcx+) | Hes5-GFP | Dcx-RFP |
|---|---|---|---|---|---|
| 7,12,9,11,8,10 | 1.7 | 1.1 | 2.3 | 1.0 | 1.0 |
| 12,11,7,9,10,8 | 1.4 | 1.9 | 1.2 | 0.9 | 0.9 |
| 7,9,11,10,8,12 | 1.8 | 1.5 | 1.8 | 1.0 | 1.1 |
| 7,9,11,8,12,10 | 1.9 | 1.8 | 1.7 | 1.0 | 1.1 |
| 7,9,12,10,11,8 | 1.1 | 1.0 | 1.0 | 1.0 | 1.1 |
| 7,10,11,8,12,9 | 1.2 | 1.2 | 1.2 | 1.0 | 1.0 |
| 7,9,11,12,8,10 | 1.3 | 1.3 | 1.3 | 1.0 | 0.9 |
| 7,9,11,8,10,12 | 1.2 | 1.3 | 1.5 | 1.0 | 1.1 |
| 7,9,12,11,8,10 | 1.1 | 1.1 | 1.2 | 1.0 | 0.8 |
| 8,11,7,9,12,10 | 0.8 | 1.0 | 0.4 | 1.5 | 1.4 |
| 7,11,8,12,10,9 | 0.9 | 0.2 | 1.6 | 1.4 | 0.8 |
| 12,11,10,7,8,9 | 0.9 | 0.9 | 0.7 | 1.3 | 1.2 |
| 12,11,10,7,9,8 | 0.7 | 0.5 | 0.9 | 1.3 | 0.8 |
| 9,7,12,11,10,8 | 0.6 | 0.5 | 0.9 | 1.0 | 0.9 |
| 7,9,11,10,12,8 | 1.0 | 1.1 | 1.0 | 1.0 | 1.1 |
| 7,12,10,9,8,11 | 0.9 | 1.0 | 0.8 | 1.0 | 0.9 |
| 8,12,11,7,9,10 | 0.5 | 0.4 | 0.6 | 1.0 | 0.7 |
| 7,11,10,8,12,9 | 0.6 | 0.4 | 0.6 | 1.0 | 0.7 |
| 12,11,8,9,10,7 | 1.1 | 1.0 | 1.3 | 1.1 | 1.0 |
| 8,12,11,10,9,7 | 0.2 | 0.2 | 0.0 | 0.0 | 0.0 |
| 8,12,11,10,7,9 | 0.2 | 0.0 | 0.4 | 0.0 | 0.0 |
| 8,12,11,7,10,9 | 0.1 | 0.0 | 0.5 | 0.0 | 0.0 |
| 11,7,8,10,12,9 | 0.9 | 0.6 | 1.3 | 1.8 | 1.6 |
| 12,7,8,10,11,9 | 0.9 | 1.4 | 0.6 | 2.4 | 1.6 |
| 7,12,11,8,10,9 | 1.1 | 1.4 | 0.1 | 0.9 | 0.0 |
| 7,9,8,10,11,12 | 1.4 | 1.1 | 1.7 | 1.1 | 0.9 |
| 7,8,11,10,12,9 | 1.2 | 1.1 | 1.2 | 1.1 | 0.8 |
| 7,12,11,10,9,8 | 1.6 | 2.0 | 0.9 | 0.9 | 0.9 |
| 8,11,7,10,12,9 | 1.4 | 1.0 | 1.3 | 1.1 | 1.0 |
| 8,7,11,9,10,12 | 0.9 | 0.5 | 0.9 | 1.1 | 1.4 |
| 8,10,7,12,9,11 | 0.2 | 0.2 | 0.1 | 1.5 | 1.3 |
| 8,7,9,11,10,12 | 0.2 | 0.2 | 0.2 | 1.4 | 0.8 |
| 8,7,11,9,12,10 | 1.3 | 1.4 | 1.2 | 1.1 | 0.9 |
| 11,8,7,12,9,10 | 0.3 | 0.2 | 0.3 | 2.0 | 2.3 |
| 7,10,8,11,12,9 | 0.5 | 0.2 | 1.0 | 1.3 | 0.8 |
| 8,12,7,11,10,9 | 1.4 | 1.5 | 1.1 | 1.1 | 1.1 |
| 7,11,8,10,9,12 | 1.2 | 1.1 | 1.0 | 1.1 | 1.0 |
| 7,10,9,11,8,12 | 1.1 | 0.0 | 2.3 | 0.0 | 0.8 |
| 12,7,8,11,9,10 | 1.3 | 1.1 | 1.5 | 1.2 | 0.7 |
| 8,11,7,12,9,10 | 0.6 | 0.4 | 0.8 | 1.5 | 1.2 |
| 12,11,10,8,9,7 | 0.3 | 0.2 | 0.8 | 1.3 | 0.7 |
| 8,7,9,12,11,10 | 0.6 | 0.7 | 0.4 | 1.1 | 0.0 |

FIG. 22-15

| Ligands combination | Cell counts (all) | Cell counts (Hes5$^+$) | Cell counts (Dcx$^+$) | Hes5-GFP | Dcx-RFP |
|---|---|---|---|---|---|
| 10,8,7,11,12,9 | 1.1 | 1.2 | 0.9 | 1.1 | 1.0 |
| 7,10,12,11,8,9 | 0.8 | 1.0 | 0.6 | 1.0 | 1.8 |
| 8,7,9,10,11,12 | 1.0 | 1.3 | 0.7 | 1.1 | 1.1 |
| 7,10,12,9,11,8 | 3.1 | 3.7 | 2.4 | 1.0 | 1.0 |
| 10,7,8,9,11,12 | 0.7 | 0.6 | 0.7 | 1.1 | 1.2 |
| 12,11,8,10,9,7 | 0.5 | 0.3 | 0.6 | 1.3 | 0.9 |
| 9,8,7,11,12,10 | 0.9 | 0.8 | 1.1 | 1.1 | 1.0 |
| 9,7,8,12,10,11 | 1.0 | 1.2 | 0.8 | 1.1 | 1.1 |
| 7,10,9,8,12,11 | 2.1 | 1.7 | 2.0 | 1.0 | 1.1 |
| 7,8,12,11,10,9 | 0.5 | 0.4 | 0.7 | 1.3 | 0.8 |
| 7,8,9,10,11,12 | 1.1 | 1.0 | 1.2 | 1.1 | 1.0 |
| 7,8,10,12,9,11 | 1.1 | 1.0 | 1.2 | 1.1 | 0.9 |
| 7,11,9,8,12,10 | 2.2 | 1.7 | 1.9 | 1.0 | 1.0 |
| 11,7,8,9,12,10 | 0.3 | 0.3 | 0.5 | 1.8 | 1.7 |
| 11,7,8,12,9,10 | 0.3 | 0.2 | 0.4 | 1.8 | 1.0 |
| 7,8,9,12,11,10 | 1.2 | 1.0 | 1.0 | 1.1 | 1.2 |
| 12,11,9,8,7,10 | 0.4 | 0.3 | 0.7 | 1.3 | 1.1 |
| 7,8,11,9,12,10 | 1.7 | 1.0 | 2.3 | 1.1 | 1.1 |
| 7,12,11,8,9,10 | 1.2 | 1.0 | 1.2 | 0.9 | 1.2 |
| 7,8,11,12,10,9 | 1.3 | 1.5 | 1.1 | 1.1 | 1.4 |
| 11,7,8,9,10,12 | 0.6 | 0.3 | 0.8 | 1.1 | 0.7 |
| 7,10,9,12,11,8 | 1.3 | 2.0 | 0.9 | 1.0 | 1.1 |
| 7,12,10,11,9,8 | 2.4 | 3.2 | 1.8 | 1.0 | 0.7 |
| 7,11,10,9,8,12 | 0.8 | 1.9 | 0.7 | 0.0 | 1.3 |
| 7,12,11,9,10,8 | 0.8 | 1.1 | 0.6 | 0.9 | 0.0 |
| 7,11,10,9,12,8 | 0.4 | 0.8 | 0.3 | 0.0 | 0.0 |
| 7,11,10,12,8,9 | 0.9 | 0.7 | 1.2 | 1.0 | 0.6 |
| 7,11,12,9,8,10 | 1.0 | 1.0 | 0.8 | 1.0 | 1.1 |
| 7,9,10,8,11,12 | 0.9 | 0.8 | 0.9 | 1.0 | 1.1 |
| 7,12,11,9,8,10 | 1.2 | 1.1 | 1.4 | 0.9 | 0.8 |
| 7,10,12,9,8,11 | 0.8 | 0.8 | 0.8 | 1.0 | 1.0 |
| 9,8,7,10,12,11 | 0.8 | 1.4 | 0.3 | 1.6 | 0.0 |
| 12,11,10,9,7,8 | 1.3 | 1.0 | 1.4 | 1.1 | 1.0 |
| 8,7,10,9,11,12 | 2.9 | 1.9 | 4.6 | 1.1 | 0.7 |
| 12,11,9,10,8,7 | 1.0 | 0.6 | 1.8 | 1.1 | 1.0 |
| 7,11,12,9,10,8 | 0.9 | 0.5 | 1.4 | 1.0 | 1.5 |
| 7,11,10,12,9,8 | 1.0 | 0.0 | 2.2 | 0.0 | 1.0 |
| 12,7,8,11,10,9 | 0.4 | 0.3 | 0.7 | 2.2 | 2.0 |
| 7,11,9,10,8,12 | 0.7 | 0.6 | 0.5 | 0.0 | 1.2 |
| 12,8,7,9,10,11 | 4.7 | 2.9 | 5.9 | 3.7 | 2.6 |
| 11,8,7,9,10,12 | 1.8 | 1.5 | 2.4 | 2.1 | 1.3 |
| 8,7,11,12,9,10 | 0.6 | 1.3 | 0.3 | 1.1 | 1.4 |

FIG. 22-16

| Ligands combination | Cell counts (all) | Cell counts (Hes5+) | Cell counts (Dcx+) | Hes5-GFP | Dcx-RFP |
|---|---|---|---|---|---|
| 7,9,12,11,10,8 | 8.0 | 12.8 | 5.4 | 1.0 | 0.3 |
| 8,7,10,12,11,9 | 0.7 | 0.9 | 0.6 | 1.1 | 1.0 |
| 7,11,9,10,12,8 | 1.0 | 0.5 | 1.3 | 0.0 | 1.0 |
| 8,12,7,10,9,11 | 0.9 | 0.7 | 1.0 | 1.4 | 1.4 |
| 10,8,7,9,11,12 | 0.9 | 0.9 | 0.9 | 1.1 | 1.0 |
| 9,7,8,12,11,10 | 0.9 | 0.8 | 0.9 | 1.1 | 1.0 |
| 7,9,8,10,12,11 | 0.6 | 0.4 | 0.9 | 1.3 | 0.8 |
| 10,7,8,12,11,9 | 1.3 | 1.3 | 1.3 | 1.1 | 1.1 |
| 8,7,12,11,9,10 | 0.4 | 0.3 | 0.4 | 1.4 | 0.8 |
| 7,11,8,12,9,10 | 0.2 | 0.3 | 0.1 | 1.4 | 0.0 |
| 12,7,8,10,9,11 | 0.9 | 1.4 | 0.4 | 1.2 | 1.1 |
| 8,7,10,11,12,9 | 0.6 | 0.6 | 0.6 | 1.1 | 1.0 |
| 9,7,8,11,10,12 | 0.4 | 0.4 | 0.3 | 1.5 | 1.4 |
| 12,11,9,7,10,8 | 0.4 | 0.3 | 0.7 | 1.3 | 0.8 |
| 12,8,7,10,11,9 | 1.1 | 0.7 | 1.4 | 1.2 | 1.0 |
| 12,7,8,9,10,11 | 0.9 | 0.6 | 1.2 | 1.2 | 1.0 |
| 8,7,9,11,12,10 | 0.2 | 0.2 | 0.3 | 1.4 | 0.8 |
| 8,7,12,10,11,9 | 0.6 | 0.4 | 1.2 | 1.4 | 0.7 |
| 7,12,8,10,9,11 | 0.6 | 0.8 | 0.4 | 1.3 | 0.9 |
| 10,8,7,11,9,12 | 0.7 | 0.6 | 0.6 | 1.1 | 1.0 |
| 7,8,9,11,12,10 | 0.9 | 1.0 | 0.7 | 1.1 | 1.1 |
| 7,8,12,9,11,10 | 0.8 | 0.5 | 1.1 | 1.3 | 0.8 |
| 8,7,12,10,9,11 | 1.2 | 1.3 | 1.0 | 1.1 | 1.0 |
| 7,10,8,9,11,12 | 1.0 | 1.2 | 1.0 | 1.1 | 1.0 |
| 7,8,10,11,12,9 | 0.4 | 0.5 | 0.4 | 1.3 | 1.2 |
| 8,12,7,10,11,9 | 0.3 | 0.3 | 0.2 | 1.4 | 1.2 |
| 7,8,10,9,12,11 | 0.4 | 0.4 | 0.3 | 1.3 | 1.0 |
| 8,12,7,9,11,10 | 1.1 | 1.1 | 1.0 | 1.1 | 1.1 |
| 7,11,9,12,10,8 | 0.8 | 0.8 | 0.6 | 1.0 | 1.1 |
| 7,9,10,12,8,11 | 1.2 | 1.5 | 0.9 | 1.0 | 1.0 |
| 7,12,10,11,8,9 | 1.1 | 1.1 | 0.9 | 1.0 | 1.2 |
| 8,9,7,12,10,11 | 0.6 | 0.5 | 0.6 | 1.1 | 1.3 |
| 7,9,10,8,12,11 | 1.1 | 1.2 | 1.3 | 1.0 | 1.1 |
| 9,7,12,8,10,11 | 1.5 | 0.5 | 3.2 | 1.0 | 0.8 |
| 7,11,12,8,9,10 | 0.7 | 0.8 | 0.6 | 0.0 | 0.9 |
| 9,7,11,12,8,10 | 1.2 | 1.8 | 0.7 | 1.0 | 1.0 |
| 8,9,7,10,12,11 | 1.2 | 1.5 | 0.6 | 1.4 | 0.9 |
| 9,8,7,12,10,11 | 0.8 | 0.9 | 0.9 | 1.6 | 0.6 |
| 10,8,7,9,12,11 | 1.0 | 1.0 | 1.0 | 1.1 | 1.0 |
| 8,11,7,10,9,12 | 0.4 | 0.2 | 1.2 | 1.5 | 0.8 |
| 11,8,7,10,12,9 | 0.8 | 0.7 | 1.4 | 1.1 | 0.0 |
| 11,7,8,12,10,9 | 0.9 | 1.1 | 0.8 | 1.1 | 1.0 |

FIG. 22-17

| Ligands combination | Cell counts (all) | Cell counts (Hes5+) | Cell counts (Dcx+) | Hes5-GFP | Dcx-RFP |
|---|---|---|---|---|---|
| 7,11,12,8,10,9 | 0.4 | 0.4 | 0.4 | 0.0 | 0.0 |
| 11,8,7,12,10,9 | 0.4 | 0.3 | 0.7 | 2.0 | 2.4 |
| 12,11,10,9,8,7 | 1.2 | 2.2 | 0.8 | 1.1 | 1.0 |
| 8,7,9,10,12,11 | 0.7 | 0.9 | 0.4 | 1.4 | 1.1 |
| 7,12,8,11,10,9 | 0.5 | 0.5 | 0.5 | 1.3 | 1.0 |
| 7,8,10,9,11,12 | 1.1 | 1.1 | 1.2 | 1.1 | 0.9 |
| 7,9,10,11,12,8 | 1.8 | 3.7 | 1.5 | 1.0 | 1.3 |
| 7,12,8,10,11,9 | 1.1 | 1.0 | 1.6 | 1.1 | 1.0 |
| 7,11,8,9,12,10 | 0.5 | 0.4 | 0.7 | 1.4 | 0.8 |
| 7,9,8,12,11,10 | 1.0 | 1.4 | 0.6 | 1.1 | 1.0 |
| 7,11,8,10,12,9 | 0.8 | 0.8 | 0.8 | 1.1 | 0.0 |
| 8,7,10,9,12,11 | 0.9 | 0.8 | 0.8 | 1.1 | 1.1 |
| 8,9,7,12,11,10 | 0.6 | 0.4 | 1.1 | 1.5 | 0.7 |
| 8,7,12,11,10,9 | 1.0 | 0.8 | 1.1 | 1.4 | 0.8 |
| 7,12,8,9,11,10 | 2.6 | 1.3 | 5.0 | 1.3 | 0.6 |
| 12,11,9,8,10,7 | 0.8 | 0.5 | 1.1 | 1.3 | 1.0 |
| 7,8,12,11,9,10 | 0.9 | 1.2 | 0.9 | 1.1 | 0.7 |
| 10,7,8,11,12,9 | 0.5 | 0.8 | 0.2 | 1.6 | 0.0 |
| 8,10,7,12,11,9 | 0.4 | 0.3 | 0.6 | 1.5 | 0.8 |
| 7,8,11,9,10,12 | 0.6 | 0.4 | 0.9 | 1.3 | 0.8 |
| 8,7,10,11,9,12 | 1.0 | 0.6 | 2.1 | 1.4 | 0.7 |
| 8,12,7,11,9,10 | 0.6 | 0.5 | 0.6 | 1.1 | 0.0 |
| 8,7,11,10,9,12 | 0.9 | 0.8 | 1.4 | 1.1 | 1.0 |
| 7,8,11,10,9,12 | 0.5 | 0.8 | 0.1 | 1.1 | 0.0 |
| 12,11,10,8,7,9 | 0.7 | 0.5 | 0.9 | 1.3 | 0.8 |
| 9,7,11,12,10,8 | 1.1 | 1.2 | 1.0 | 1.0 | 1.1 |
| 8,9,7,10,11,12 | 0.8 | 1.0 | 0.5 | 1.1 | 0.0 |
| 8,7,11,10,12,9 | 1.1 | 1.1 | 1.8 | 1.1 | 0.9 |
| 7,12,8,11,9,10 | 1.5 | 1.4 | 3.9 | 1.1 | 0.7 |
| 8,7,10,12,9,11 | 0.6 | 0.5 | 0.9 | 1.4 | 0.7 |
| 7,9,8,11,12,10 | 1.0 | 0.4 | 1.6 | 1.3 | 0.7 |
| 9,7,12,8,11,10 | 0.9 | 1.2 | 0.8 | 1.0 | 1.1 |
| 12,11,9,7,8,10 | 0.7 | 0.4 | 1.3 | 1.3 | 0.8 |
| 9,7,12,11,8,10 | 1.0 | 1.2 | 0.8 | 1.0 | 1.1 |
| 7,10,8,9,12,11 | 0.5 | 0.8 | 0.3 | 1.1 | 1.3 |
| 7,8,9,10,12,11 | 1.2 | 1.7 | 0.4 | 1.1 | 0.0 |
| 9,7,8,11,12,10 | 0.7 | 0.9 | 0.4 | 1.1 | 0.0 |
| 7,9,12,8,10,11 | 0.5 | 0.3 | 0.7 | 0.0 | 1.1 |
| 10,8,7,12,11,9 | 0.9 | 0.6 | 2.4 | 1.6 | 0.6 |
| 12,11,9,10,7,8 | 1.9 | 1.9 | 1.7 | 1.3 | 1.0 |
| 9,8,7,12,11,10 | 0.8 | 0.6 | 1.6 | 1.6 | 0.8 |
| 8,12,7,9,10,11 | 0.3 | 0.3 | 0.2 | 1.1 | 1.2 |

FIG. 22-18

| Ligands combination | Cell counts (all) | Cell counts (Hes5$^+$) | Cell counts (Dcx$^+$) | Hes5-GFP | Dcx-RFP |
|---|---|---|---|---|---|
| 7,10,8,12,9,11 | 0.8 | 0.9 | 0.6 | 1.1 | 1.2 |
| 7,8,9,11,10,12 | 0.2 | 0.3 | 0.1 | 1.1 | 0.0 |
| 7,12,9,10,8,11 | 0.7 | 0.4 | 0.9 | 0.0 | 1.0 |
| 7,12,11,10,8,9 | 1.7 | 2.0 | 1.8 | 0.9 | 1.0 |
| 9,8,7,10,11,12 | 0.8 | 1.2 | 0.7 | 1.1 | 1.2 |
| 7,9,10,11,8,12 | 2.5 | 0.2 | 6.1 | 0.0 | 0.8 |

FIG. 23-1

| Ligands combination | Cell counts (all) | Cell counts (Hes5$^+$) | Cell counts (Dcx$^+$) | Hes5-GFP | Dcx-RFP |
|---|---|---|---|---|---|
| Micro-environment containing 1 ligand | | | | | |
| 7 | 1.4 | 1.5 | 1 | 1 | 1.1 |
| 8 | 1.6 | 1.6 | 0.9 | 1 | 1 |
| 9 | 1.4 | 1.5 | 0.6 | 1 | 1 |
| 10 | 2.3 | 2.5 | 1 | 0.9 | 1 |
| 11 | 1.5 | 1.7 | 1 | 1 | 1 |
| 12 | 1.6 | 2 | 1 | 2.5 | 0.8 |
| Micro-environment containing 2 ligands | | | | | |
| 7,8 | 0.7 | 1.0 | 0.8 | 0.7 | 1.3 |
| 7,9 | 0.5 | 0.5 | 0.5 | 0.9 | 1.0 |
| 7,11 | 1.0 | 1.0 | 1.0 | 0.7 | 1.0 |
| 8,9 | 2.5 | 2.3 | 1.0 | 0.9 | 1.0 |
| 8,11 | 1.8 | 1.0 | 2.0 | 0.7 | 1.0 |
| 9,11 | 0.6 | 1.0 | 0.7 | 0.8 | 0.7 |
| 8,12 | 1.4 | 1.3 | 2.0 | 1.2 | 1.0 |
| 7,12 | 1.3 | 1.0 | 1.5 | 1.2 | 1.0 |
| 9,12 | 1.3 | 1.8 | 1.1 | 1.2 | 1.0 |
| 10,12 | 2.0 | 2.1 | 1.8 | 1.3 | 1.0 |
| 11,12 | 1.2 | 0.8 | 1.5 | 1.3 | 1.1 |
| 7,10 | 2.5 | 2.0 | 2.0 | 1.0 | 1.0 |
| 8,10 | 1.6 | 2.3 | 1.8 | 1.0 | 0.7 |
| 9,10 | 3.1 | 2.1 | 2.3 | 1.0 | 1.0 |
| 10,11 | 2.3 | 1.7 | 1.8 | 1.0 | 0.8 |
| Micro-environment containing 3 ligands | | | | | |
| 7,9,11 | 1.0 | 0.3 | 1.1 | 1.0 | 1.0 |
| 7,9,10 | 1.0 | 2.0 | 0.7 | 1.0 | 0.5 |
| 7,8,12 | 1.0 | 0.7 | 1.2 | 0.9 | 1.5 |
| 7,8,11 | 1.0 | 1.0 | 1.0 | 1.2 | 1.0 |
| 7,9,12 | 1.0 | 1.0 | 1.0 | 1.2 | 1.0 |
| 7,11,12 | 1.8 | 2.0 | 1.5 | 1.1 | 1.0 |
| 8,9,11 | 1.0 | 1.0 | 1.0 | 1.0 | 1.0 |
| 8,9,12 | 1.0 | 1.0 | 1.0 | 0.6 | 0.7 |
| 8,11,12 | 1.0 | 1.0 | 1.0 | 0.6 | 1.0 |
| 9,11,12 | 1.0 | 1.3 | 0.7 | 1.0 | 1.0 |
| 7,8,10 | 2.0 | 2.0 | 1.6 | 1.0 | 0.7 |
| 7,8,9 | 2.1 | 2.7 | 1.4 | 1.0 | 1.0 |
| 7,10,12 | 2.0 | 1.0 | 3.0 | 1.2 | 1.0 |

FIG. 23-2

| Ligands combination | Cell counts (all) | Cell counts (Hes5$^+$) | Cell counts (Dcx$^+$) | Hes5-GFP | Dcx-RFP |
|---|---|---|---|---|---|
| 8,10,12 | 1.8 | 1.3 | 2.0 | 1.1 | 2.0 |
| 7,10,11 | 2.0 | 2.0 | 0.2 | 0.9 | 0.6 |
| 8,10,11 | 1.4 | 1.0 | 1.4 | 1.2 | 0.7 |
| 8,9,10 | 1.6 | 1.8 | 1.3 | 1.0 | 1.0 |
| 9,10,11 | 1.6 | 1.9 | 1.8 | 1.0 | 1.0 |
| 9,10,12 | 1.4 | 1.2 | 1.6 | 1.2 | 1.0 |
| 10,11,12 | 1.6 | 1.6 | 1.4 | 1.0 | 1.0 |
| Micro-environment containing 4 ligands | | | | | |
| 7,9,10,12 | 1.5 | 2.2 | 0.8 | 1.2 | 1 |
| 7,8,10,12 | 1 | 1 | 1 | 1 | 1 |
| 7,9,10,11 | 1.4 | 1.7 | 1 | 1 | 1 |
| 7,8,10,11 | 0.43 | 0.57 | 0.13 | 1.2 | 1 |
| 9,10,11,12 | 1 | 1 | 1 | 1.11 | 1 |
| 8,10,11,12 | 2.3 | 3.33 | 1 | 0.83 | 1 |
| 8,9,11,12 | 1 | 1 | 1 | 0.8 | 1 |
| 8,9,10,12 | 1 | 1 | 1 | 1 | 1 |
| 8,9,10,11 | 1.8 | 2 | 1 | 0.95 | 1 |
| 7,10,11,12 | 0.7 | 0.3 | 1 | 0.8 | 0.8 |
| 7,9,11,12 | 1.6 | 1.6 | 1 | 1 | 1 |
| 7,8,11,12 | 0.6 | 0.4 | 0.5 | 1.2 | 1 |
| 7,8,9,12 | 1 | 0.6 | 1 | 1.11 | 1 |
| 7,8,9,11 | 1.25 | 1.2 | 1 | 1.3 | 1 |
| 7,8,9,10 | 2 | 2 | 1.5 | 1.11 | 1 |
| Micro-environment containing 5 ligands | | | | | |
| 8,9,10,11,12 | 1 | 1 | 1 | 1 | 0.92 |
| 7,8,9,10,12 | 1.3 | 1.3 | 0.9 | 1.1 | 1 |
| 7,8,10,11,12 | 1 | 1 | 1 | 1.2 | 1 |
| 7,8,9,10,11 | 1.4 | 1.67 | 1.4 | 1.2 | 1 |
| 7,9,10,11,12 | 1 | 1 | 1 | 1.17 | 0.7 |
| 7,8,9,11,12 | 1 | 1 | 1 | 1.2 | 1 |

FIG. 24

| Ligand at day 1 | Ligand at day 2 | Ligand at day 3 | Ratio of means before and after addition of last ligand | P value from permutation test | Color code |
|---|---|---|---|---|---|
| Jagged | — | — | 0.8876917 | 1e-04 | Red |
| Jagged | CXCL | — | 0.7200305 | 9e-04 | Red |
| DLL | — | — | 1.016565 | 0.2848 | Black |
| DLL | Jagged | — | 1.135468 | 7e-04 | Green |
| DLL | EGF | Jagged | 1.184278 | 0.0021 | Green |
| DLL | PACAP | Jagged | 1.185485 | 0.0023 | Green |
| DLL | CXCL | Jagged | 1.228948 | 7e-04 | Green |
| DLL | PDGF | — | 0.8241267 | 0.0014 | Red |
| DLL | PDGF | Jagged | 1.359624 | 0.0058 | Green |
| EGF | — | — | 0.8147452 | 1e-05 | Red |
| EGF | PACAP | — | 0.2041974 | 1e-05 | Red |
| PACAP | — | — | 0.9867764 | 0.318 | Black |
| PACAP | DLL | Jagged | 1.202267 | 0.0088 | Green |
| CXCL | — | — | 1.10504 | 2e-04 | Green |
| CXCL | DLL | — | 1.097629 | 0.0095 | Green |
| CXCL | DLL | Jagged | 1.444677 | 5e-04 | Green |
| PDGF | — | — | 1.189182 | 1e-05 | Green |
| PDGF | DLL | — | 1.156782 | 0.0172 | Green |
| PDGF | DLL | Jagged | 1.580939 | 0.0099 | Green |

FIG. 25

| Ligand at day 1 | Ligand at day 2 | Ligand at day 3 | Ratio of means before and after addition of last ligand | P value from permutation test | Color code |
|---|---|---|---|---|---|
| Jagged | — | — | 1.122089 | 0.0208 | Green |
| DLL | — | — | 0.9096058 | 0.0435 | Red |
| PDGF | — | — | 0.8631499 | 0.0031 | Red |
| EGF | — | — | 0.9380446 | 0.1326 | Black |
| Jagged | EGF | — | 1.376171 | 0.0205 | Green |
| CXCL | EGF | — | 1.194729 | 0.0488 | Green |
| CXCL | — | — | 1.001191 | 0.4672 | Black |
| EGF | CXCL | — | 1.201566 | 0.0317 | Green |
| DLL | PDGF | CXCL | 0.6177589 | 0.0463 | Red |
| PACAP | — | — | 1.16592 | 0.0045 | Green |
| PDGF | PACAP | — | 0.7940869 | 0.0465 | Red |

UNIVERSAL MICROFLUIDIC CULTURE SYSTEM TO ANALYZE AND CONTROL CELL DYNAMICS

CROSS-REFERENCE TO RELATED APPLICATIONS

This application is a national phase application under 35 U.S.C. § 371 of International Application No. PCT/US2018/032727 filed May 15, 2018, which claims the benefit of priority of U.S. Provisional Patent Application No. 62/506,362 filed May 15, 2017, all of which are hereby incorporated by reference in their entirety.

FIELD OF INVENTION

The present disclosure relates generally to microfluidics; and, more particularly, but not by way of limitation, to improved microfluidic devices, systems, and methods.

BACKGROUND

Cells reside and operate in highly dynamic microenvironments, where the type and concentration of signaling molecules are ever changing. For example, the stem cell niche consists of a range of signaling molecules and growth factors allowing maintenance of the stem cell pool, but during development or injury the composition of the niche rapidly changes to allow differentiation into different lineages. Immune cells operate in tissue and mature in specialized microenvironments in the lymph nodes or the thymus, and infection leads to a wholescale modulation of these environments and the chemical signals therein. It is highly desirable to recapitulate such dynamic signaling environments in vitro, for the quantitative study of underlying phenomena as well as applications in stem cell therapy, tissue regeneration and immunotherapy. Traditional dish-and-pipette techniques are quite limited in creating and studying such a dynamical microenvironment, and manipulation and quantitation of single live cells is very challenging with such traditional tools.

The advances in biomedical research often follow the steps of development in tools and methodologies. In this regard, microfluidic cell culture and analysis technologies like organ-on-a-chip and high-throughput cell arrays convert previously time-consuming and labor-intensive lab tasks into a series of streamlined, mostly automatic operations through intellectual design principles (Klein, et al., 2015), and some devices allow previously impractical experiments (Jeong, et al., 2015). A common pitfall, however, lies in the emergence of large numbers of microfluidic devices with each carrying distinct and tailor-made features to meet specific needs (Occhetta, et al., 2015; Sarioglu, et al., 2015; Cao, et al. 2015). Few microfluidic systems attempt at bringing together the capabilities necessary for the study of signaling dynamics at the single-cell level. As primary cells are sensitive to environmental conditions such as shear flow and spatial confinement, chip-to-chip variations will likely bring undesired artifacts. Thus, a microfluidic chip that is capable of creating a large number of parallel conditions while exerting minimal effect on cellular micro-environment is of high demand and utility. Many microfluidic culture devices were demonstrated in the past, with varying success in the cultivation of already robust cell lines, however demonstrations of viable microfluidic culture of sensitive primary mammalian cells are far and few between.

Another challenge associated with studies on cellular dynamics is the reconstruction of complicated and dynamic cellular environments in vitro (Kolch, et al., 2015; Kellogg, et al., 2015). Cells constantly receive and process time-varying signals such as local concentration changes of pathogens or stress-related molecules. Dynamic inputs include the simultaneous presence of multiple participating ligands (combinatorial inputs), as well as the temporal presence of ligands one after another (sequential inputs; Judge, et al., 2005). Characterizing how cells respond to such dynamic inputs can not only help to elucidate the regulatory mechanisms underlying fundamental cellular processes, but also to pave the way towards developing therapeutics through organ-on-a-chip approaches.

SUMMARY

Dynamical control of the cellular microenvironment is highly desired for the study of stem cells, immunology, and cancer. The inventors present a high-throughput automated microfluidic system for culture, differentiation and analysis of cells in precisely defined dynamic microenvironments, mimicking signaling in vivo. In certain embodiments, this system delivers complex chemical signals to 1500 independently programmable 2-D cultures and 3-D organoids, and dynamically stimulates both adherent and non-adherent cells while tracking single cells with video microscopy. Cells can be stained in situ, or retrieved for analysis or expansion. The inventors investigated stem cell and immune signaling dynamics with single-cell resolution, and demonstrated the importance of stimulation order in developing brain tissue. This system constitutes a universal culture platform overcoming limitations of microfluidic cell culture and greatly enhancing its capabilities, allowing the study of previously unattainable aspects of cellular dynamics and enabling accelerated biological discovery.

To address the limitations described above in the Background and to bring in much needed new capabilities in cell manipulation and control, the inventors developed an automated microfluidic culture system and the associated integrated experimental platform (hardware and software) that allows multi-mode cell culture and stimulation, rapid on-chip mixing for the generation of diverse dynamic chemical inputs, as well as containing, in certain embodiments, 1,500 individually-addressable culturing units for high-throughput biomedical studies. Coupled with customized software for chip control and data processing, the system can perform programmed delivery of formulated fluids to any designated on-chip culture unit while monitoring and analyzing corresponding cellular responses. The microfluidic chip described herein is a useful platform for both fundamental and translational biomedical studies on cell signaling, drug screening and personalized medicine. The present experiments using embryonic neuronal stem cells (NSCs) demonstrate that information on NSCs proliferation and its cellular status, assessed via the expression level of self-renewal and differentiation markers Hes5 and Doublecortin (Dcx), in response to dynamic inputs can be acquired by simultaneous imaging and analyzing, in certain embodiments, 1,500 conditions. These studies mimic the effect of changing ligand conditions in the in vivo cellular environments, and reveal that the NSCs development can be regulated through time-dependent expression pattern of participating ligands.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially" and "approximately" may be substituted with "within [a percentage] of" what is specified, where the percentage includes 0.1, 1, 5, and 10 percent.

Further, an apparatus or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments are described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIGS. 1A-1E depict an example of a multi-functional, high-throughput microfluidic chip with capacities to generate complex inputs for biomedical studies. In the example shown, the microfluidic device contains 1,500 independently programmable culture chambers. During a 1-week experiment, the device performs nearly $10^6$ pipetting steps to create and maintain distinct culture conditions in each of the chambers.

FIG. 1A conceptually illustrates complex and dynamic inputs that the present system enables to be delivered to each chamber. For example, each chamber can execute a distinct dynamic culture program (combinations, timed sequences, sine waves, etc.) where the fluidic composition can be changed when desired, and dynamic processes (i.e. NF-κB localization or Hes5 expression) are tracked with single-cell resolution. In the depicted example, an on-chip nanoliter multiplexer measures several fluids, and mixes them at predetermined ratios to create complex chemical inputs; and a peristaltic pump can deliver inputs to any given one of the chambers. For the combinatorial input scenario, several chemicals are mixed and delivered to the cells continuously. In sequential inputs, signaling molecules are changed with a programmed time interval ($\Delta t=1$ day).

FIG. 1B depicts an optical image of the chip containing 1,500 individually-addressable cell culture chambers loaded with orange dye in the flow layer and blue dye in the control layer. Certain key features of this chip example are enlarged: (1) the multiplexer module; (2) a peristaltic pump equipped with 8 parallel flow channels (100 μm in width) in which fluid is driven by 3 control lines (200 um in width); and (3) shear-free cell culture chambers. The system can culture adherent or non-adherent cells in either suspension mode, in monolayer populations, or in 3-D format using hydrogels. The novel two-layer geometry of the culture chambers allows diffusion-based media delivery to create a stable environment for cells, and provides the additional ability of single-cell tracking of even non-adherent cells during dynamical stimulation.

FIG. 1C-1 depicts a schematic view of each of the individual cell culture chambers, composed of a buffering layer (75 μm in height) and a deeper culture unit (150 μm in height). The two-layer cell chamber design allows diffusion-based or flow-based media delivery, 3D cell culture, immobilization of non-adherent cells by gravity, and automated cell retrieval.

FIG. 1C-2 depicts numerical simulations of flow profile through the culture chamber. In the cell-loading and stimulation (flow) mode above, the bottom of the chamber experiences rather mild shear stress at 1 mm/sec flow rate. At the same flow rate in the feeding mode below, the flow velocity at the bottom of the cell culture chamber remain zero, when flow is directed through the buffering chamber (below). Fluid mechanical simulations indicate the flow-rates for diffusion-based media delivery and cell retrieval via direct flow.

FIG. 1C-3 depicts schematic drawings (top row) and optical images (bottom row) of three distinct flow modes: (1) fluid is directed to flow over the culture chamber directly (cell loading and stimulation mode); (2) fluid is guided through the buffering region from the side (feeding mode); and (3) fluid can be directed to totally bypass the chamber unit to, for example, avoid cross-contamination or perform other fluid manipulation. As shown, each chamber is controlled by a network of dedicated channels and membrane valves that automate various cell culture procedures.

FIG. 1D conceptually illustrates that cells can be immunostained in the chip. The control system is integrated to a fluorescent microscope and can automatically track individual cells in time-lapse experiments. Single cells or populations of interest can be automatically retrieved from individual chambers for off-chip analysis or expansion.

FIG. 1E depict primary cells (e.g. mouse NSCs, human HSCs) and cell lines (e.g. Jurkat T-cells, mouse fibroblasts) that have been viably cultured and maintained on-chip for weeks. Growth rates are equal or better than the well-plate culture are achieved through frequent diffusion-based media delivery while maintaining an unperturbed microenvironment.

FIG. 2A schematically illustrate automated operation of the depicted example of the universal microfluidic system. Utilizing advantageous features of the chip example of FIGS. 1A-1E, complicated and dynamic inputs (up to 1500) can be generated and maintained on chip; shear-fee 3D chamber geometry allows multi-mode culture of cell-lines and primary cells; customized MATLAB program make possible the high-throughput studies of temporal and combinatorial variations in microenvironments.

FIG. 2B depict examples of information including cell morphology, protein expression and immunofluorescence level that can be obtained through single cell tracking and on-chip immunostaining.

FIG. 3A depicts single-cell response to TNF-alpha stimulation at 0.1 ng/ml (top) and 0.2 ng/ml (bottom). In this experiment, TNF-alpha is introduced to the designated cell culture chambers and maintained for 2 hours as a pulse every 24 hours. 3T3 cell response to pulse stimulations is marked by triangles in cell images in the lower panel.

FIG. 3B depicts TNF-alpha induced dosage-dependent human HSCs' death on chip. Cells were cultured on the microfluidic device in the absence of TNF-alpha (control) and 1 ng/ml TNF-alpha for up to 5 days.

FIG. 4A depicts time-lapse Bright-field (top) and epifluorescence (GFP, bottom) images of Hes5-GFP NSCs in adherent culture on chip. The time is marked at the lower right corner of each upper image (in hours).

FIG. 4B depicts Bright field, and fluorescence images showing the growth of Hes5-GFP NSCs neurosphere in an uncoated culture chamber.

FIG. 4C depicts NSCs maintained in 3D hydrogel. The corresponding growth curves for both sphere and 3D hydrogel culture are shown in the right panel.

FIGS. 5A and 5B depict variations in NSCs in Hes5-GFP and Dcx-RFP levels, respectively. Rectangular bars and solid lines represent the average and the standard deviation of all cells housed within the same chamber. individual dots represent values obtained from each single cells. Experimental conditions are listed in the x-axis. Corresponding NSCs images are shown in FIG. 5C, FIG. 14, and FIG. 15.

FIG. 5C depicts selected bright-field and fluorescent images of NSCs cells on 1st day and 6th day with selected combinatorial inputs: (1) Jagged and DLL; (4) Jagged, DLL, EGF, PACAP and CXCL; (5) Jagged and EGF; (8) Jagged, EGF and PDGF. The images are marked according to the order presented in FIGS. 5A and 5B.

FIG. 6A depicts time-lapse bright field (top) and epifluorescence (bottom) images of NSCs cultured with 100 ng/ml PDGF. Scale bars in all images denote 100 μm.

FIG. 6B depicts a histogram of Hes5-GFP expression in NSCs before (red) and after (black) one week culture with 100 ng/ml PDGF. High levels of Hes5 in NSCs indicate maintenance of stem cell state, while reduced Hes5 indicates progress towards differentiation.

FIG. 6C depicts an enlarged bright field (top) and corresponding epifluorescence (bottom) images of NSCs cultured on chip with 100 ng/mL PDGF. Selected cells were indicated by arrows and individually tracked over 40 hours during on chip culture.

FIG. 6D depicts lineage tracing (top) and Hes5-GFP expression level (bottom) for the 3 selected cells in Figure C. Distinct proliferation patterns were observed in spite of similar Hes5-GFP level.

FIG. 6E shows examples of quantitative analysis of mouse NSCs growth and Hes5 expression in different culture conditions. Each culture contains either a single ligand or a mixture of ligands that are highly expressed in developing mouse brain, including PDGF, CXCL, PACAP, EGF, Jagged, or DLL. Overall, NSCs proliferate at different rates depending on initial cell seeding density, with higher densities leading to higher proliferation rates. Hes5 expression rate and variability in single NSC cells significantly depend on signaling molecules present in culture chambers.

FIG. 7A depicts the trajectories of NSCs maintained and stimulated in a culture chamber with a 2D+time spatiotemporal visualization (time runs along the vertical axis).

FIG. 7B depicts enlarged bright field images of NSCs cultured on chip in the media containing (from left to right) 1000 ng/ml CXCL, 50 ng/mL PDGF and 100 nM PACAP. The scale bars are 50 μm in all images.

FIG. 7C depicts immunostaining images of NSCs exposed to (top row to bottom) 50 ng/mL PDGF, 1000 ng/ml CXCL and 100 nM PACAP. Markers for determining NSCs differentiation states are Hes5, Sox10, Pax6 and beta-tubulin. Insertions in the top row are selected NSCs cells with distinct morphology.

FIG. 7D depicts a schematic drawing of NSCs differentiation determined by Hes5 and Dcx expression level, and cell morphology.

FIGS. 8A-8E illustrate features of high-throughput analysis of NSC dynamics reveals logic rules in differentiation.

FIG. 8A depicts stimulations of NSCs in two types of experiments: During Combinatorial Stimulation, microfluidic device delivered all possible combinations of DLL, EGF, Jagged, PACAP, CXCL and PDGF to distinct culture chambers, and maintained these conditions for 6 days. During Sequential Stimulation, the device changed the molecule type each day during the 6-day experiment. Cell numbers and single-cell Hes5-GFP expression was recorded in each chamber during the experiment.

FIG. 8B depicts example data sets from one experiment. Signal induced NSCs cell count change (top) and Hes5-GFP expression (low) at day-6 are plotted as color maps, together with the color-coded bars indicating the combinatorial and sequential signal inputs.

FIG. 8C (including 8C-1, 8C-2) depict the overall effect of individual ligands on NSCs self-renewal and differentiation in various stimulation contexts is shown in the table on top row. In single ligand stimulation experiments, cells were stimulated with only one ligand and cell numbers and Hes5 levels are recorded. In combinatorial and sequential stimulation experiments, the ligand of interest is present in a complex mixture of other ligands, and the inventors identify its overall effect by averaging over groups of experiments. In the middle row, the dynamic variations in cell number and Hes5 level are plotted against 6 days of time for single ligands, combinatorial and sequential experiments. The lowest row shows the effect of a given ligand (PDGF) on cell numbers or Hes5 level in experiments that contain other ligands.

FIG. 8D (including 8D-1, 8D-2) illustrates decision tree analysis of Hes5 expression and cell proliferation under sequential stimulation reveals cellular logic rules for NSC differentiation and self-renewal. Each node contains mean value of target variable and number of remaining samples (n). Below each node, there is a decision attribute for the splitting test and the consequences of the test ("Yes" or "No") are written. For example, "PDGF day 1=NO" is short for "PDGF is not added at day 1".

FIG. 8E depicts schematic drawings of the ligand input sequences discovered by decision tree analysis leading to differentiation (triangle) or self-renewal (square) are presented in the upper panel. All routes are color-coded with the solid lines representing routes obtained from Hes5 expression data, and dashed lines for NSCs proliferation data. In the middle panel, various input routes and associated increase (green) or decrease (red) of Hes5 expression and NSCs proliferation are shown. In the lower panel, the inventors show list of the most significant nontrivial logical rules identified through classification tree analysis.

FIGS. 9A-9H summarize signaling principles in neural stem cell differentiation and self-maintenance, uncovered by dynamical single-cell culture and decision tree analysis.

FIG. 9A depicts the dynamic changes in cell number and Hes5 level are plotted for two ligand combinations containing (DLL, EGF, PDGF) or (Jagged, EGF, PDGF). Dots are single cell values and dashed line indicates population mean. NSCs are directed to either self-renewal (high Hes5) or differentiation (low Hes5) by changing only one ligand within the combination.

FIG. 9B depicts a comparison of two distinct sequential inputs highlights the importance of input sequence and timing in stem cell differentiation. The cells in both experiments received all six ligands in different orders. Changing the order of a single ligand (e.g. EGF from day2 to day6) directs NSCs to distinct cell fate.

FIG. 9C shows that a decision-tree analysis reveals the optimal route of signal input sequence leading to NSCs self-renewal (highest cell numbers with high Hes5 level). The optimal route is shown in the middle.

FIG. 9D shows that synergy and antagonism of signal ligands emerges as another principle. The combination of any 2 ligands may lead to either enhanced (synergistic) or reduced (antagonistic) effect compared to experiments that use these ligands in isolation.

FIG. 9E illustrates that cells show strong commitment at various decision points towards either differentiation or self-renewal, and ignore the signals that come after the decision point. On top, the inventors show the hypothetical scenario where cells ignore remaining signal sequences if they already received the right sequence of A>>B>>C for commitment to self-renewal, and B>>A>>D for commitment to differentiation. At the middle and lowest rows, the inventors present the actual input sequences that indicate strong commitment for self-renewal and differentiation, which were discovered by decision-tree analysis.

FIG. 9F shows that the ligands can act bi-directionally, and the exact role of a given signaling molecule is determined by either timing of that molecule, or by its pre-conditions.

FIG. 9G shows that increasing environmental complexity (number of participating ligands) suppresses NSC proliferation, however reducing the complexity enhances the stem cell pool. Including more ligands in experiments led to a reduction of the proliferation rate, while the Hes5 level remained relatively unchanged. Error bars indicate variability of individual experiments from the mean.

FIG. 9H illustrates that the existence of multiple combinatorial and sequential input conditions leading to the same cell fate (similar Hes5 level and cell numbers) suggests redundancy in stem cell pathways.

FIG. 10A depicts real-time fluorescent images of 3T3 cells during stimulation with 0.1 and 0.5 ng/ml TNF-alpha 2-hour pulse. Red arrows indicate responsive cells.

FIG. 10B depicts a fraction of activated 3T3 cell at various TNF-alpha concentrations. Dilutions of TNF-alpha are performed through pipetting (blue circles), and on-chip dilution using peristaltic pumps (red circles).

FIGS. 10C and 10D present single cells response to TNF-alpha stimulation at 0.2 ng/ml and 0.1 ng/ml concentration, respectively.

FIG. 11A depicts the culture of Jurkat cells in suspension mode.

FIG. 11B(I) depicts the culture of mice HSCs cells in suspension mode, and (II) depicts the differentiation of mice HSCs cells by introducing M-CSF differentiation media.

FIG. 12A depicts an NSCs sphere culture on chip for 5 days.

FIG. 12B depicts an NSCs sphere retrieved after 5 days of culture on chip, followed by loading into laminin-coated 96-well plate for adherent culture.

FIGS. 13A-13C depict tables listing combinatorial and sequential inputs composed by 6 signaling ligands, including Jagged-1, DLL-1, EGF, PACAP, CXCL and PDGF-AA.

FIG. 16A depicts the fraction of activated 3T3 cell at various TNF-alpha concentrations. Dilutions of TNF-alpha are performed through pipetting (blue circles), and on-chip dilution using peristaltic pumps (lighter circles).

FIG. 16B depicts single-cell NF-κB nuclear localization traces for active and non-activated cells. The blue traces show non-activated cells while the black curves show the activated cells.

FIG. 16C depicts activation time of population and isolated single 3T3 cells at 0.1, 0.2 and 0.5 ng/ml TNF concentration.

FIG. 16D depicts fluorescence images and NF-κB nuclear localization traces of isolated single 3T3 cells showing oscillation following the first stimulation at 0.2 ng/ml concentration.

FIG. 16E depicts single-cell NF-κB nuclear localization traces for 3T3 cells in micro-environments with sinusoidal and pulse TNF modulation. The maximum TNF concentration is 5 ng/ml in both cases. The sinusoidal signal is created by modulating the real-time TNF concentration through on-chip mixing, while the digital TNF pulses are provided by replacing each culture chamber with flash culture medium following 15-min TNF pulses.

FIG. 16F depicts real-time fluorescent images of 3T3 cells during sinusoidal and pulse TNF stimulation.

FIGS. 18A and 18B show how decision tree analysis reveals cellular logic rules for NSCs' differentiation and self-renewal. Each node, represented by a colored box, contains mean value of target variable (mean) and number of remaining samples (n). The nodes are filled with color gradients from red to green according to the reported mean value. Below each node, there is a decision attribute for the splitting test and the consequences of the test ("Yes" or "No") are written along arcs between a parent node and its children nodes. For example, "PACAP day 1=NO" is short for "PACAP is not added at day 1", and "PDGF=NO" is short for "PDGF is not present".

FIG. 18A depicts a decision tree built on NSCs' proliferation under combinatorial stimulation.

FIG. 18B depicts a Decision tree built on NSCs' Hes5-GFP expression under combinatorial stimulation.

FIG. 22 depicts a table listing ways in which micro-environments can be exposed to 6 ligands in a sequential manner. For one experiment performed by the inventors, the order of the ligands in the table of FIG. 22 represents the order of ligands introduced into the micro-environments on daily bases. Number 7 denotes Jagged; 8 DLL; 9 EGF; 10 PACAP; 11 CXCL; 12 PDGF.

FIG. 23 depicts another table listing ways in which micro-environments can be exposed to 6 ligands in a combinatorial manner, containing 2 to 5 ligands in each condition. Number 7 denotes Jagged; 8 DLL; 9 EGF; 10 PACAP; 11 CXCL; 12 PDGF.

FIG. 24 depicts another table for which a one-tailed permutation test is used to examine statistical significance of biological findings under sequential input of Hes5-GFP expression measurement. Green: $p<0.05$ and relative increase of means >5%, Red: $p<0.05$ and relative decrease of means >5%, Black: no significant difference.

FIG. 25 depicts another table for which a one-tailed permutation test is used to examine statistical significance of biological findings under sequential input of NSCs proliferation measurement. Green: $p<0.05$ and relative increase of means >5%, Red: $p<0.05$ and relative decrease of means >5%, Black: no significant difference.

RESULTS

Versatile, Multi-Functional Microchamber for Viable Culture and Dynamic Stimulation of a Wide Range of Cell Types The inventors designed a microfluidic cell culture chamber to cultivate all types of eukaryotic cells and to model and understand the role of a complex and ever-changing cellular microenvironment in biological processes. To accomplish this feat, precise control of environmental parameters such as cell density, surface properties, fluidic exchange, media and growth factor delivery, and humidity are preferred. Microfluidic devices integrated with membrane valves have been previously employed for high-throughput biomedical studies, because they allow automated generation of well-controlled programmable conditions mimicking micro-environments in vivo (Luni, et al., 2016; Lecault, et al., 2011;

Tay, et al., 2010). Despite the advantages of integrated microfluidics in cell culture, long-term culture of sensitive cell types like primary cells has been a major challenge, and the throughput of achievable independent culture conditions remain limited to less than a hundred in a single device (Gomez, et al., 2007). Furthermore, dynamic chemical stimulation of weakly adherent or non-adherent cells has not been possible when single-cell tracking and analysis is required, as exposing cells to flow would disturb the positions of the cells preventing single cell tracking. To address these limitations, the inventors designed a microfluidic chamber geometry and associated devices for the studies of various biological samples, and tested its robustness in creating consistent micro-environmental conditions for long-term cellular studies while exerting minimum-to-none disturbance on the system. This 3-D chamber geometry consists of two separate sub-chambers (culture chamber and buffer chamber) dedicated to cell culture and media flow, and a set of orthogonal supply channels that allow feeding and stimulating non-adherent cells via diffusion, substantially preventing cells from flow (FIG. 1D). The diffusion time for signaling molecules from the loading chamber to the cell chamber is, in certain embodiments, less than a minute, allowing rapid saturation of the cell channel signaling molecules. This enables delivery of a wide range of dynamic signaling inputs to the cells in the culture chamber with minimal distortion of the signal shape. By using diffusion feeding in this simple 2-layer chamber geometry, the inventors satisfied the seemingly contradictory requirements of dynamic stimulation and single-cell tracking in live-cell imaging experiments.

Figure 2A:
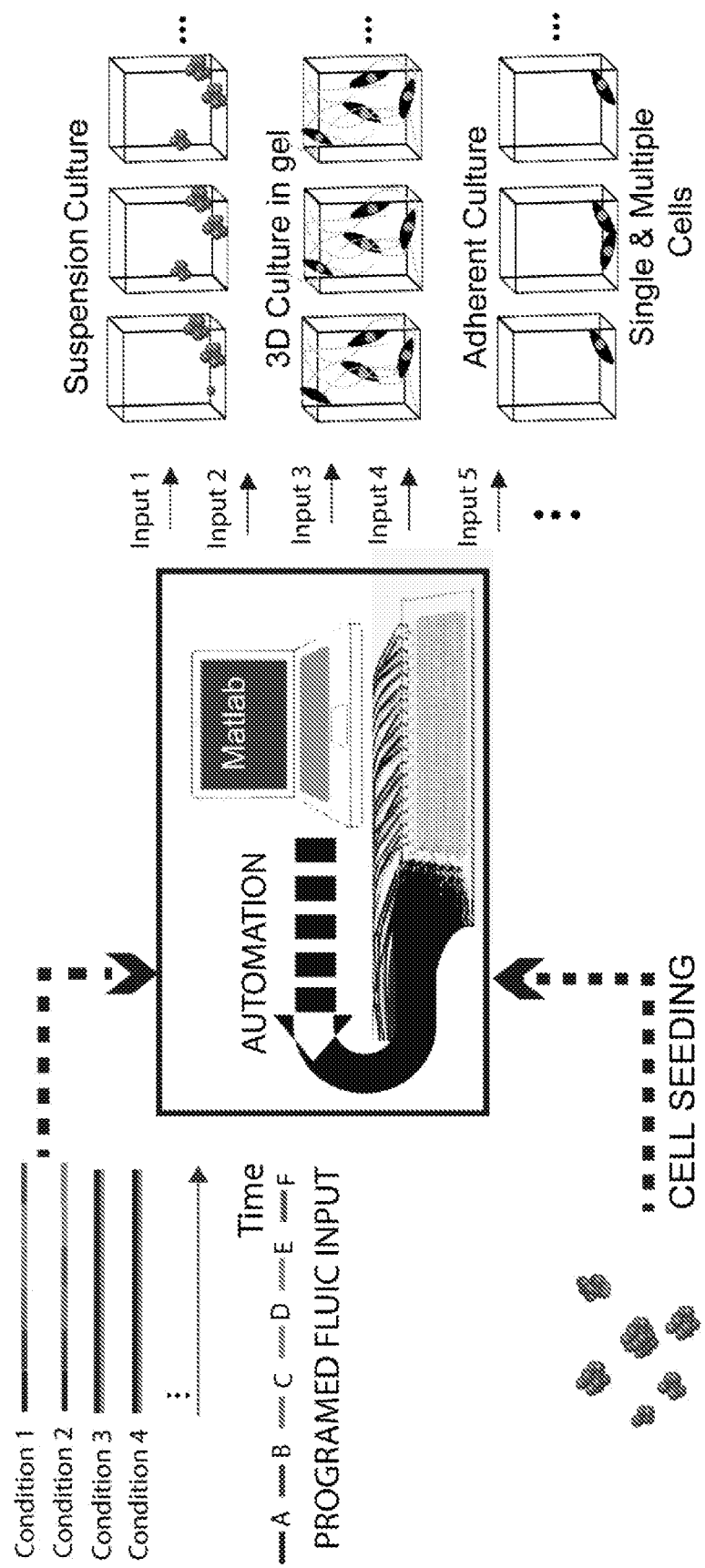
FIGS. 2A-2B depict aspects of an example of an automated microfluidic system for multimode cell culture and data analysis.
Figure 2B:
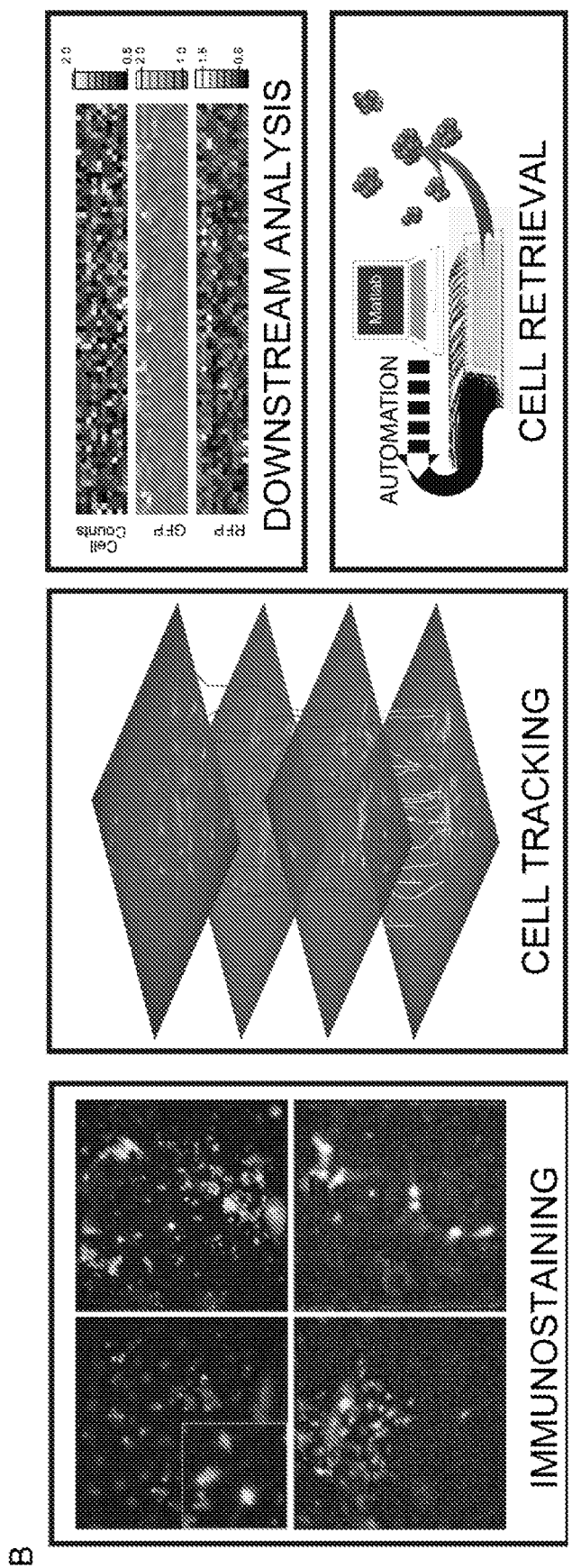

The deep, well-like structure of the culture chamber allows loading and immobilizing cells by gravity, and, in certain embodiments, enables growing cells into three-dimensional (3-D) colonies such as neuronal organoids. In certain embodiments, the cell culture chamber can be loaded with hydrogels and other matrices to enable 3-D organization of cells, and cells can still be stimulated by providing signaling molecules through the buffer chamber, which then diffuse through the gel (FIG. 2A). Furthermore, one of the supply channels can be used to retrieve the cells from the chamber and ultimately from the microfluidic device at the end of stimulation and imaging, by simply increasing the flow rate in this channel (FIG. 2B). These capabilities provide seamless and automated loading, feeding, culture, stimulation, single cell tracking, and retrieval of both adherent and non-adherent cell types maintained in isolation, as 2-D cultures or as 3-D organoids.

It was found that gently providing a constant supply of fresh media to the cultured cells is crucial for their viability in microfluidic environments. Due to increased surface-to-volume ratio in a nanoliter sized chamber, in certain situations, water evaporation is a major problem that increases salt concentration and easily kills the cells. Due to the large volume of media the system can supply to the buffer chamber, and by eliminating flow from the culture chamber, many important culture parameters such as the humidity, $CO_2$ and cell-secreted factors can be, in certain embodiments, maintained constant without the need for a separate media bath in the present device (Lecault, et al., 2011). In certain embodiments, elimination of the membrane separated media bath simplifies the chamber design, allowing us to parallelize such chambers and build thousands of them in a single device.

Figure 1B:
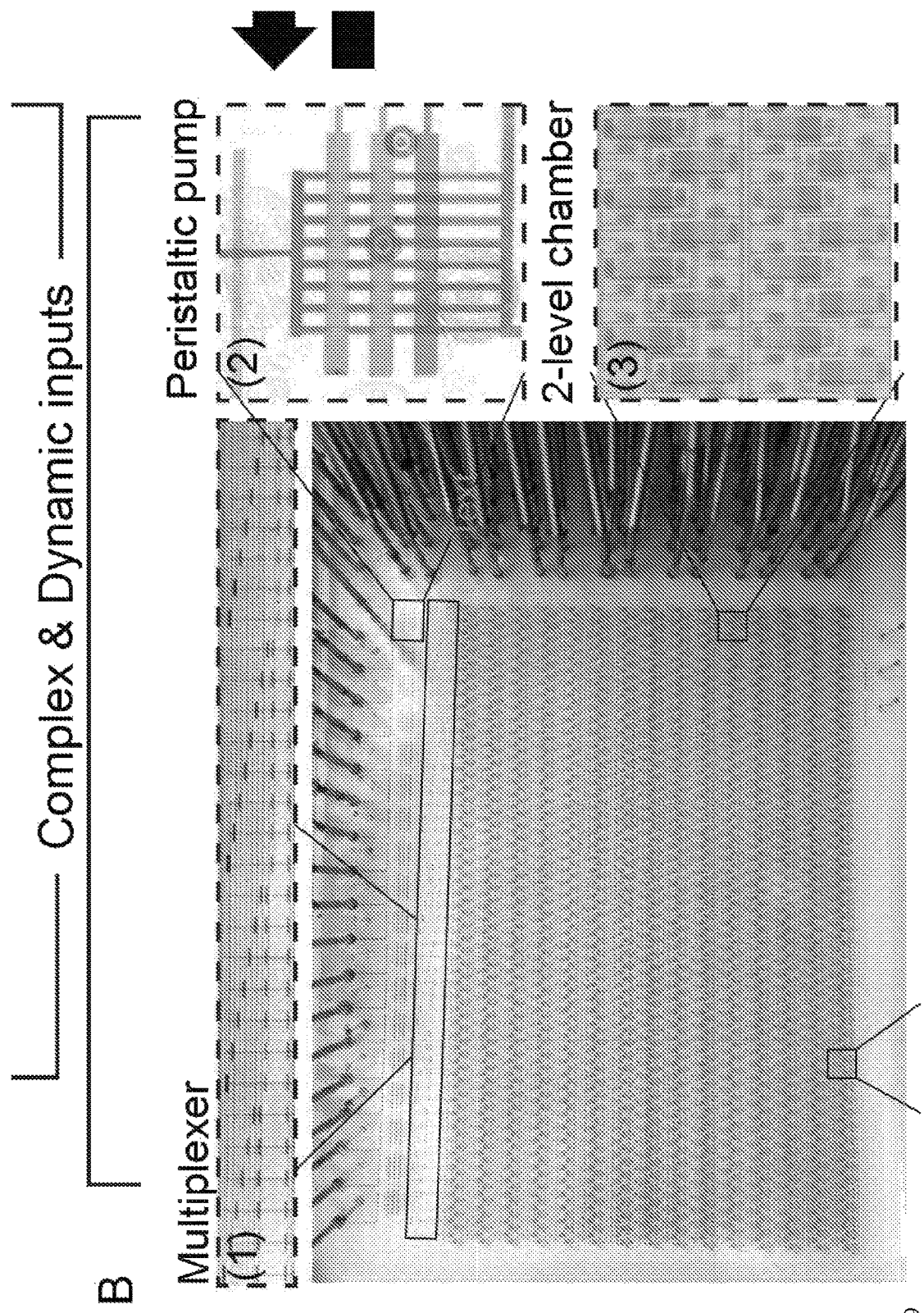
Figures 1, 1C, 2:
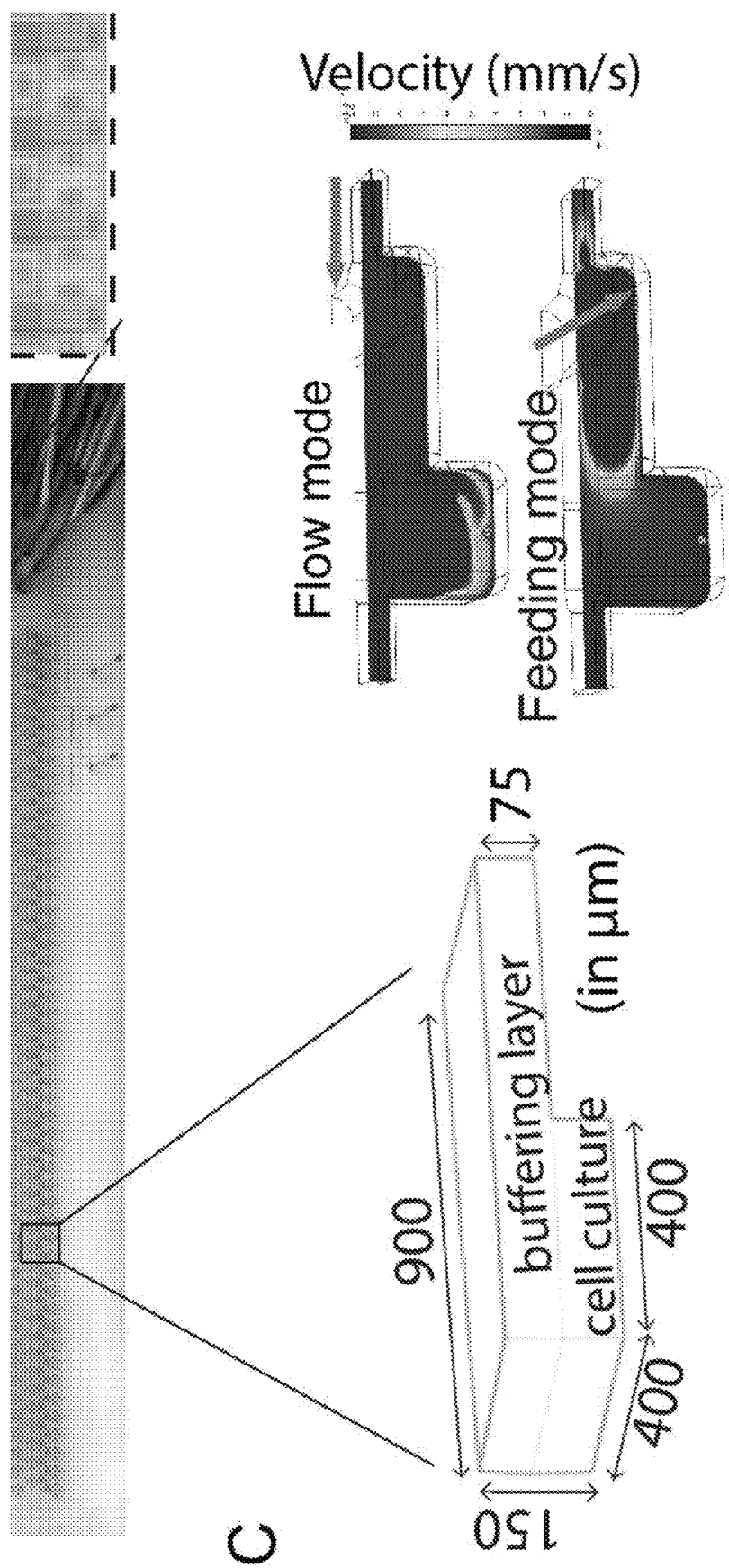
Figures 1, 1C, 2, 3:
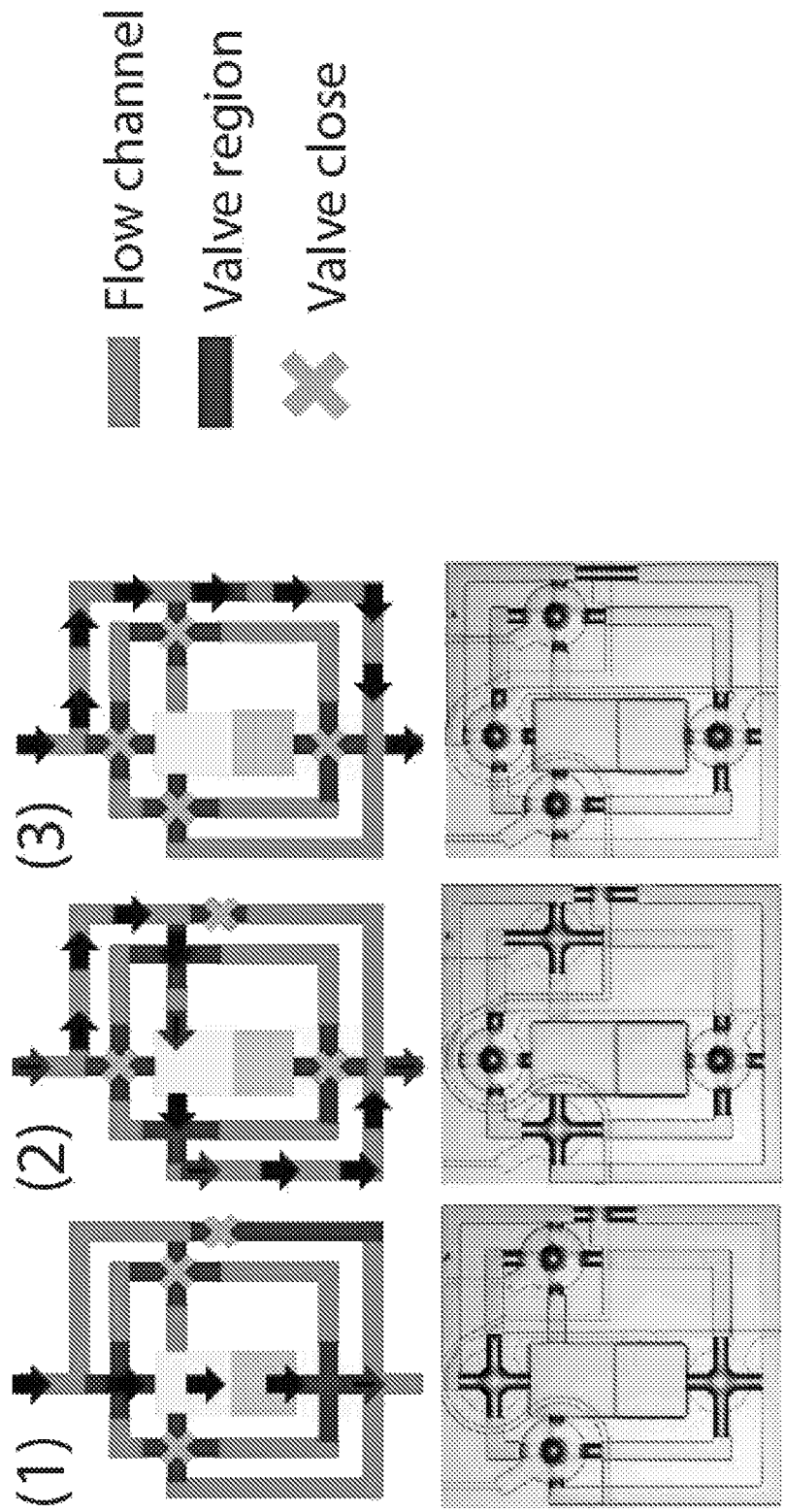
Figure 1D:
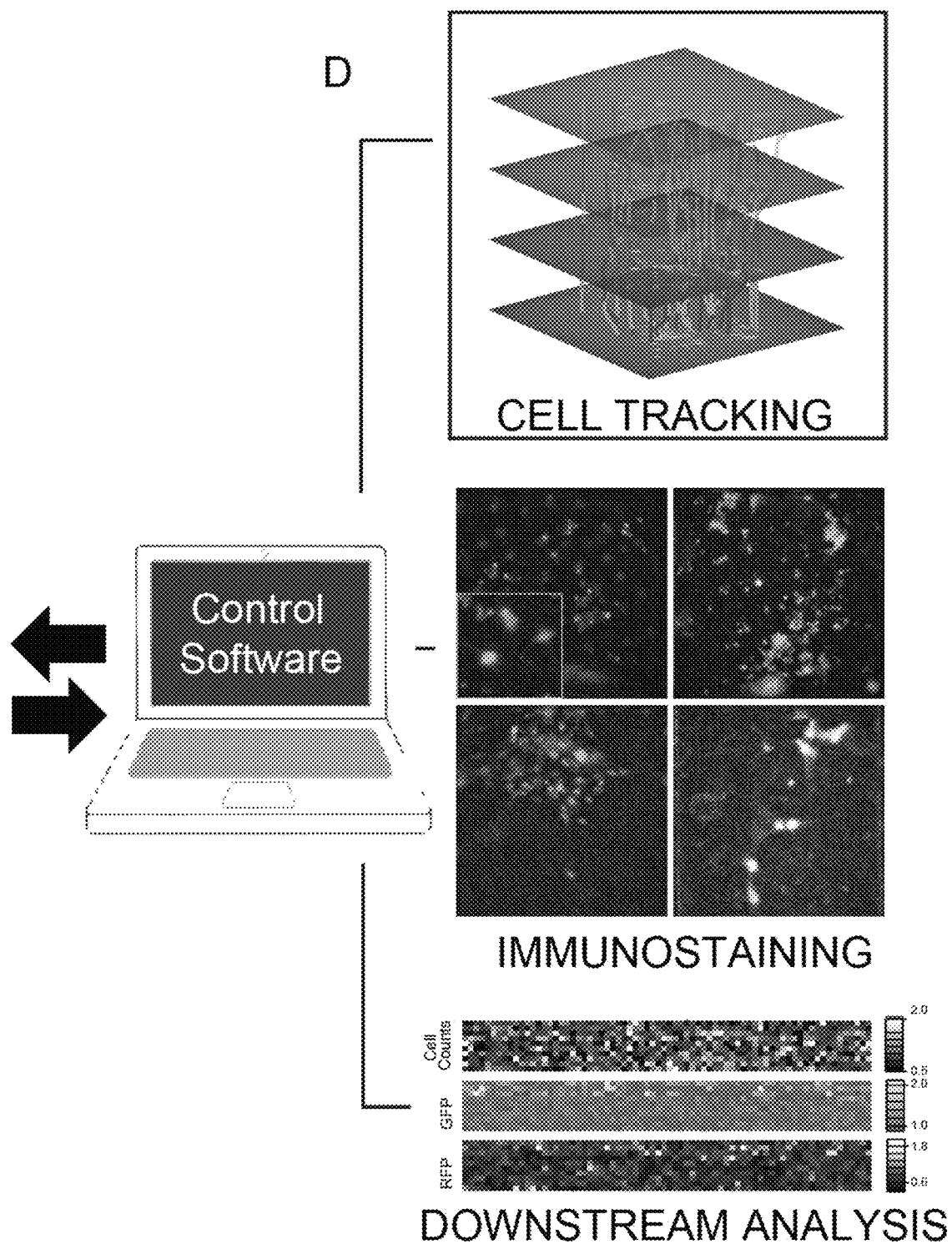

FIG. 1B shows optical images of one embodiment of the microfluidic chip, consisting of 3 components: (1) a multiplexer module, (2) an array of peristaltic pumps and (3) 1,500 individually-addressable shear-free culture chambers. The chamber is composed of two parts: a buffering unit (900 µm×400 µm×75 µm) and a culturing unit (400 µm×400 µm×75 µm, (FIG. 1C-1)). As, in certain embodiments, the culture chamber is designed with an inverted geometry, cells can be allowed to settle to the bottom of the culture chamber while flowing slowly over the top driven by a peristaltic pump, or directed to designated culture chambers through pressure-driven flow, which is considerably faster. In certain embodiments, four flow channels 25 µm in height and with a width of 100 µm allow two orthogonally-controlled flow modes: top-down in the loading and stimulation mode and left-right in the feeding mode (FIG. 1C-3). Numerical simulation shows that the flow in top-down direction, in certain embodiments, induces a maximum flow rate of 0.6 mm/sec over cells situated at bottom of the culture unit at 1 mm/sec flow rate (FIG. 1C-2, Flow or Stimulation mode). In certain embodiments, the culture medium can be replaced in ~5 seconds, enabling optimal stimulation without inducing differential cellular responses. Maintaining the same flow rate while directing the flow through the buffering layer (FIG. 1C-2, Feeding mode) reduces the flow rate at the bottom of the culture chamber to, in certain embodiments, zero. In certain embodiments, approximately 80% of the medium can be replaced within 20 seconds. In certain embodiments, cells experience zero shear flow even at 10 mm/sec during feeding mode and such feature makes the culture condition more consistent and robust against any geometrical differences from chamber to chamber and chip to chip. Moreover, conditional medium remains by isolating cellular environment from flow through the buffering layer, absence of which may cause variation in cellular state and morphology (Ying, et al., 2003; Ludwig, et al., 2006; Ghasemi-Dehkordi, et al., 2015). These novel features allow fast and frequent medium exchange without disturbing cellular environment and provide a stable medium composition comparable to the bulk experiments for long-term culture.

Automated Culture System for High-Throughput Combinatorial Stimulation and Analysis of Cellular Dynamics The simplicity of the chamber allows high throughput integration and control, providing testing of thousands of culture conditions in a single device. In certain embodiments, the inventors have integrated 1500 such chambers in a single microfluidic device, where each chamber is independent from the others and can be exposed to a different culture condition. These conditions can consist of different cell types, densities, support matrices, as well as 1500 precisely formulated combinations of chemical inputs such as signaling molecules and growth factors. In certain embodiments, the chemical inputs in each chamber can be changed over time using in-chip membrane valves and dedicated fluidic networks. With this device, the inventors surpassed the throughput of previous automated cell culture devices by 20-fold in terms of culture conditions generated allowing accelerated biological analysis.

To better utilize the high-throughput nature of this culture system, and to dynamically change the signaling microenvironment, the capability of on-chip formulation of chemical inputs is desired. For this purpose, the inventors designed and integrated a microfluidic system consisting an array of peristaltic pumps to formulate complex and dynamic chemical inputs on the chip (FIG. 1A). To efficiently deliver a formulated solution to any of the 1,500 designated culture units, in one embodiment, the inventors upgraded the peristaltic pump by integrating 8 parallel channels (100 µm in width). By increasing the driven fluid volume per pumping cycle, the enhanced pump can achieve, in this embodiment, approximately 30 nl/sec at 10 Hz pumping frequency to provide rapid and precise delivery of formulated solution. With such features, an arbitrary range of time-varying inputs with distinct characteristics, such as pulsed and sinusoidal input delivery, can be generated from a few previously prepared media vials connected to the chip, with the temporal resolution ranging, for example, from seconds to hours.

The inventors have developed software to operate this microfluidic culture and to automate many processes such as cell loading, input formulation and fluidic delivery (FIG. 2A). In certain embodiments, the inventors further integrated this system to an automated fluorescent microscope to realize a total-analysis system capable of monitoring single cells and cell populations via live-cell microscopy in weeks-long experiments in precisely formulated signaling microenvironments (FIG. 2B).

In certain embodiments, the combination of dynamic input formulation, 1500 independent culture chambers, diffusion based stimulation, and the ability to create single cell, 2-D or 3-D culture greatly enhances the capabilities for applications when dynamic control of the microenvironment is preferred.

Highly Viable Cultivation of Primary Single Cells and 2-D Cultures

The Achilles heel for microfluidic cell culture has been the poor viability of cells grown in PDMS based microchambers, which is especially severe for sensitive primary mammalian cells (Mehling, et al., 2014). The lack of control and functionality desired for complicated biomedical studies contribute to the relative rarity of microfluidic studies on primary cells as well. To demonstrate the capability of the present system in culturing and stimulating different cell types (both cell lines and primary cells) the inventors first cultured a mouse fibroblast 3T3 cell line and human hematopoietic stem cells (HSCs) in adherent and suspension culture mode respectively, and stimulated cells either with constant or pulsed formulations of the inflammatory cytokine TNF-alpha to induce NF-κB signaling (Kellogg, et al., 2015; Tay, et al., 2010). Dynamic (i.e., pulsed or sinusoidal) stimulation of non-adherent cells such as HSCs was not demonstrated before the present study. NF-κB is an important gene network that integrates signals from a multitude of extracellular sources, and is central in regulating innate and adaptive immunity. Dynamic stimulation of NF-κB in single-cells as shown here can be very informative in understanding and modeling cellular information processing in complex scenarios like infection, autoimmunity and cancer.

Figure 10A:
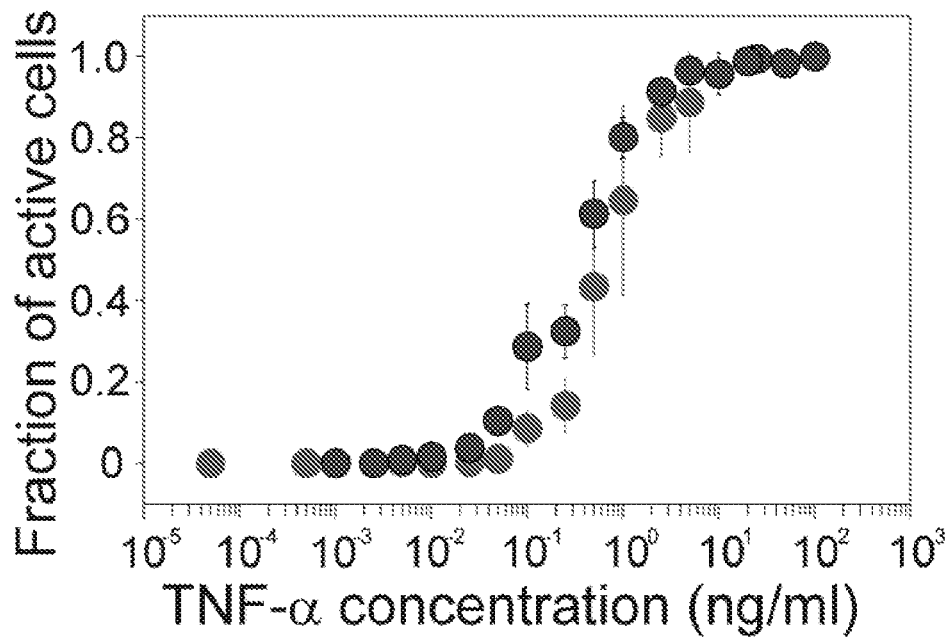
FIGS. 10A-10D illustrate features of the assessment of an example of the present microfluidic chips for cell culture and signaling.
Figure 10B:
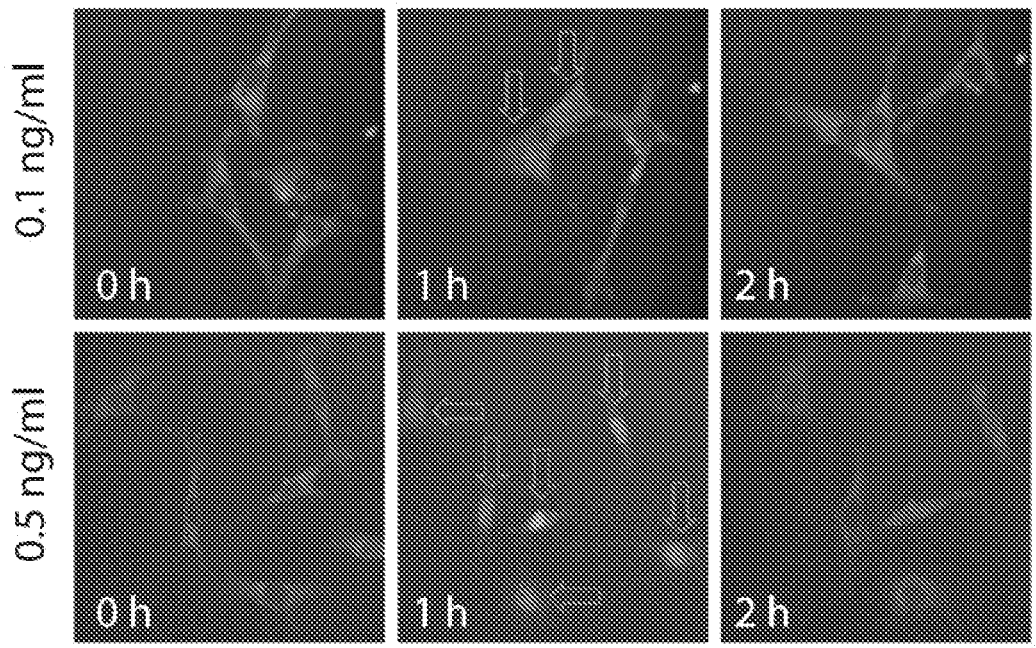
Figure 10C:
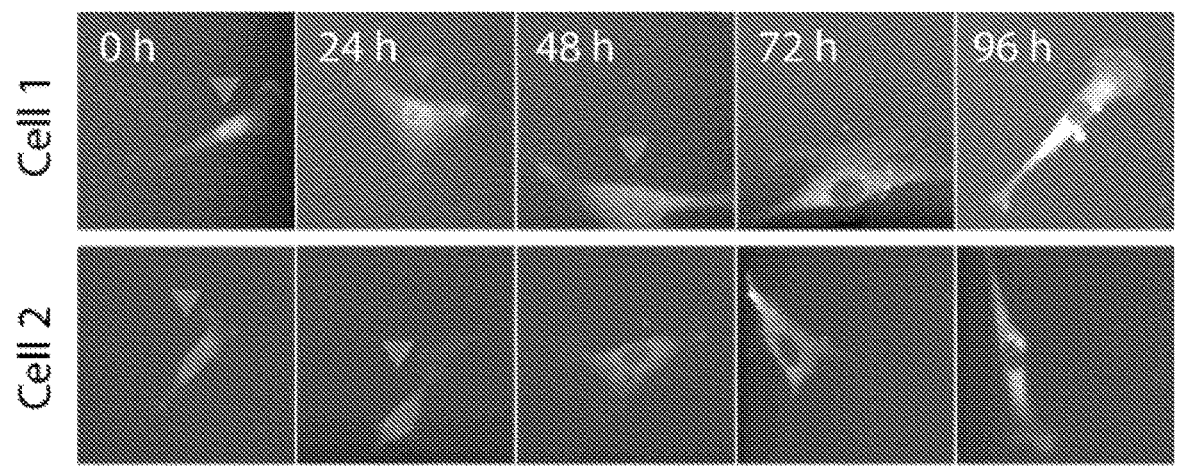
Figure 10D:
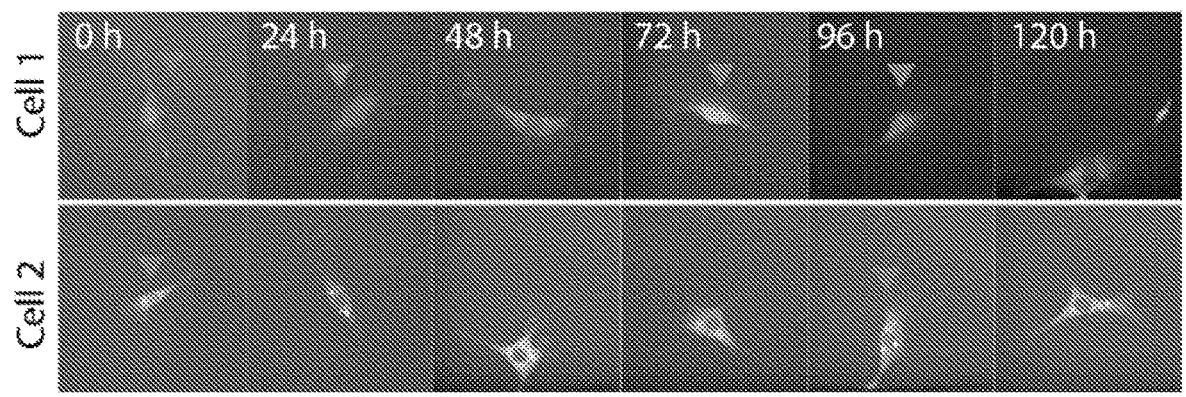

The inventors took advantage of the long-term stable culture capability of the device and extended TNF-alpha induced NF-κB activation study in 3T3 fibroblasts for up to a week. The response of 3T3 cells to TNF-alpha stimulation is characterized by the nuclear translocation of transcription factor NF-κB, and visualized through automated fluorescence imaging (Kellogg, et al., 2015). Both single cells and a population of cells were successfully maintained in the present culture chambers, and were stimulated with series of TNF-alpha concentrations (0.001 to 100 ng/ml), which were simultaneously generated on-chip. With populations of 3T3 cells, the fractions of activated cells versus TNF-alpha concentration are consistent with previously published results, showing the chip's reliability and reproducibility (FIGS. 10A and 10B) (Tay, et al., 2010). At the single cell level, all cells respond to the first pulse stimulation with 0.1 and 0.2 ng/ml TNF-alpha (FIGS. 10C and 10D). Prolonged incubation and stimulation for one week lead to increase in 3T3 cytoplasm NF-κB level and inert cell responses. Meanwhile, the cytoplasm NF-κB level is proportional to TNF-alpha concentration.

Figure 11A:
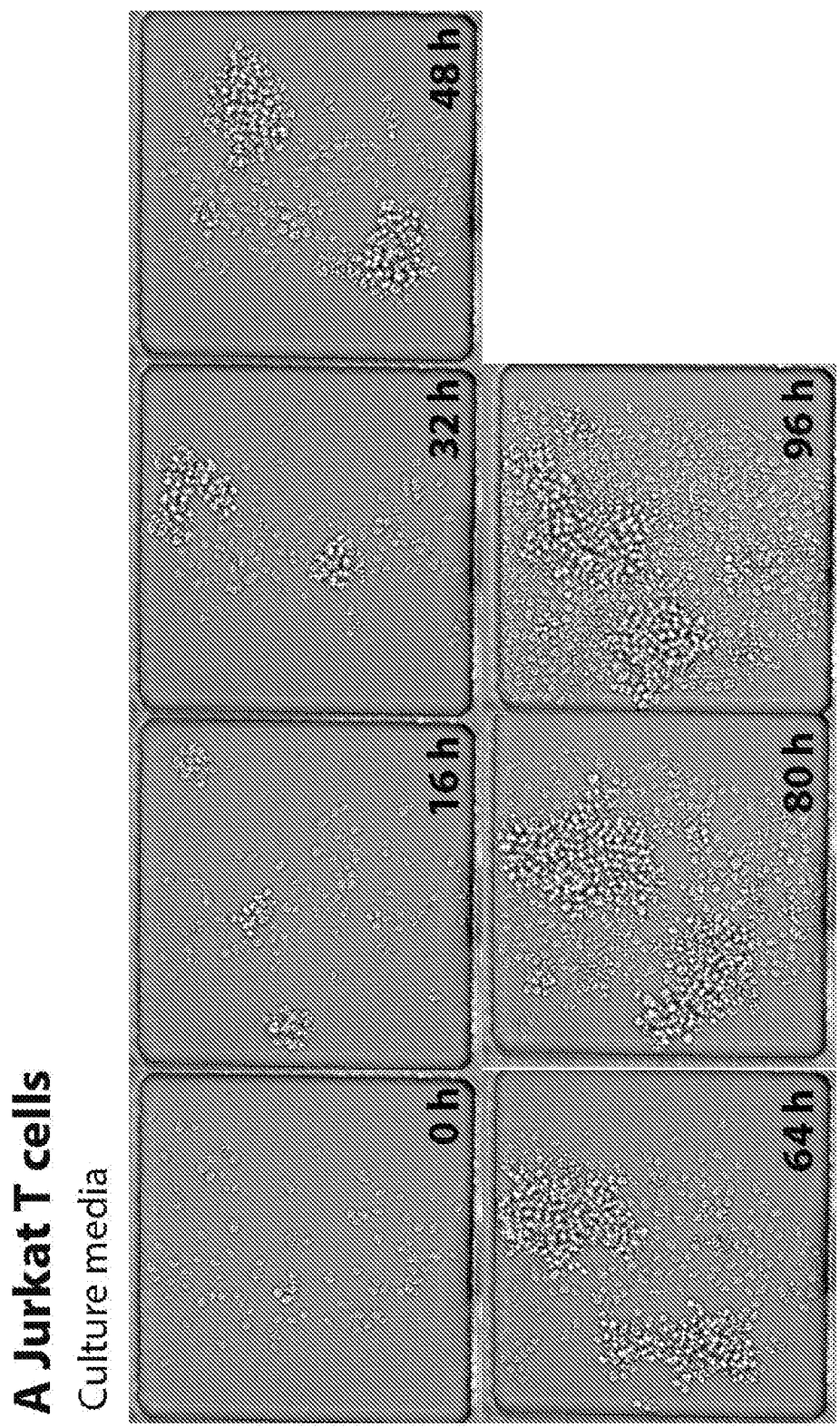
FIGS. 11A-11B illustrate features of the use of an example of the present microfluidic chips for culture and stimulation of cell-lines and primary cells.
Figure 11B:
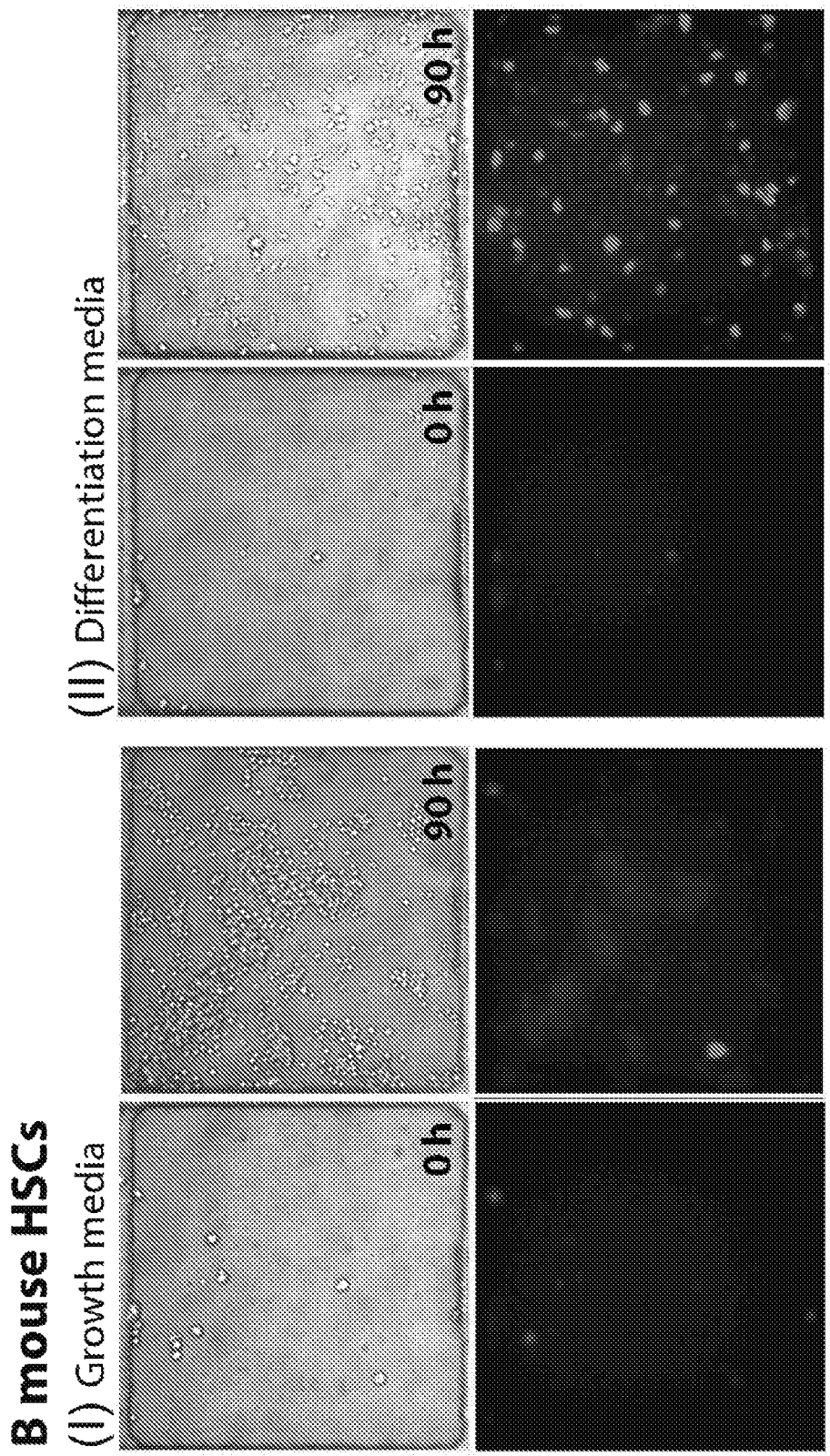

Besides being a signaling protein involved in systemic inflammation, TNF-alpha is also widely employed to mimic the post-transplantation signaling environment (Mohabbat, et al., 2012). To mimic clinical hematopoietic stem cell transplantation (HSCT), different doses of TNF-alpha are directed to designated culture chambers housing HSCs by programmed medium exchange procedures. The inventors observed that TNF-alpha stimulation can directly cause the death of HSCs (FIG. 2B). The capacity of the present device as a universal culture chip for various cell types is further demonstrated by the successful culturing of suspension cells including Jurkat T cell line and mouse HSCs (FIGS. 11A-11B). In both cases, cells proliferate at a similar, if not higher, rate than those in bulk experiments in traditional culture dishes.

Highly Viable Cultivation and Differentiation of Neural Stem Cells and 3-D Neuronal Organoids In certain embodiments, the tall height (150 μm) of the present 2-level design extends the chip's functionality into 3D culture of cells and organoids. Without exposing the culture chamber to flow, stable experimental conditions, e.g., conditional media and the integrity of hydrogels, can be well maintained. Unlike mouse HSCs, which have been studied rather extensively as a model system, embryonic neural stem cells (NSCs) are extremely sensitive to their environment and there have been only limited successes when cultured in microfluidic devices (Dorshkind, et al., 2010). Studies show that variations in environmental conditions may lead to spurious cell response, decreased growth rate and even cell death (Wolfe, et al., 2013).

Figure 4A:
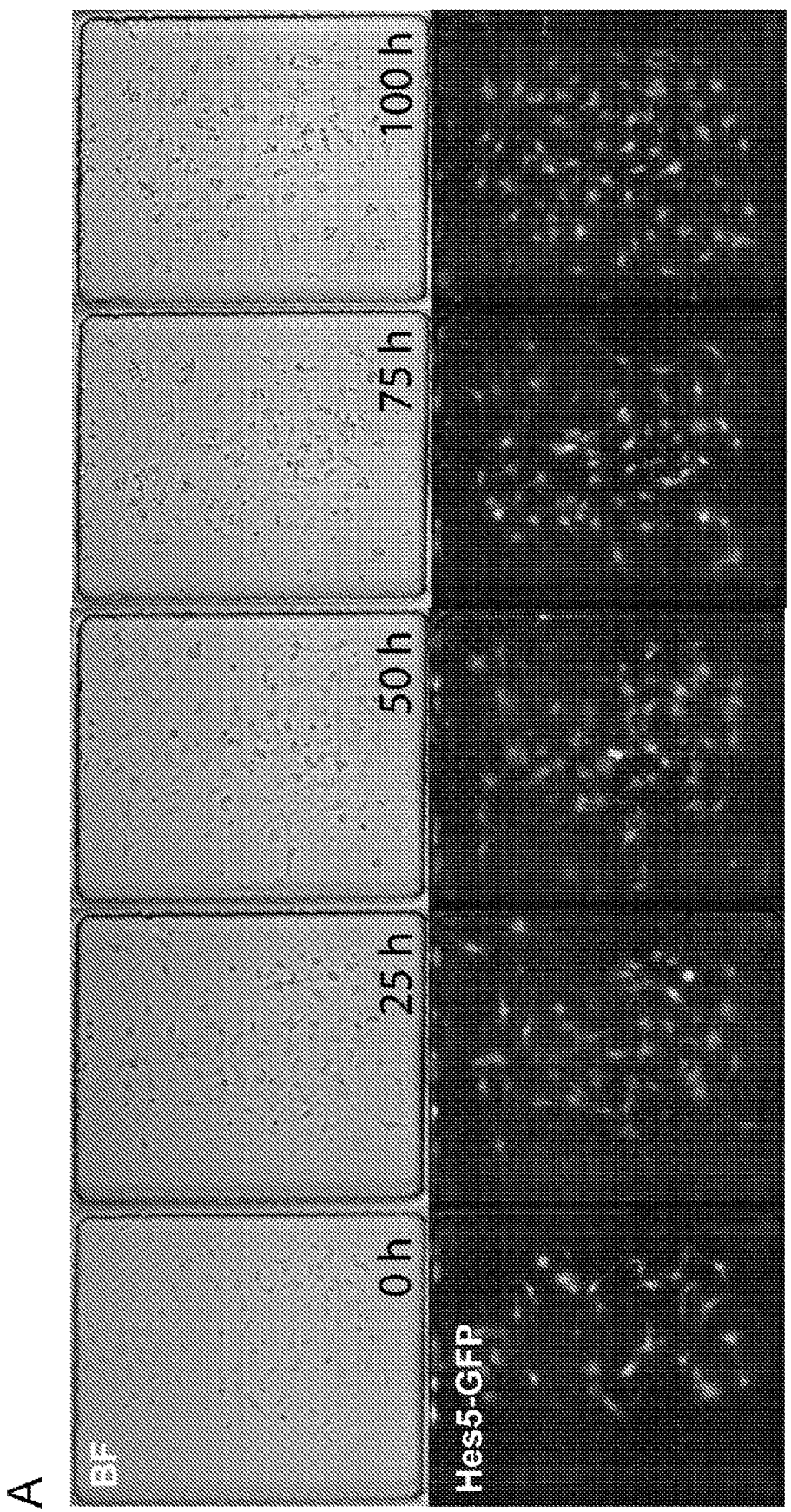
FIGS. 4A-4C illustrate features of the use of the present microfluidic chips for multi-mode culture of neural stem cells.

Here, the inventors demonstrate the capability of the present chip in long-term culturing of NSCs under three distinct modes: (1) suspension, (2) adherent and (3) in 3D hydrogel culture. Expression of Hes5 protein, one of the downstream gene targets upon Notch signaling activation, is used as the marker for NSCs self-renewal (Ohtsuka, et al., 2001; Basak, et al., 2007). The inventors therefore used mouse derived primary NSCs and monitored the expression of the fusion protein Hes5-GFP to probe the NSC self-renewal and differentiation. For adherent culture, the inventors tested several protocols, and found that NSCs would gradually dissemble, spread, and migrate on the PDMS surface coated with poly-lysine and laminin without FACS sorting and dissociation (FIG. 4A). Visible features such as cell morphology, Hes5-GFP level and cell growth are monitored for a week in these dissociated cells. Upon spreading, the overall Hes5-GFP level of single NSCs remains unchanged. During the first 24-hour continuous feeding (20 sec feeding with 30 min interval), the cell number roughly doubles.

Figures 4B, 4C:
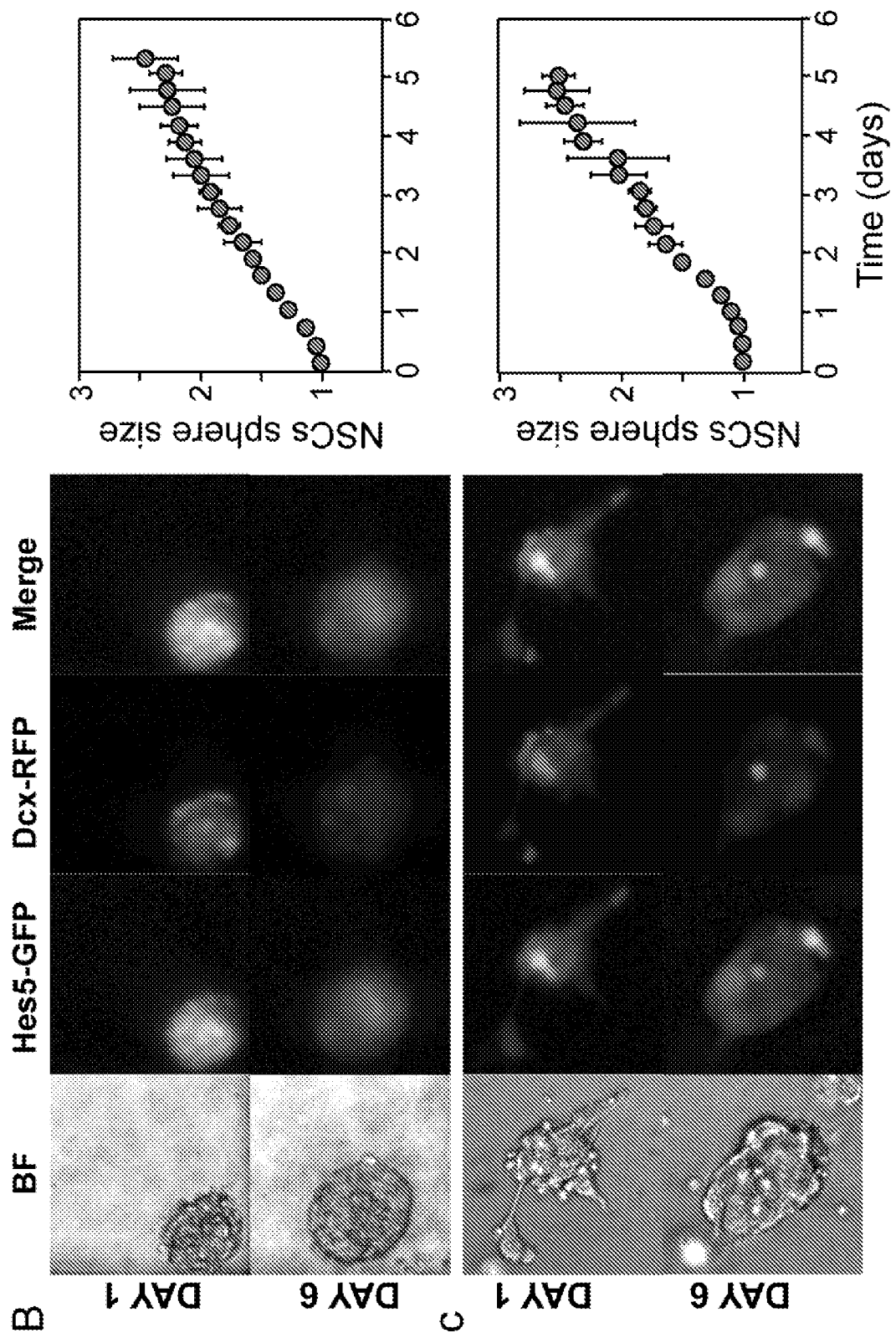
Figure 12A:
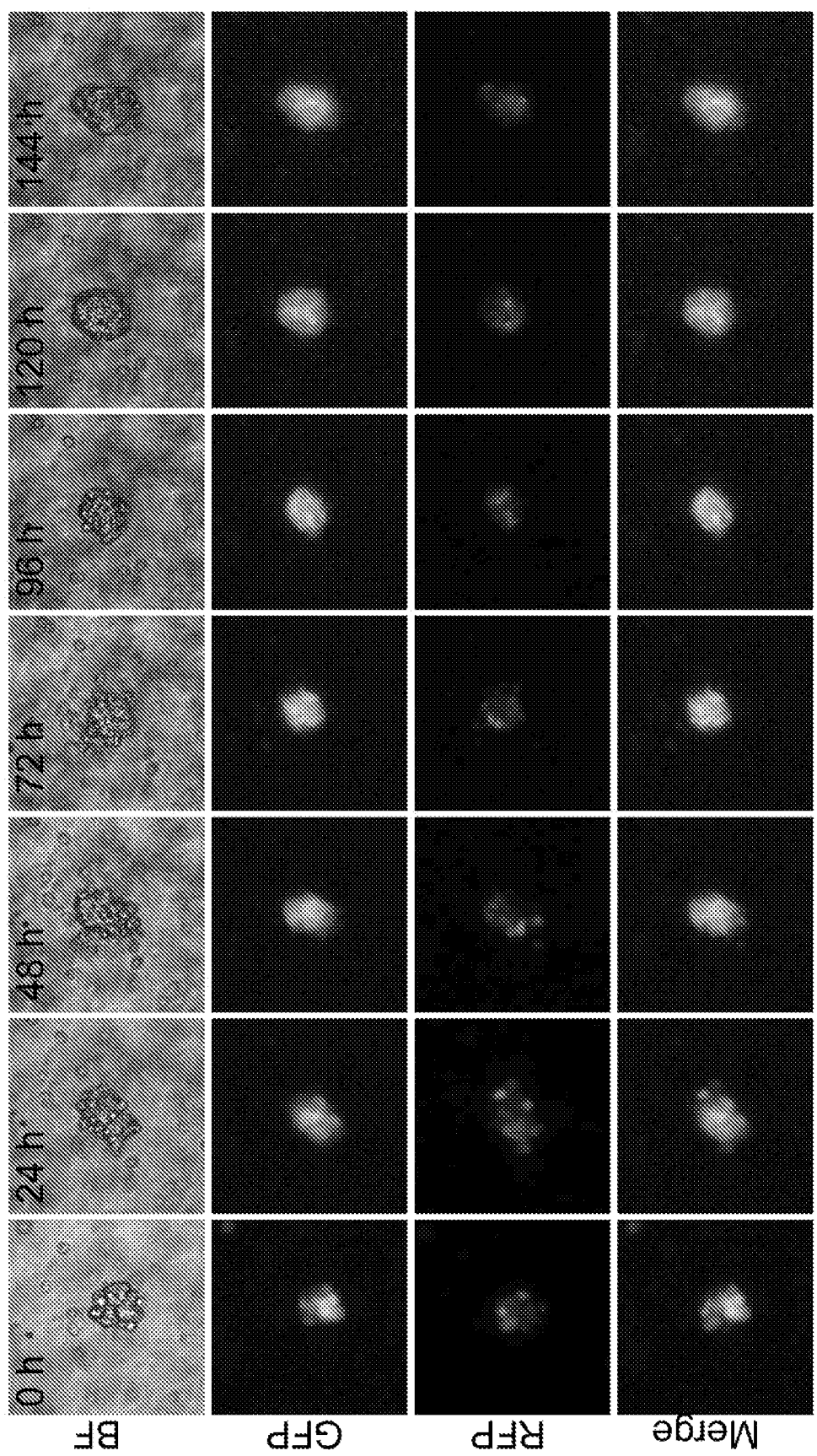
FIGS. 12A and 12B depict the multi-mode culture of neural stem cells.
Figure 12B:
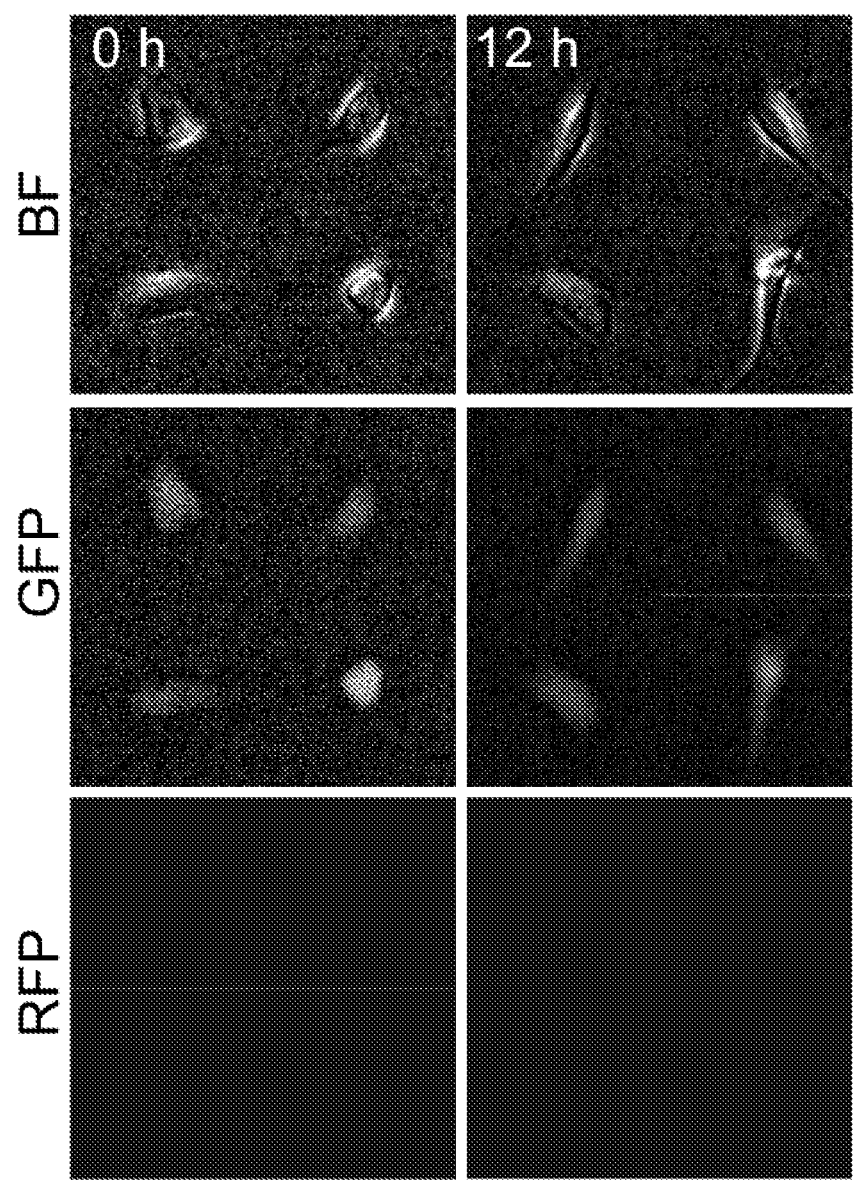

In certain embodiments, for suspension neurosphere and 3D hydrogel culture, NSCs spheres are directly loaded into untreated (bare PDMS) culture chamber either with or without collagen hydrogel, respectively (FIGS. 4B and 4C). Through live cell imaging, the inventors observed that the diameter of NSCs sphere roughly doubles (corresponding to approximately 8-time increase in monolayer culture assuming a constant cell volume) in both cases after 6 days of culture. Despite sharing similar growth rate, NSCs spheres cultured in 3D hydrogel exhibited more extended axons and elongated shape, suggesting higher degree of cell attachment to the surrounding hydrogel. The inventors further demonstrated that such cultured cells can be recovered and used for further studies by retrieving NSCs spheres from the device and cultivating them in the 96-well plate successfully (FIG. 12B). Altogether, these results show that the present microfluidic chip can be used for culture of suspension, adherent and 3D spheres of embryonic NSCs and has the potential for studies on organoids.

Combinatorial and Dynamic Stimulation to Study Neural Stem Cell Differentiation and Brain Development Stem cell niche consists of a combination of signaling molecules and growth factors whose type and concentration change over time. To recapitulate the signaling niche and early transcriptional events during mammalian forebrain development in vitro, the inventors took advantage of the capabilities and the throughput of the present system and cultured NSCs under complex and time varying signaling inputs. In RNAseq measurements, the inventors identified 6 signaling molecules that are highly expressed during early mouse forebrain development, these are PDGF, CXCL, PACAP, DLL, Jagged, and EGF. To understand how the NSCs' differentiation and self-renewal is regulated by the temporal sequence of participating ligands, a series of combinatorial and sequential inputs of these 6 selected ligands are generated on-chip (FIG. 5, 7; FIGS. 13-16). In total, around 800 conditions (including sequential, combinatorial and dose-dependent conditions) were generated and delivered to designated cell culture chambers that hold primary mouse NSCs. Some cells were stimulated with different permutations of all available ligands during the entire experiment (combinatorial inputs), while others were stimulated with a different ligand every day (sequential inputs). The cells expressed Hes5-GFP as well as Dcx-DsRed protein. These reporters along with the analysis of cell morphology and growth indicated either stemness (high Hes5, low Dcx), or differentiated neurons (low Hes5 and high Dcx, and neuron-like morphology), or Astrocytes (low Hes5, and astrocyte-like morphology).

Figure 5A:
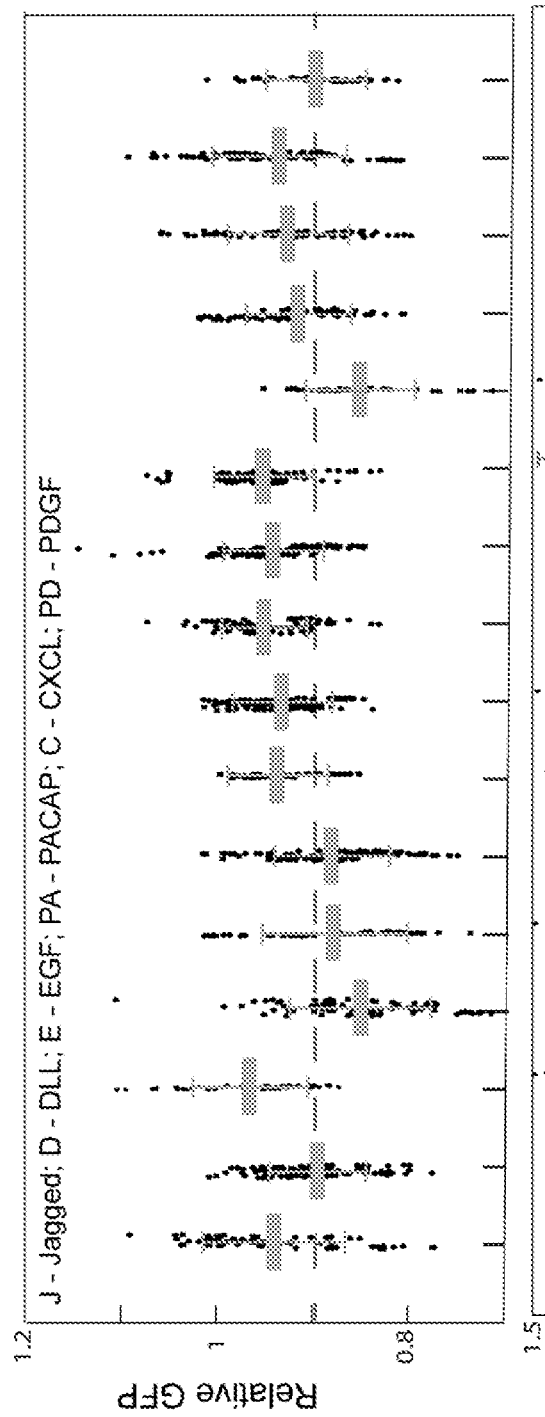
FIGS. 5A-5C illustrate high-throughput studies on NSCs responses to complex inputs, and data collection and decision tree analysis of sequential inputs.
Figure 5B:
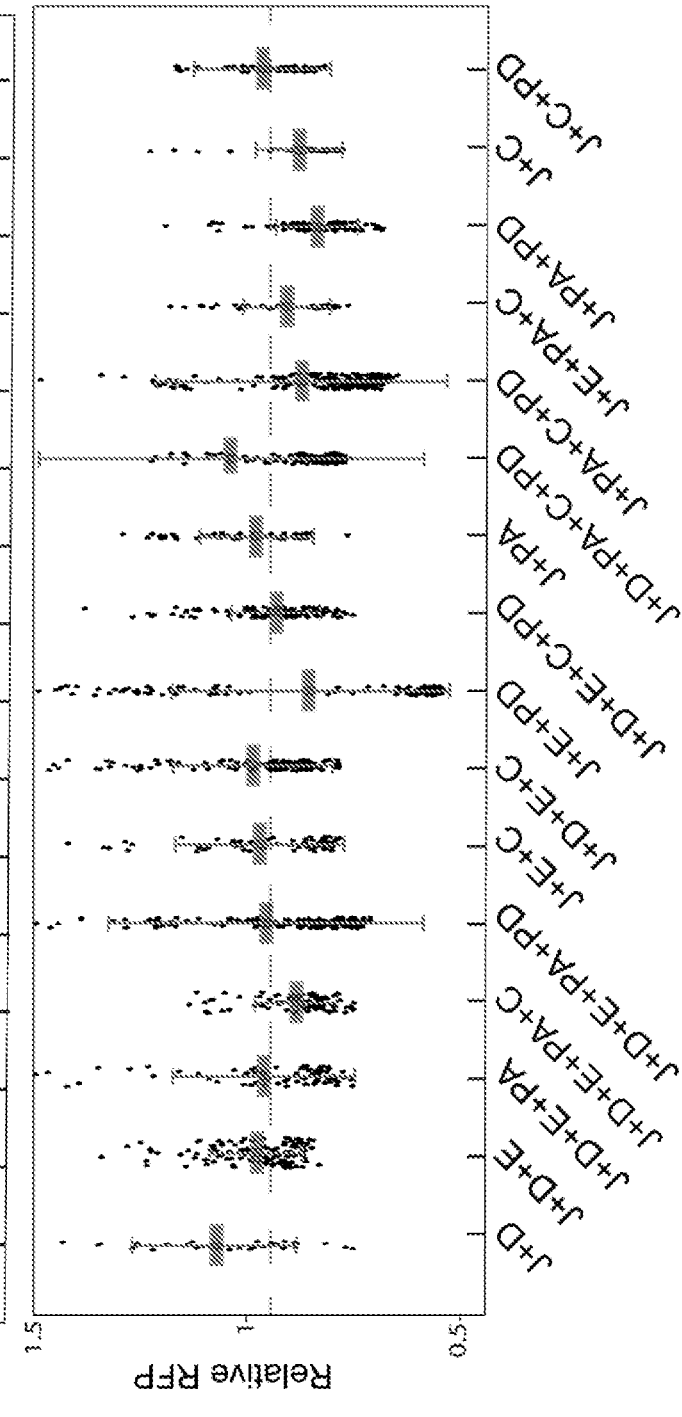

The inventors observed large and quantifiable differences in growth rate, morphology, Hes5 and Dcx levels in the adherent NSCs culture (FIG. 5B). The inventors compared these features obtained under each condition (sequential and combinatorial) to that of control experiments where NSCs are cultured in normal media (FIG. 22).

Discussion

The high-throughput microfluidic system the inventors demonstrated here represents the next generation of cell culture and live-cell analysis systems suitable for a wide range of applications in stem cells, immune signaling and organoids. In certain embodiments, the inventors exceed the existing throughput of independently addressable microfluidic cell culture systems by nearly 20-fold. This truly lab-on-a-chip platform has advantageous features including an advanced yet simple 2-level cell culture chamber, which allows precise control over media and signaling input delivery while maintaining a stable cellular environment. The capacity of generating both static and dynamic complex inputs (such as pulsed or sinusoidal inputs), together with, in certain embodiments, 1,500 individually-addressable culture units, provides powerful solutions for screening studies, particularly for the studies of the complex environmental effects on cellular responses, most of which used to be technologically challenging and time-consuming before this study.

Figure 1E:
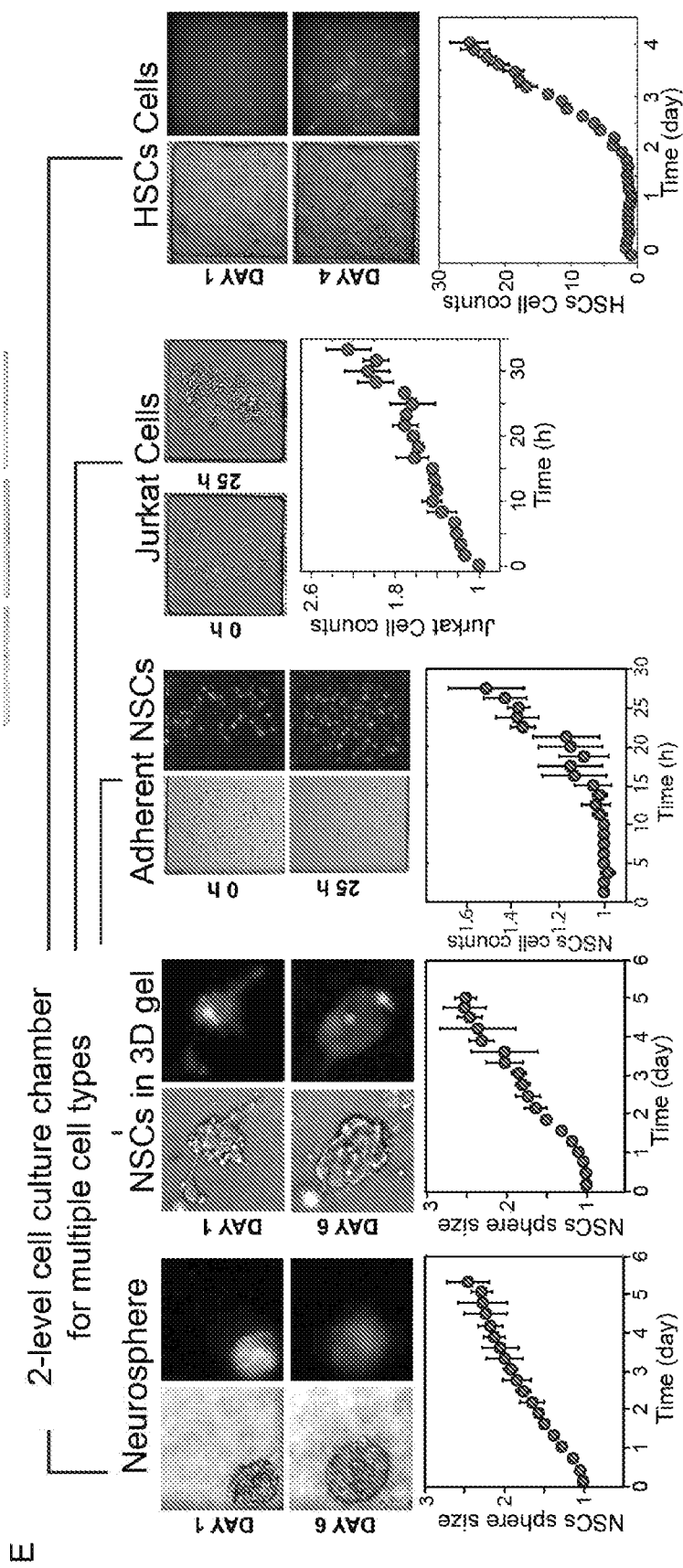

One advantage of the device, offered by its two-layer chamber geometry, is the spatial separation between the culture chamber and buffering area used for media delivery (FIG. 1C). The 2-level device reported here provides an elegant solution with a buffering layer imbedded that serves as a cushion during media exchange. It is found that flow remains zero at the bottom of the culture unit with up to 10 mm/sec flow rate in the buffer chamber. This robustness against shear flow is critical for studies on sensitive primary cells and other delicate biological samples. Additionally, while maintaining cells in the shear-free environment, the chip is able to perform rapid and complete fluid exchange, either by direct flow or by diffusion, which is important for cell signaling studies. In certain embodiments, with 4-valve control, fluid can be directed either through the buffering layer or directly over the culture chamber (FIGS. 1D and 1E). In certain embodiments, the 150 μm height of the culture chamber further extends the chip's functionality to accommodate biological samples in 3D micro-environment such as embryonic NSCs neurospheres.

Named as a "Universal Cell Culture Chip", its universality has been examined using a wide range of both cell lines (including fibroblast 3T3 cell, Raw 264 cell and Jurkat T cell) and primary cells (including mice HSCs, human HSCs and mice embryonic NSCs). This list of cells includes both adherent and suspension cells. It is observed that fibroblast 3T3 and Jurkat T cells proliferate at a comparable rate as if in traditional culture in a dish (FIG. 11A). Cell retrieval from the chip (3T3 and Jurkat, respectively) through fast fluid flow can achieve >95% efficiency. Fibroblast NF-κB response to TNF-alpha stimulation in the present culture system was seen to reproduce previous findings in this important signaling pathway. Due to extremely improved culture conditions in the present device compared to previous microfluidic culture systems, the inventors were able to load and maintain single fibroblast cells in isolation and stimulate them with various doses and timings of TNF-alpha. Such multiplexed control and analysis of NF-κB response in isolated live cells was not demonstrated before.

Figure 3A:
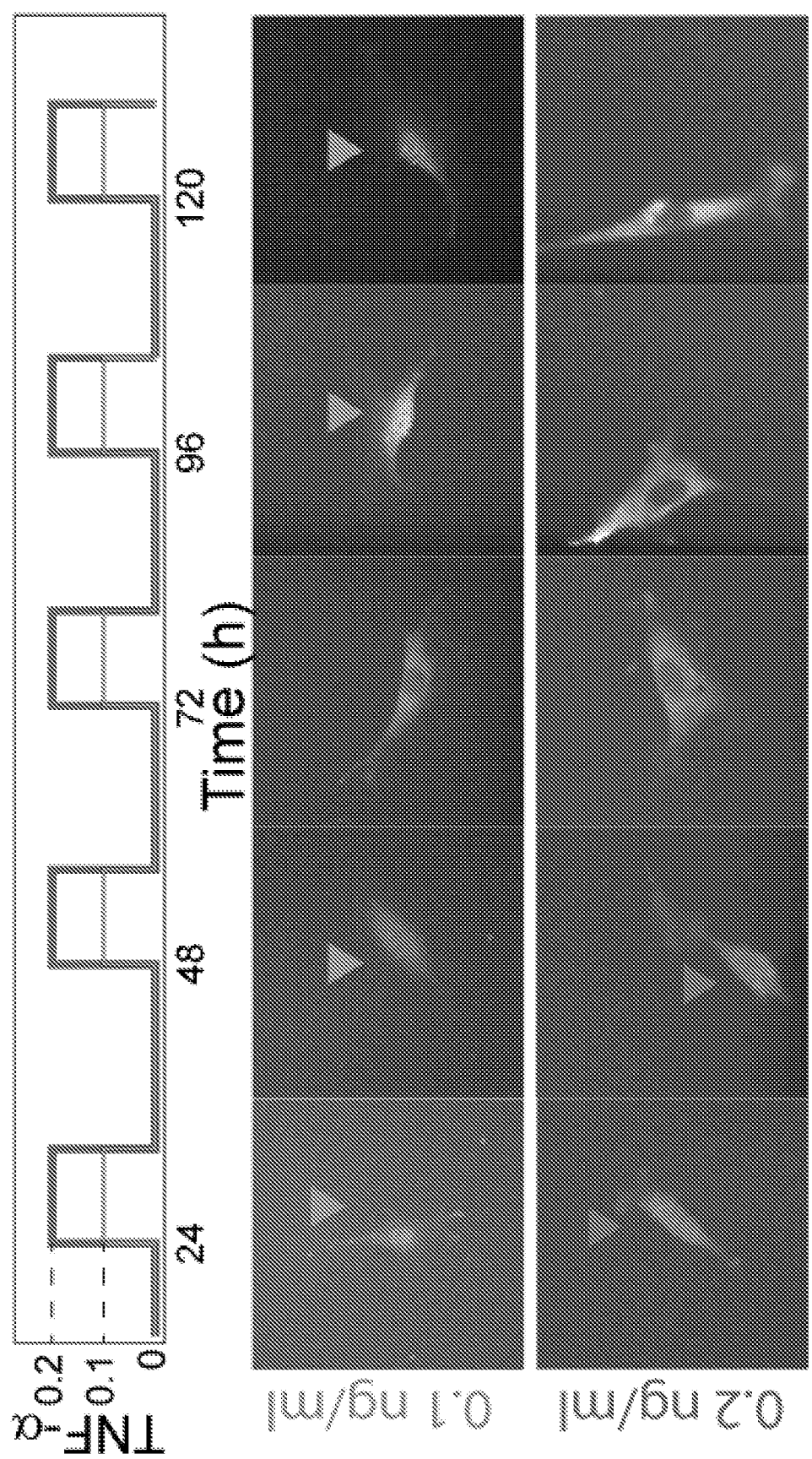
FIGS. 3A-3B depict assessments of high-throughput microfluidic chips for culture and stimulation of cell-lines and primary cells
Figure 3B:
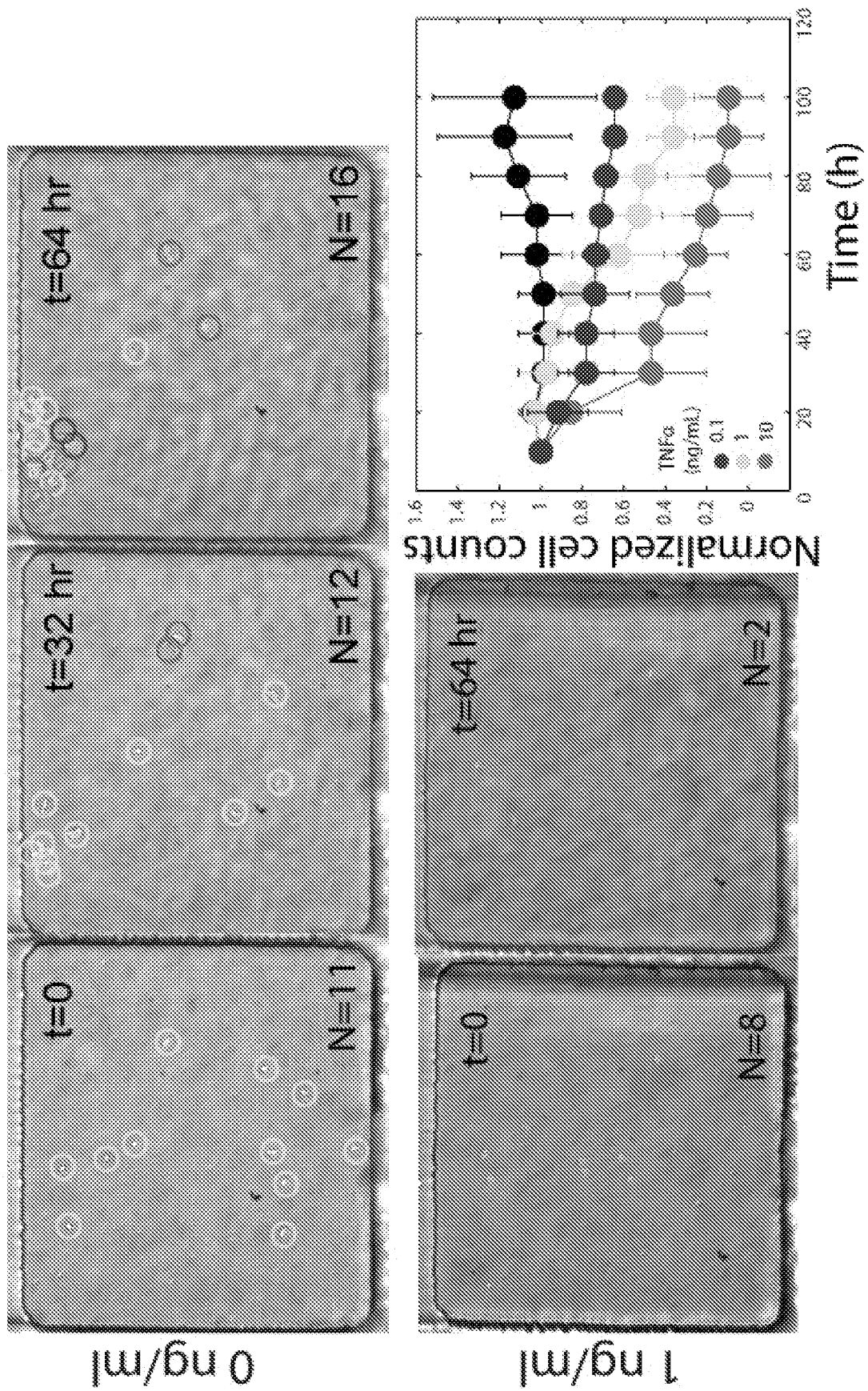
Figure 3C:
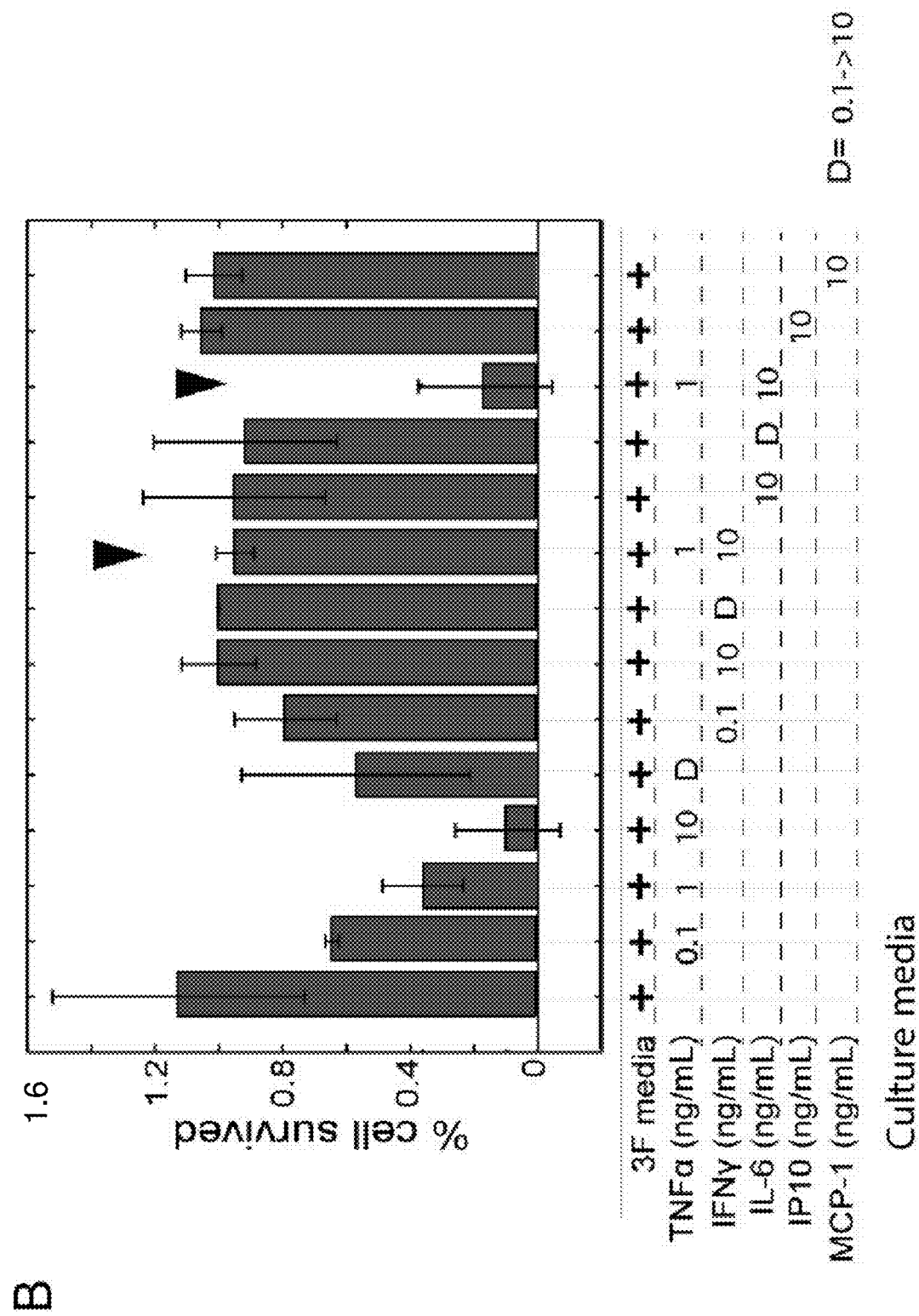
FIG. 3C depicts a chart of long-term culture and TNF stimulation of human hematopoietic stem cells (HSCs). Cells were cultured on the microfluidic device in the absence of TNF (control) and 1 ng/ml TNF, for up to 5 days. Upper right panel shows cell numbers (relative) after stimulation with TNF (black dots are control culture chambers, at TNF=0). N indicates cell numbers per chamber. Lower panel shows effect of TNF with the presence of other participating cytokines (IFNγ, IL-6, IP10 and MCP-1). TNF induces dosage-dependent death of human HSCs, and IFNγ neutralize TNF induced cell death. D represents dynamic cytokine inputs, daily variation between 0.1 and 10 ng/ml.

Although human HSCs culturing is more challenging for on-chip culture compared with mice HSCs, the inventors still can observe clear cell proliferation during the present 6-day chip experiment (FIG. 3B and FIG. 11B). One difference lies in that human HSCs employed in this study are purified human CD34+ cells, which are 98% pure HSCs and have been typically used to model HSCT in preclinical mouse models. While, mice HSCs cells are freshly isolated CD45+EPCR+CD48−CD150+(E-SLAM) adult mouse bone marrow cells, which are approximately 50% pure HSCs. Human CD34+ cells are much lower in initial cell number (a few thousands per harvest), which affects cell growth rate. Loading approximately 10 cells per chamber, in one embodiment, the present microfluidic device allows the study on human HSCs to, for example, 200 conditions upon 1 sample harvest which generally only gave total of few thousand cells. An instantaneous response of mice HSCs to M-CSF input suggests that media replacement through the buffering layer is effective (FIG. 11B). Similarly, dose-dependent TNF-alpha induced cell death is observed among human HSCs (FIG. 3B). In both cases, HSCs show unperturbed migration trajectory and clear responses to programmed inputs, suggesting fluid is delivered to designated culture unit without shear force disturbance.

Figure 13B:
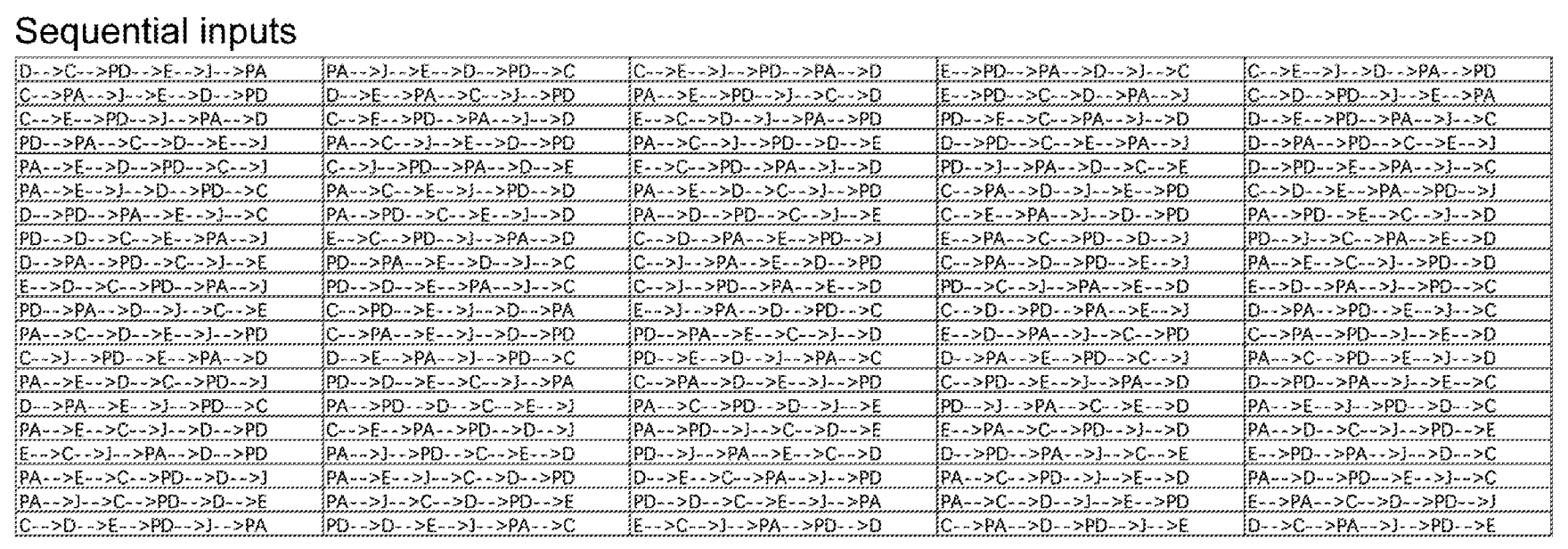
Figure 13C:
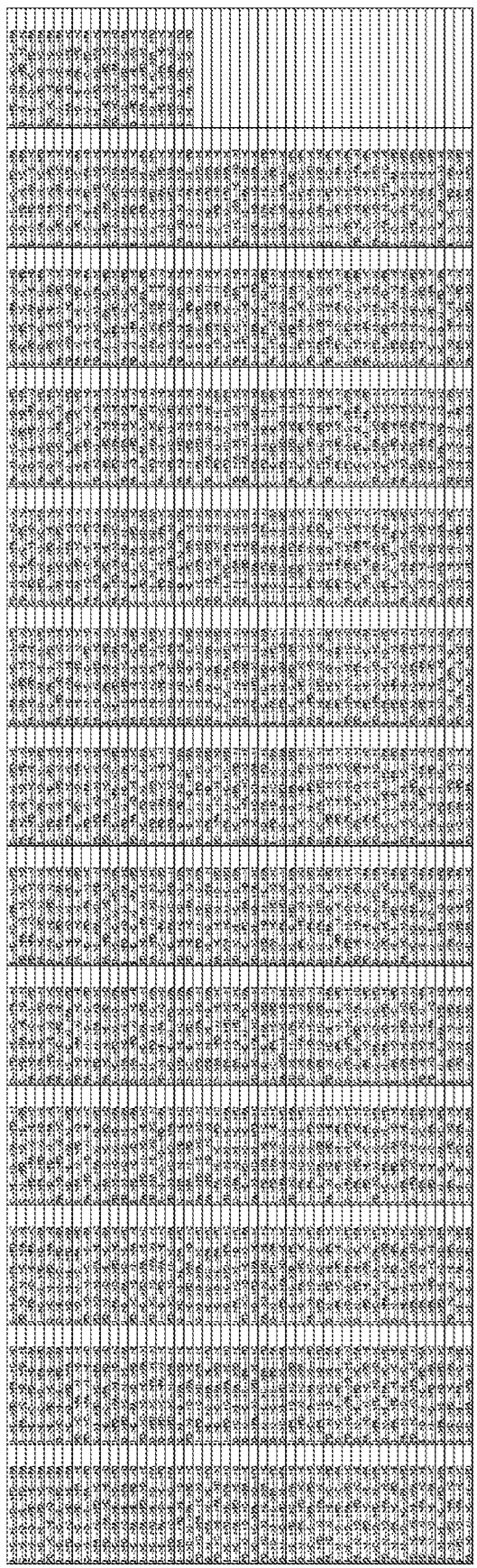
Figures 3, 13C:
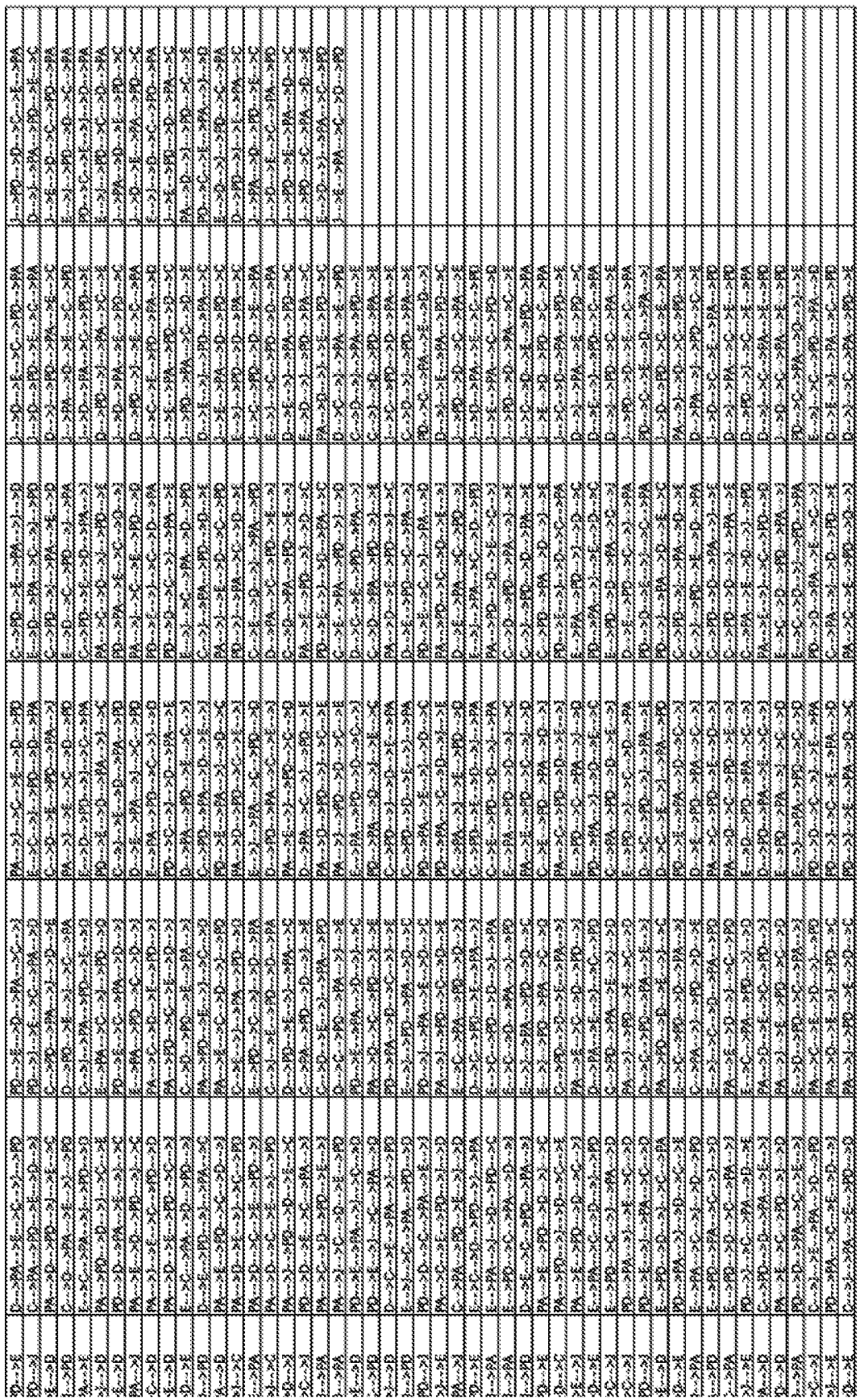
Figure 14:
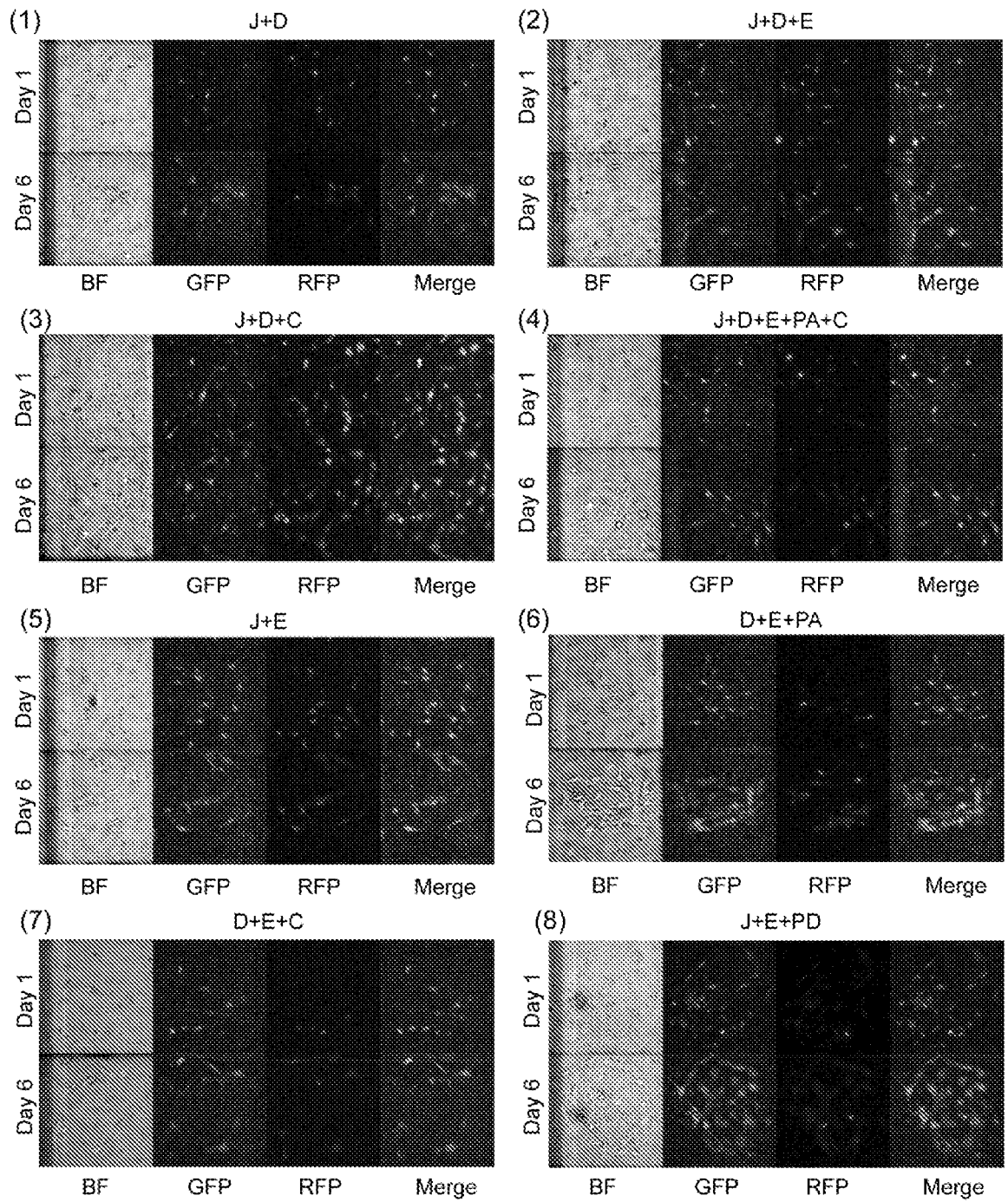
FIG. 14 depicts images of on-chip studies of NSCs in responses to combinatorial inputs. Bright-field and fluorescent images of NSCs cells on 1st day and 6th day with selected combinatorial inputs: (1) Jagged and DLL; (2) Jagged, DLL and EGF; (3) Jagged, DLL and CXCL; (4) Jagged, DLL, EGF, PACAP and CXCL; (5) Jagged and EGF; (6) DLL, EGF and PACAP; (7) DLL, EGF and CXCL; (8) Jagged, EGF and PDGF.
Figure 15:
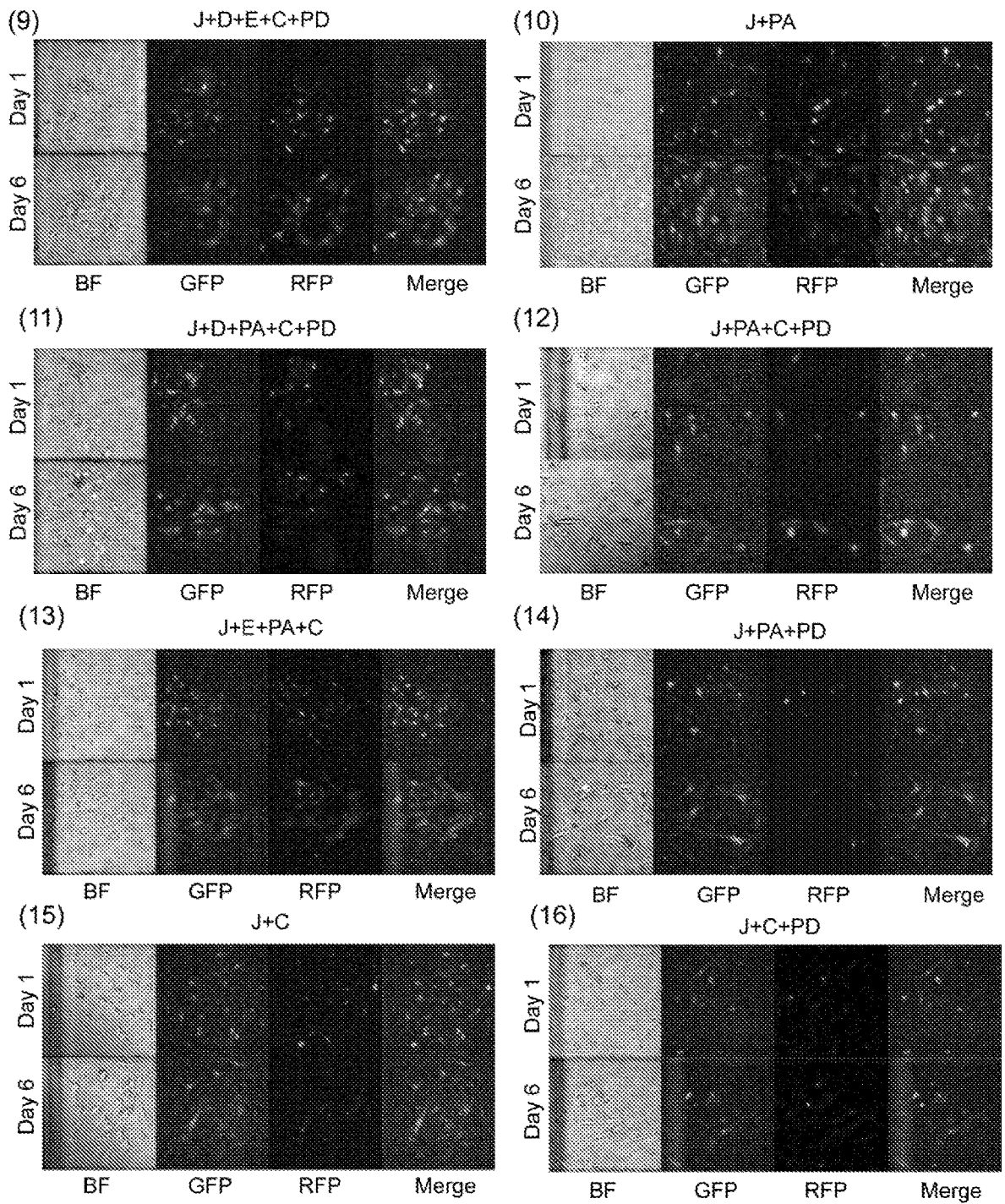
FIG. 15 depicts images of on-chip studies of NSCs in responses to complex inputs, particularly time-lapse fluorescent image of NSCs cell culture on chip with combinatorial inputs. Fluorescent images of NSCs cells on 1st day and 6th day with combinatorial inputs (1) Jagged and DLL; (2) Jagged, DLL and EGF; (3) Jagged, DLL and CXCL; (4) Jagged, DLL, EGF, PACAP and CXCL; (5) Jagged and EGF; (6) DLL, EGF and PACAP; (7) DLL, EGF and CXCL; (8) Jagged, EGF and PDGF.
Figure 16:
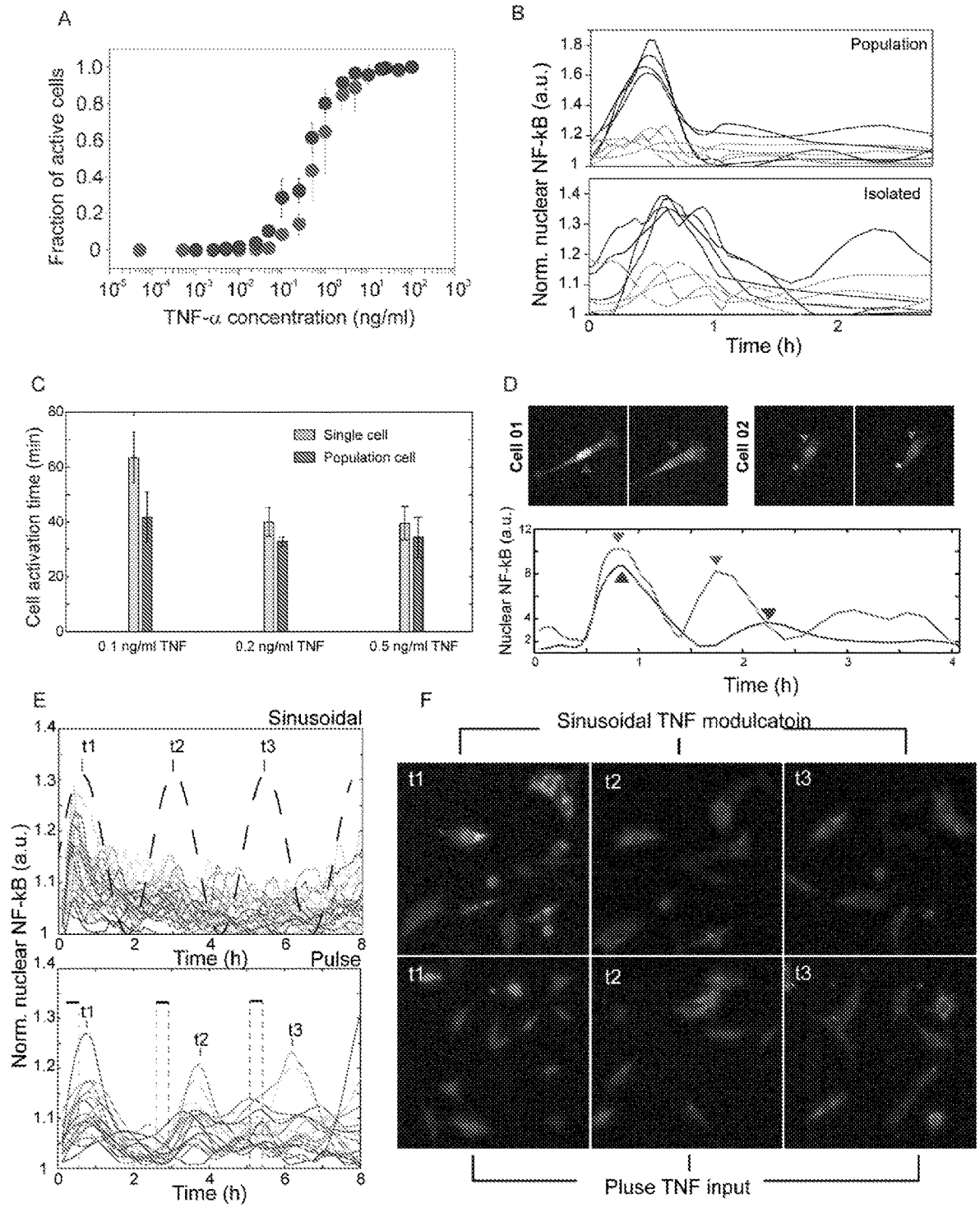
FIGS. 16A-16F depicts dynamical cell culture and NF-κB Signaling.
Figure 17:
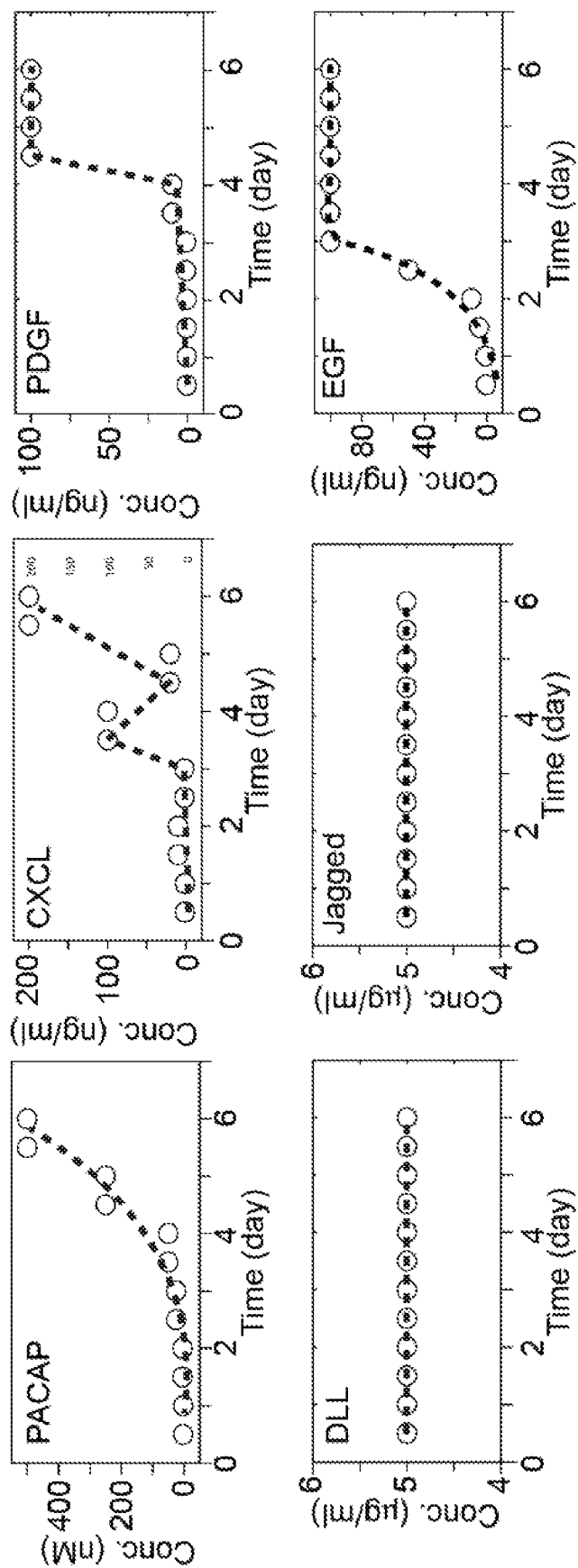
FIG. 17 depicts concentration variations for dynamic inputs studies. For experiments with single ligands, series of pre-programmed ligand concentrations are maintained in designated culture units by on-chip dilution function. Similarly, dynamic environment composed of 6 ligands are accomplished by carefully mixing 6 ligands to the designed concentration and ratio. For combinatorial and sequential inputs with constant ligands' dose, all concentrations are maintained at the highest effective values (e.g. PACAP: 500 nM, CXCL: 200 ng/ml, PDGF: 100 ng/ml, DLL: 5 μg/ml, Jagged: 5 μg/ml, EGF: 100 ng/ml).
Figure 19:
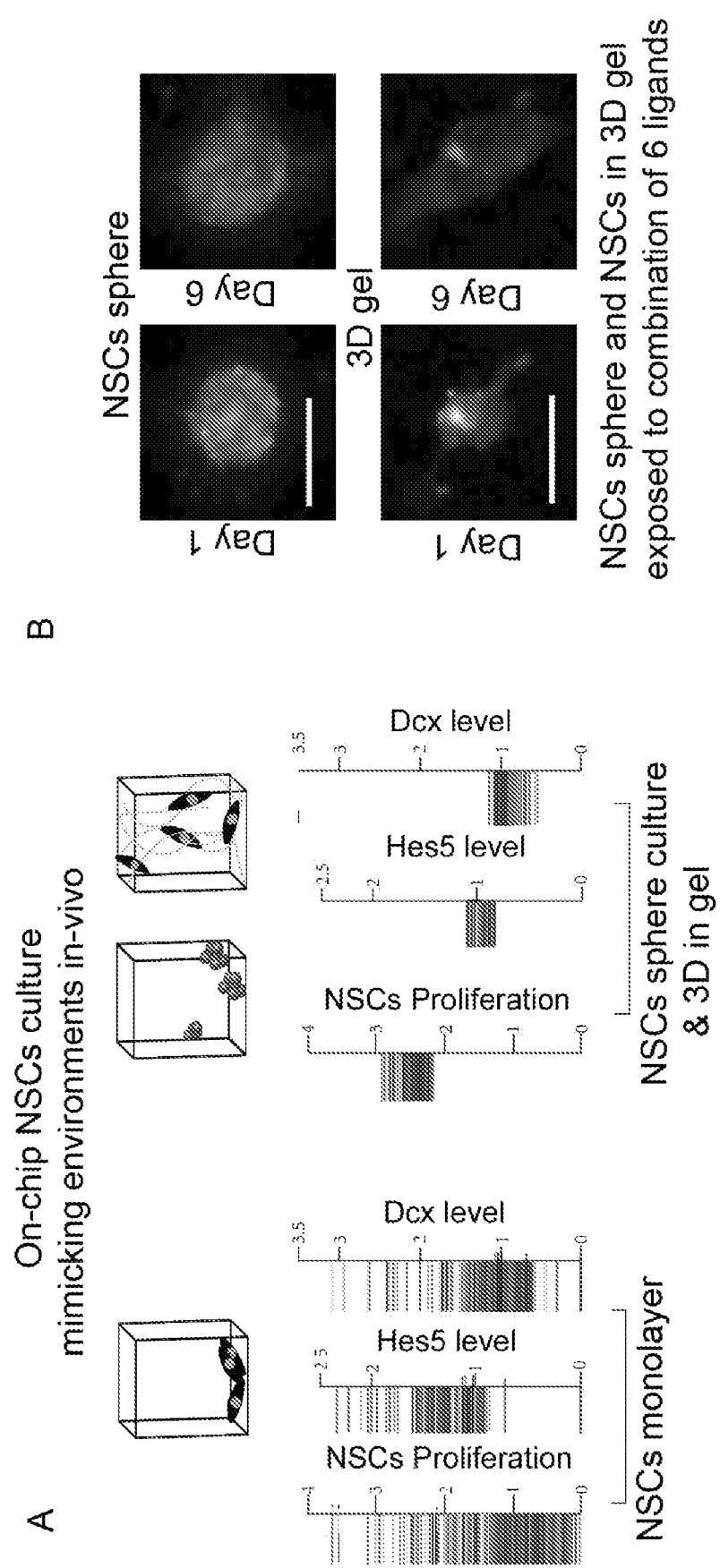
FIG. 19 depicts mammalian NSCs cell fate and forebrain development are directed by accommodating cell niches. The niche includes extracellular matrix factors, sequential, combinatorial and temporal ligand profiles, micro-confinement and cell-cell contact. These conditions are recapitulated in the present culture system using multimode culture (single cell, populations, and 3-D in gels), and combinatorial and dynamic delivery of signaling molecules. (A) Signal induced variations in NSCs cell count, Hes5-GFP and Dcx-RFP expression are plotted as bars indicating their intensities and values relative to the control experiments after 6 days of stimulation. The outcome of 2,400 experiments shows NSCs cell counts, Hes5 and Dcx level after 6 days of culture. NSCs adherent cell shows greater variation in all 3 categories as compared to neurospheres and 3D culture. (B) Fluorescence images of neurospheres and aggregates in 3D hydrogel after 6 days of stimulation with combination of all 6 ligands, Jagged, DLL, EGF, PACAP, CXCL, PDGF.
Figure 20:
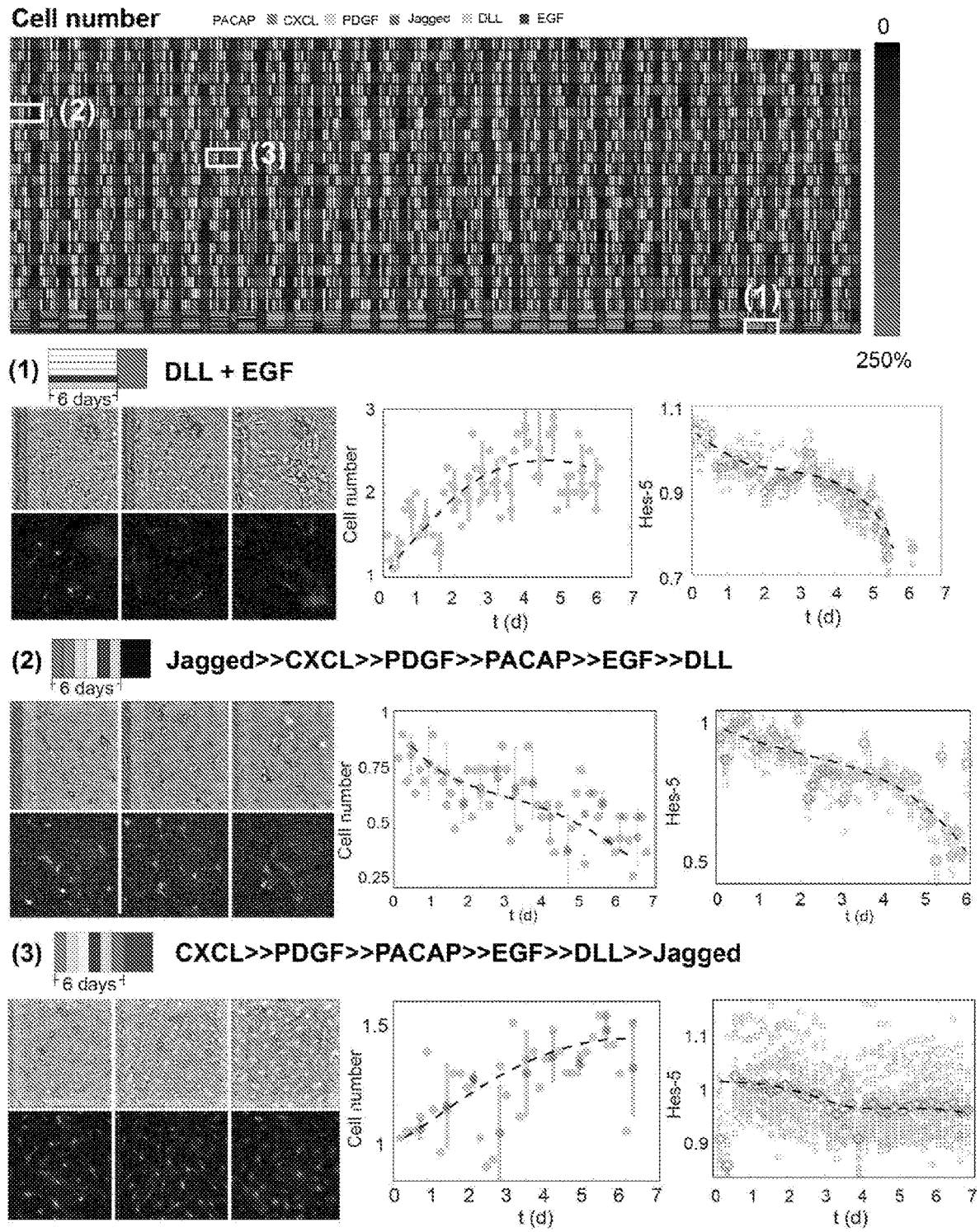
FIG. 20 depicts example data sets from one experiment. Signal induced NSCs cell count change at day-6 are plotted as color maps, together with the color-coded bars indicating the combinatorial and sequential signal inputs. The sampling ligands' combinations and sequences (including DLL and EGF, Jagged >>CXCL >>PDGF >>PACAP >>EGF >>DLL, CXCL >>PDGF >>PACAP >>EGF >>DLL >>Jagged) show the variations in cell proliferation and Hes5 expression dynamics. All cell images are 400 μm by 400 μm in area.
Figure 21:
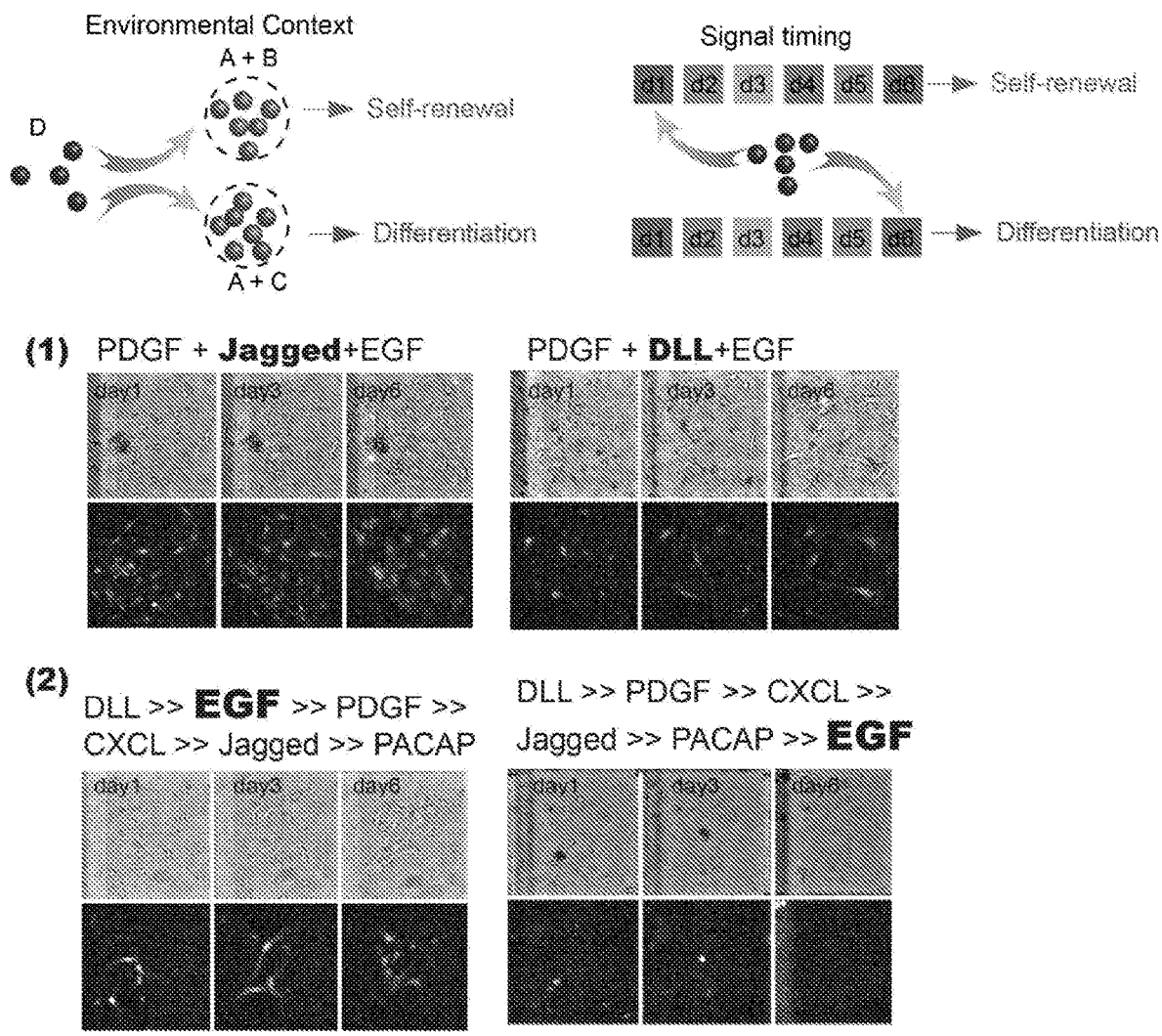
FIG. 21 depicts a schematic drawing showing the importance of environmental context and signaling timing in determining NSCs cell fate. The NSCs single cell tracking images, and dynamic changes in cell number and Hes5 level are plotted for two ligand combinations containing (Jagged, PDGF, EGF) and (DLL, PDGF, EGF); and 2 select ligands sequences (DLL >>EGF >>PDGF >>CXCL >>Jagged >>PACAP) and (DLL >>PDGF >>CXCL >>Jagged >>PACAP >>EGF). All cell images are 400 μm by 400 μm in area.

In certain embodiments, with 150 μm chamber height, NSCs spheres with diameters ranging from 10 to 100 μm are housed and allowed to grow. The diameter of the NSCs spheres doubles after 5-day culturing on chip, indicating an 8 times increase in cell number (FIG. 4B). In 3D hydrogel, despite that NSCs may adopt different morphologies, a similar growth rate is observed (FIG. 4C). In adherent culture, NSCs cell number doubles within the first 24 hours (FIGS. 13A-13C). However, the number of cells is approximately 150%-200% of initial number after 1-week incubation due to cells' migration in-and-out of the field of view.

Figure 5C:
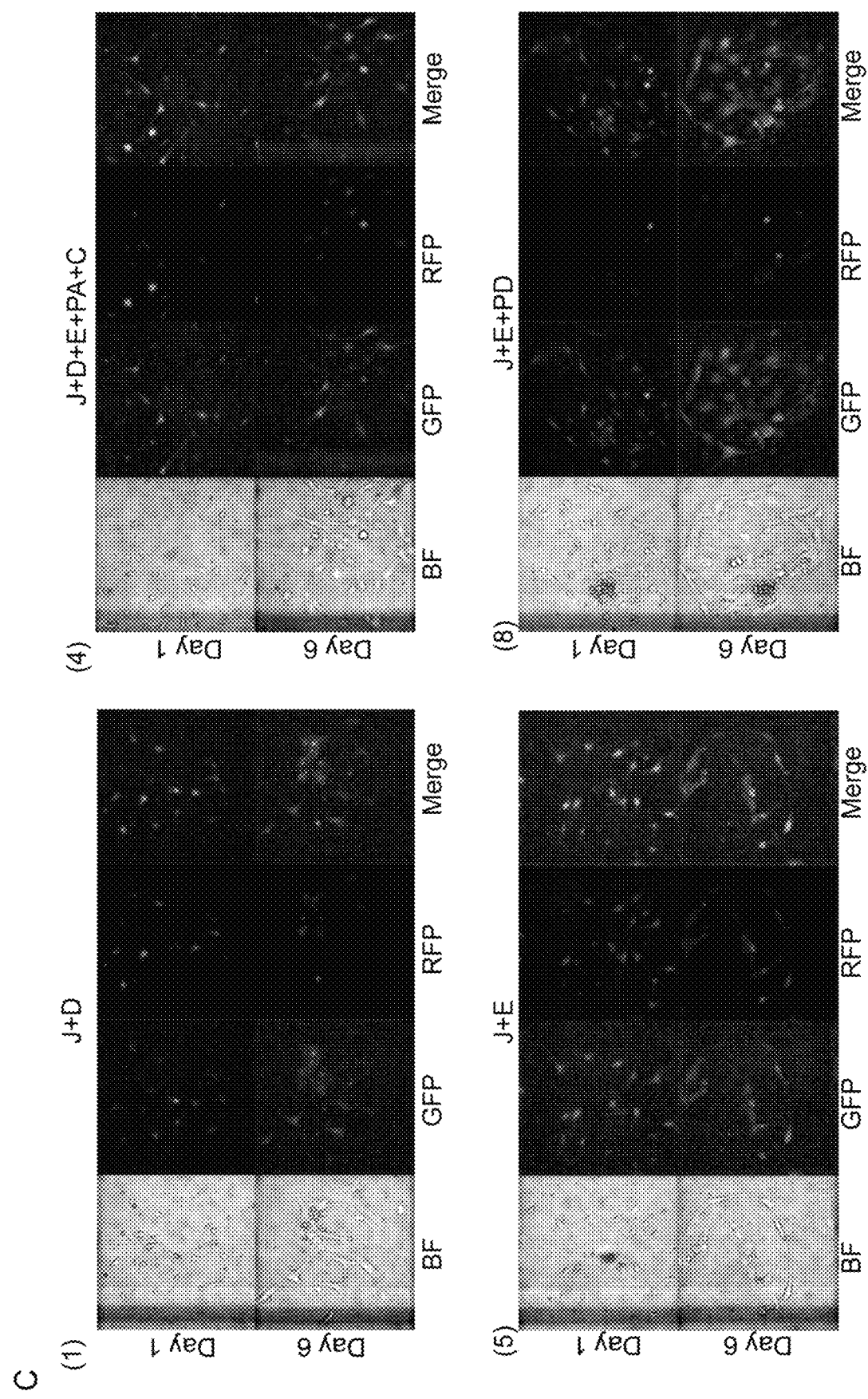

High-throughput independent chambers together with on-chip formulation of chemical inputs enable previously-intractable experiments mimicking complicated cellular environments (including dynamic ligand inputs). As a demonstration, 6 selected ligands that can bind to highly-expressed receptors during early embryonic forebrain development (PDGF-AA, PACAP, CXCL, EGF, Jagged, DLL) are introduced into designated chambers either as different combinations or time sequences (FIG. 5 and FIG. 22). Information on NSCs proliferation, Hes5 and Dcx expression level, and cell morphology is obtained through live cell imaging and automated single cell tracking and analysis. The inventors found that NSCs cell growth rate, Hes5 and Dcx level are not always correlated. These ligands, which are introduced to designated chambers in sequential and combinatorial manner, led to maintenance and growth of the stem cell pool in the present experiments. These findings are confirmed by the present experiment, in which the sole presence of ligand PDGF increases Hes5 level by around 25% from its initial value (FIG. 6). The few distinguished NSCs showing low growth rate and extended bipolar structure (~100 µm in size) are proven to be immature neurons through immunostaining (+beta-tubulin, +Hes5) (FIGS. 7B and 7C). Meanwhile, most NSCs remain a stem cell morphology (bipolar, ~50 µm), suggesting the positive effect of PDGF in NSCs self-renewal and NSCs heterogeneity. In contrast, all NSCs exposed to combination of all 6 ligands are +beta-tubulin and −Hes5. With morphologies carrying a bipolar structure with extended axons, these NSCs are most likely to be mature neurons (FIG. 7D) (Xiong, et al., 2014; Otify, et al., 2014). After exhausting all permutations of the 6 ligands, the sequences leading to high Hes5 expression and fast growth rate are identified through regression or classification tree analysis.

In summary, the high-throughput microfluidic device described herein creates a long-term stable, shear-free micro-environment that can be dynamically modulated when needed, and enables the study of both suspension and adherent cell types under complex but pre-programmable dynamic inputs. The inventors further demonstrate its versatility and capability by successfully cultivating various cell lines as well as extremely sensitive primary cells. With its capabilities of efficient on-chip mixing and chemical input formulation, the device is applicable to personalized therapy study by, for example, growing tumor organoids or immune cells extracted directly from patients and by performing drug screening. The device may be used to reconstruct the complex cellular environment with dynamic inputs and ultimately mimic various developmental stages of tissues and organs.

Experimental and Analytical Procedures

Design and Fabrication of Microfluidic Chips

The inventors designed and fabricated the microfluidic device according to the standard protocol, which is reported elsewhere (Unger, et al., 2000). Briefly, the inventors designed the two-layer device using AutoCAD (Autodesk Inc., San Rafael, CA, USA), and then printed the sketch on transparencies at 40 kdpi resolution (Fine Line Imaging, Minneapolis, USA). Molds for PDMS casting were produced using standard soft-lithography. The channel network of control layer as well as the flow channels for flow layer and culture chambers was produced with either SU-8 3025 or SU-8 3075 (Microchem, Westborough, MA, USA) on silicon wafers. For the flow layer, the inventors additionally used AZ-50X (AZ Electronic Materials, Luxembourg) at valve positions. Photoresists were spun to a height of 25 µm for channels, and 150 µm for culture chambers. To fabricate the chip, 72 g of PDMS (10:1 of monomer:catalyst ratio) was mixed, de-bubbled and poured over the Trimethylchlorosilane treated patterned silicon wafer. The PDMS was then cured for 60 min at 80° C. Following plasma and alignment between flow and control layer, inlet holes were then punched after two-hour thermal bonding. The chip was bonded to a PDMS coated coverslip and cured for at least 12 hours at 80° C. before use.

Chip Setup, Operation and Control

The glass slide carrying the microfluidic chip was cleaned and taped on a slide holder. Control channels were connected to miniature pneumatic solenoid valves (Festo, Switzerland) that were controlled with a custom MATLAB (MathWorks, US) through graphical user interface (Gomez, et al). Optimal closing pressures of push-up PDMS membrane valves were determined individually for each chip, typically ranging from 25 to 30 psi. The cell culture chambers were treated with either fibronectin (0.25 mg/mL; Millipore, Austria) for 3T3 cell culture or poly-lysine (0.01%, Sigma-Aldrich) followed by laminin (1 to 2 mg/ml, Sigma-Aldrich) for adherent NSCs culture. The remaining coating solution was flushed off from the chip using either PBS or cell culture media. Cell culture media is pre-warmed on chip for at least one hour before cell loading.

Cell Culture and Loading

For standard cell lines, the inventors used Jurkat cells, RAW 264.7 macrophages p65−/− with p65-GFP and H2B-dsRed, as well as NIH 3T3 p65−/− cells with p65-dsRed and H2B-GFP for tracking and analysis of NF-κB activation. These cells are cultured according to the established protocols (Lee, et al., 2014). To seed cells into the chip, adherent cells are harvested at 80% confluence with trypsin, re-suspended and loaded into chips through semi-automated loading program at cell density from $10^4$ to $10^6$ per milliliter depending on the desired cell density.

Murine hematopoietic stem cells (HSC) are isolated by FACSAria III flow cytometer (BD Biosciences) as Lin−/c-Kit+/Sca-1+/CD48−/CD150+/CD34− (lineage, Lin: CD3e/CD11b/CD19/CD41/B220/Gr-1/Ter-119), which are approximately 50% pure HSCs. Macrophage colony-stimulating factor (M-CSF), a myeloid cytokine released during infection and inflammation, is employed to induce HSCs differentiation. Human CD34+ cells were isolated from mononuclear cells using EasySepTM human CD34 positive selection kit (Stemcell Technologies, Vancouver, BC, Canada). CD34+CD38−CD45RA−CD90+CD49f+ HSCs were sorted using a FACSAria III flow cytometer (BD Biosciences). Pro- and anti-inflammatory cytokines including TNF, IFN☐, IL-6, IP10 and MCP-1 are introduced into the cellular environment as single ligand and in combination. Embryonic NSCs with Hes-GFP and Dcx-RFP reporters were isolated at embryonic day 13.5 from a transgenic mice carrying Hes-GFP and Dcx-RFP using standard protocol (Woo, et al., 2009; Basak, et al., 2007). The resulting primary cells were verified to carry both Hes5-GFP and Dcx-RFP after isolation and allowed to grow for few passages before use in the experiments (Giachino, et al., 2009). NSCs were cultured as neurospheres in culture media (DMEM/F12+Glutamax (Gibco No:31331-028); 10 U/ml penicillin; 10 ug/ml Streptomycin; B27 supplement (1:50); FGF growth factor 0.02 ug/ml). As NSCs are sensitive to environmental variations, cell handling protocol before loading into the chip is examined systematically (including dissociation, FACS sorting, etc.). To obtain the optimal results, NSCs spheres are collected and loaded into the chip 24 hours after fresh dissociation wherein each sphere contains ~7 to 10 cells. To avoid potential artifacts due to prolonged in vitro culture, only NSCs within 10 passages were used in the study. In control experiments, transferring chip-cultured NSCs to a well-plate shows the sphere-forming ability of Hes5-positive cells, validating Hes5 as a self-maintenance marker in the present experiments (FIGS. 12A-12B) (Behnan, et al., 2016).

The environmental conditions are maintained using temperature control and incubator system (Life Cell Imaging Service GmbH, Basel, Switzerland), which consists of a box surrounding the microscope, to strictly 37° C. and >98% humidity and 5% CO2 during the experiment, and the PDMS chip is covered with a stage-top-incubator connected to a humidifier and a gas exchanger.

Live-Cell Fluorescence Microscopy and Data Analysis

For image acquisition, a Nikon Ti-ECLIPSE microscope with an automated translation stage and a digital CMOS camera (ORCA-Flash 4.0, Hamamatsu, Japan) was used. The stage and image acquisition was controlled via the NIS Elements software. Bright field and fluorescence images were acquired and analyzed using a customized MATLAB program (Mathworks, Austin, USA). The algorithm extracts single cell traces including position, nuclear and cytoplasm fluorescence level. For example, the 3T3 cell nuclear area in each image is identified via the fluorescent nuclear marker GFP, and then the mean value of the nuclear intensity of the p65-DsRed marker is measured, and plotted as a function of time.

Signaling Logic Rules in Neural Stem Cell Differentiation and Self-Renewal

Cells operate in dynamic microenvironments where the type and concentration of signaling molecules are ever changing. The stem cell niche presents a range of signaling molecules and growth factors to maintain the stem cell pool. During development or injury, the chemical composition of the niche changes to allow differentiation into defined cell lineages. Signals received at different cell-fate decision points determine differentiation trajectories (Hemberger et al., 2009). It is highly desirable to recapitulate such dynamic signaling environments in experiments to study stem cell behavior quantitatively, as well as in tissue regeneration applications.

Current live-cell analysis techniques are severely limited in creating and controlling complex dynamical microenvironments. Microfluidic cell culture has been proposed to improve time-consuming and labor-intensive tasks by automating operations (Unger, 2000; Millet, et al., 2012; Lecault, et al., 2011; Sackmann, et al., 2014; Jeong, et al., 2015; Gomez-Sjoberg, et al., 2007; Mehling, et al., 2014), and to realize previously intractable experiments in dynamic cell culture (Jeong, et al., 2015). Individual devices for sorting, culturing, dynamically stimulating, imaging, tracking and retrieving cells have been demonstrated, however, none of the current systems combine these capabilities. Further, the number of individual dynamic culture conditions created in previous microfluidic devices has been limited to less than one hundred (Gomez-Sjoberg, et al., 2007), limiting their utility in screening a large number of conditions in exploratory signaling and drug studies. Additionally, maintaining long-term viable cultures of sensitive primary mammalian cells in microfluidic devices was so far elusive (Mehling, et al., 2014; Millet, et al.).

To address all of these limitations and to realize a universal system for dynamical cell control and analysis, the inventors developed an ultra-multiplexed microfluidic system that combines multi-mode cell culture (single cell, 2-D monolayer and in 3-D organoids), generation of dynamic chemical inputs, and 1,500 individually addressable cell culture units on a single device (FIG. 1). Each of the 1,500 culture chambers can be programmed to receive a different set of signaling molecules, growth factors, or drugs, whose composition and concentration can be automatically changed on-demand. Culture conditions including cell type, cell density, and support matrices can be predetermined for each independent chamber. Coupled with custom software for chip control and computational data processing, the system can perform programmed delivery of thousands of formulated fluidic inputs to designate on-chip culture units, while monitoring and analyzing cellular responses via live-cell microscopy and end-point biochemical analysis methods (FIG. 1D). In a typical 1-week long experiment, this system tracks ~30,000 individual cells cultured under 1,500 dynamic individual conditions by performing ~106 pipetting steps with nanoliter precision, and creates millions of single-cell data points. These are capabilities well beyond manual, robotic or other microfluidic systems in terms of labor, cost, and time.

Cultivating a broad range cells in dynamic microenvironments requires precise control of cell density, surface properties, support matrices, gas and fluidic exchange, media and growth factor delivery, and humidity. To realize this, the inventors designed a simple two-layer culture chamber that creates a consistent microenvironment for long-term cellular studies (FIG. 1B, 1C). The 3-D culture chamber can deliver media and ligands to cells via diffusion, preventing cells from undesirable shear stress and displacement in live-cell tracking experiments (FIGS. 1C, 1D, 1E and S1). The use of diffusion based media delivery is flow-free, gentle and creates minimal mechanical disturbance to the cellular microenvironment. The culture chamber can be loaded with gels and other support matrices to enable 3-D cell organization (FIG. 1C, 1E and FIG. S4). Furthermore, on-demand cell retrieval from designate chambers is possible by automatic switching to flow-based media delivery (FIG. 1C, S1). To formulate complex and dynamic chemical inputs on chip, the inventors designed and integrated a new microfluidic chemical formulator. A wide range of time-varying chemical inputs with distinct characteristics (i.e. pulsed and sinusoidal inputs) can be generated from a few previously prepared fluid vials connected to the chip, and can be delivered to live cells with sub-minute temporal resolution by diffusion, or with sub-second resolution by regulated flow (FIG. 1A).

The Achilles heel for microfluidic cell culture has been poor cell viability, which has been especially severe for sensitive primary mammalian cells (Mehling, et al., 2014; Millet, et al., 2007). To demonstrate general cell viability in the present system, the inventors first cultured mouse fibroblast cells and primary human hematopoietic stem cells (HSCs) in adherent and suspension culture modes, respectively, and stimulated them either with constant, pulsed or sinusoidal formulations of the inflammatory cytokine TNF to induce NF-κB signaling (Kellog, et al., 2015) (FIG. 1A, FIGS. 3A-3C, FIG. 11A, and FIG. 16). Dynamic stimulation and indexed tracking of non-adherent cells like HSCs was not feasible before the present study due to flow-based stimulation displacing cells and preventing single-cell tracking. The inventors stimulated human HSC's with different concentrations of TNF as well as in combinations with other cytokines (IFNγ, IL-6, IP10 and MCP-1), and with dynamic (time-dependent) variations of selected cytokines. Viability for various cell types was further demonstrated by culturing suspension cells including the Jurkat T cell line and mouse HSCs (FIG. 1E and FIG. 11A). In both cases, cells proliferated at similar, if not higher rates than those in bulk experiments in traditional culture dishes.

The inventors cultured primary mouse embryonic neural stem cells (NSCs) and stimulated them on the present chip for weeks under three distinct modes: suspension as single cell or as neurosphere, adherent monolayer, and 3D in hydrogels (FIG. 1E, 2, and FIGS. 12A-12B). The number of adherent NSCs increases by 50% after 24 hours, comparable to traditional well-plate culture. Meanwhile, the diameter of NSCs in suspension and 3D gel culture both doubled after 4 days of on-chip culture (FIG. 1E). NSCs differentiation and self-maintenance can be assessed at the single cell level via tracking of marker expression; Hes5-GFP of self-renewing NSCs and Dcx-RFP to label neuroblasts (Basak, et al., 2007; Haas, et al., 2010; Basak, et al., 2012; Sykova, et al., 2013; Behnan, et al., 2016).

Figures 6A, 6B:
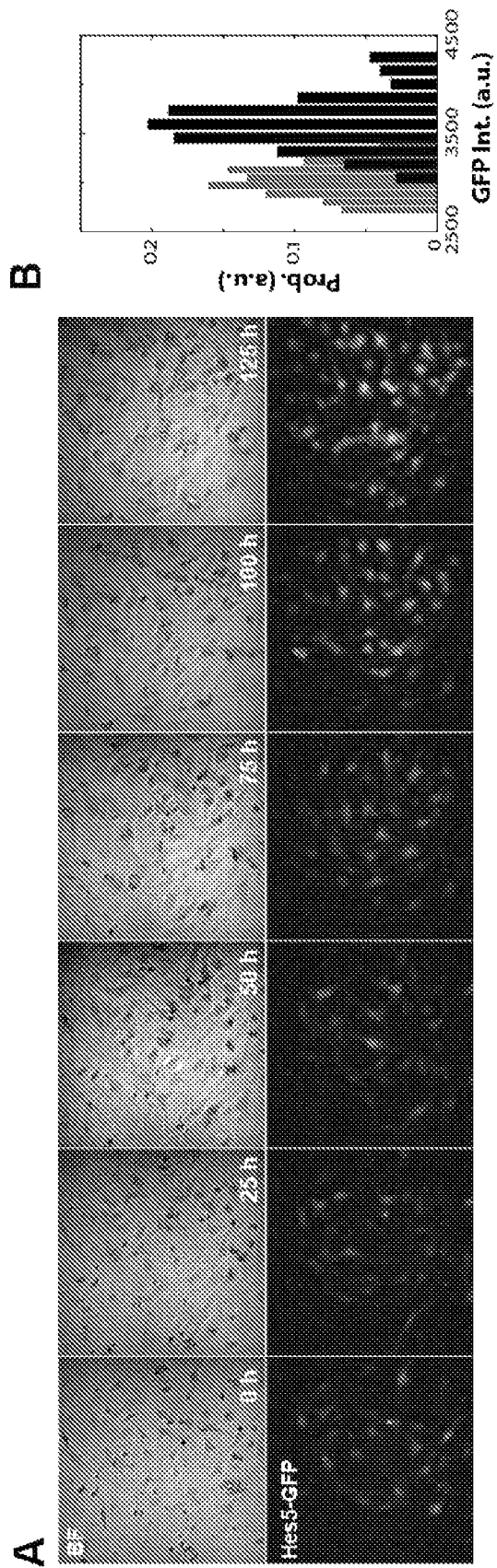
FIGS. 6A-6E depict high-throughput dynamical analysis of neural stem cell (NSC) differentiation. Millions of single-cell images are generated and automatically quantified in live-cell signaling factor stimulation measurements.

To study early signaling events during mammalian forebrain development in vitro, the inventors dynamically analyzed NSCs under combinatorial and time-varying signaling inputs in the present system (FIGS. 6A-6D and 8A-8E). The six selected signaling molecules were identified through RNA sequencing of NSCs isolated from embryonic mouse brain tissue, whose receptors are highly expressed during mouse forebrain development. These factors were Jagged1, DLL1, EGF, PACAP, CXCL and PDGF (Atlas, 2017). The effect of these ligands on NSC differentiation and self-maintenance is not well understood. The inventors hypothesized that the different combinations and temporal ordering of these ligands will lead to distinct cell fate outcomes. The inventors therefore generated thousands of combinations and temporal sequences of these ligands on the chip, and delivered them to NSCs cultured in different chambers while monitoring their differentiation and growth at the single cell level by time-lapse microscopy (FIG. 6A). Millions of single cell data points were generated and quantified in these experiments. The stimulation input conditions are summarized in FIGS. 22 and 23.

Figures 6C, 6D:
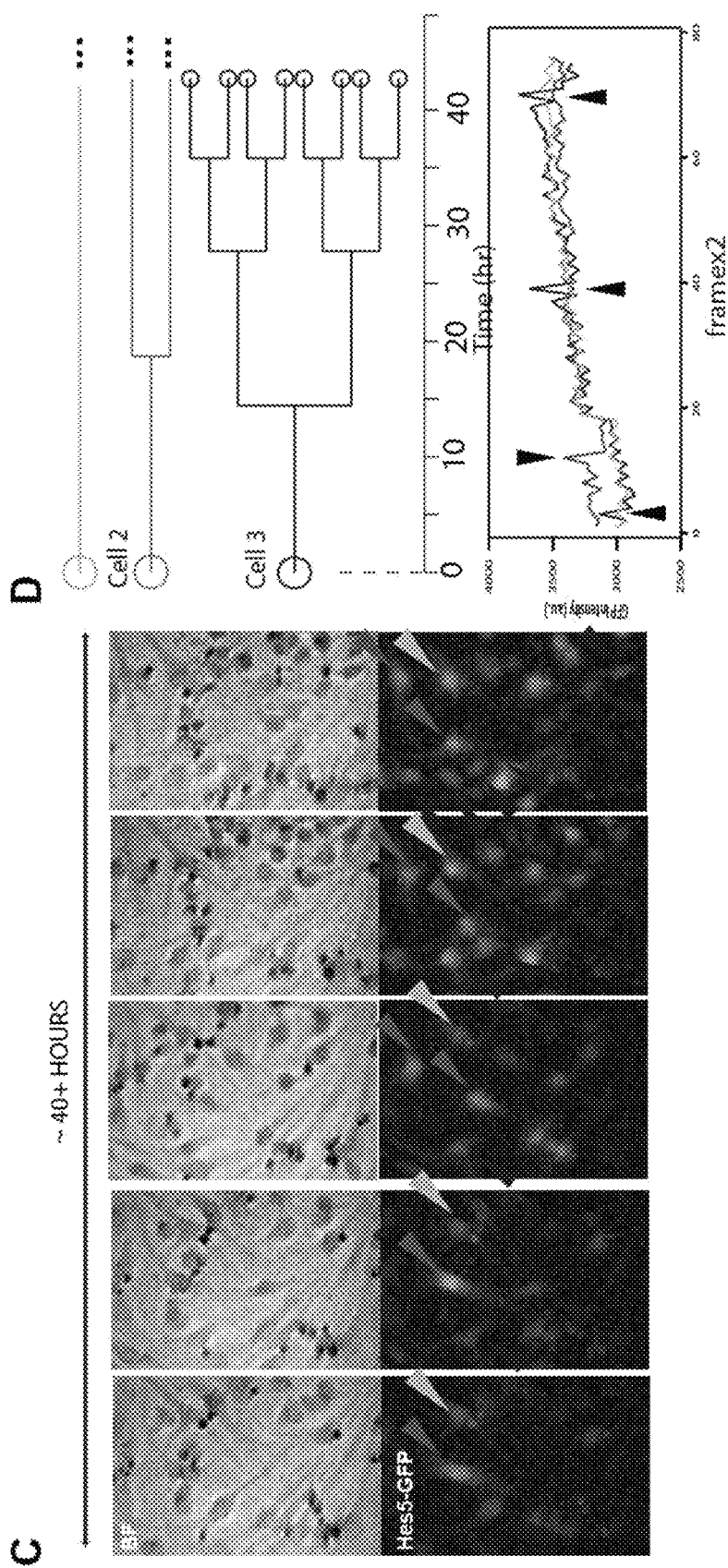
Figure 6E:
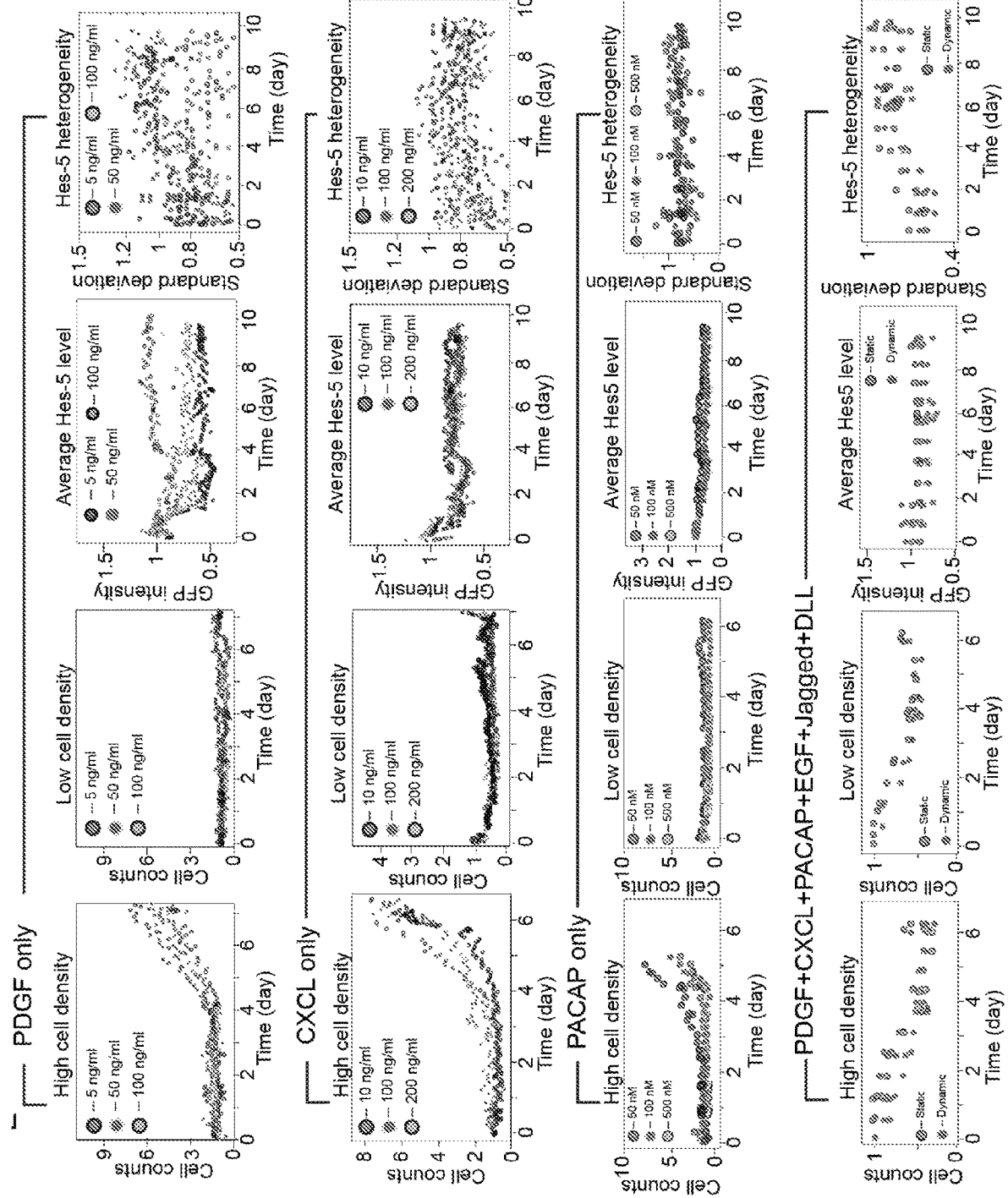
Figures 7A, 7B:
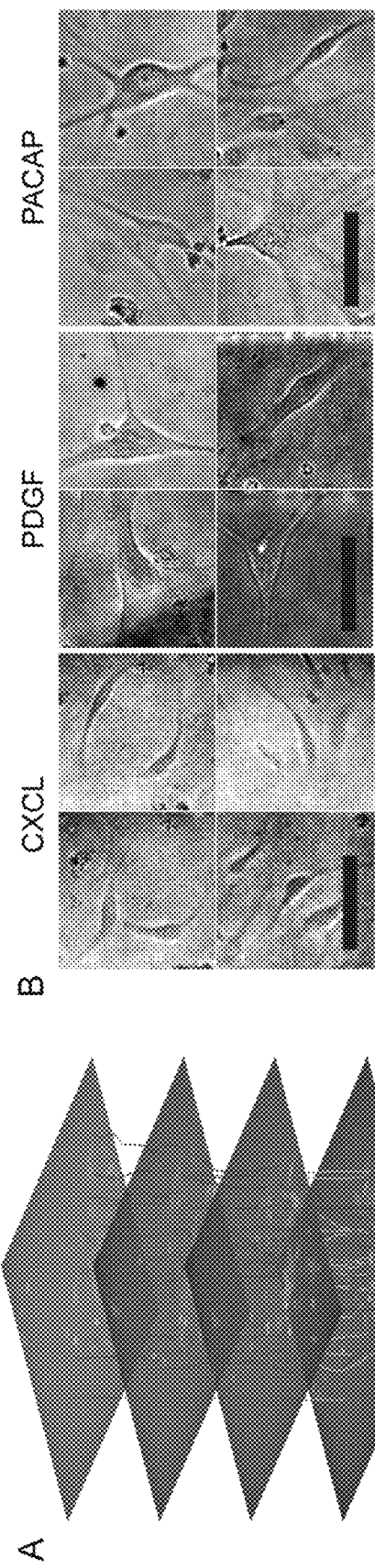
FIGS. 7A-7D illustrate features of the assessment of NSCs cellular state based on protein expression level, cell morphology and immunofluorescence.
Figure 7C:
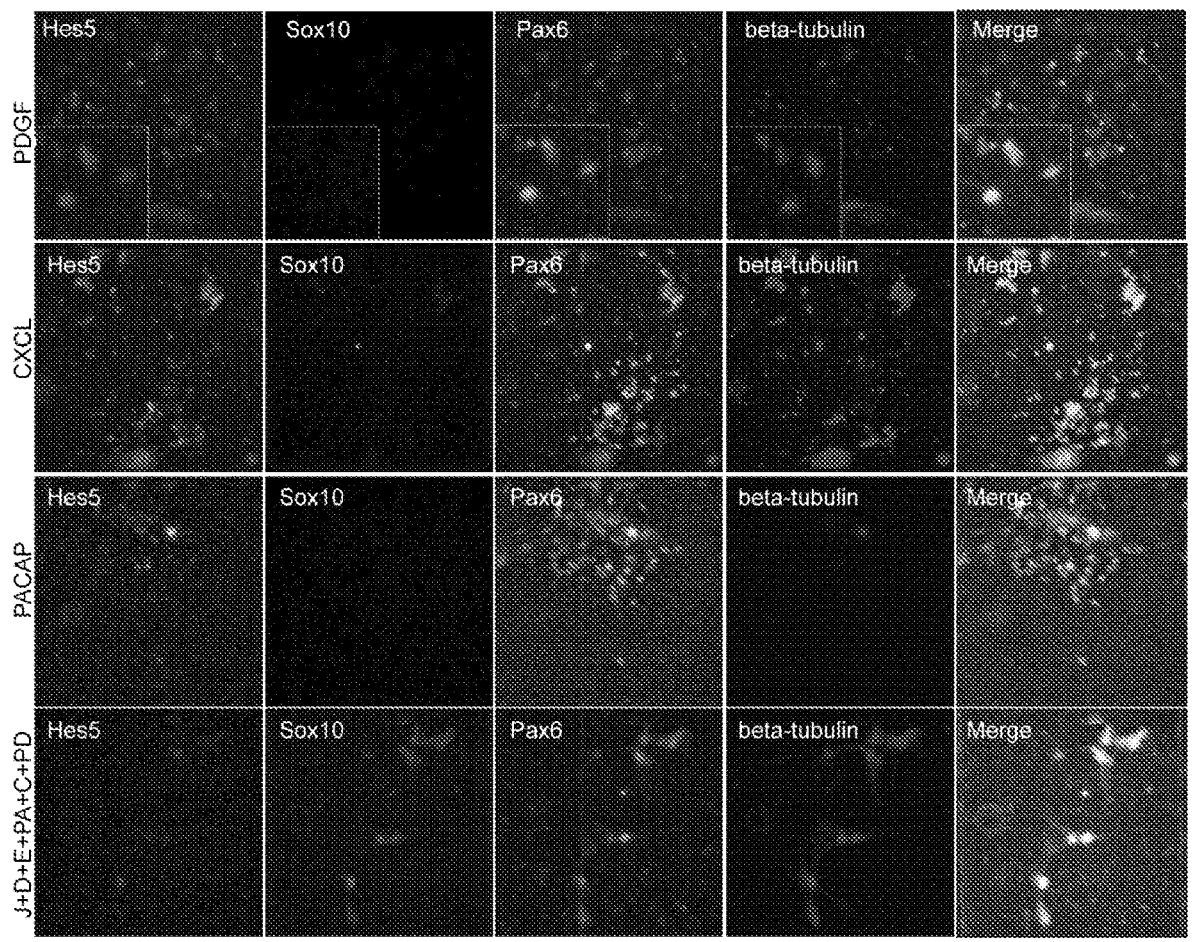
Figure 7D:
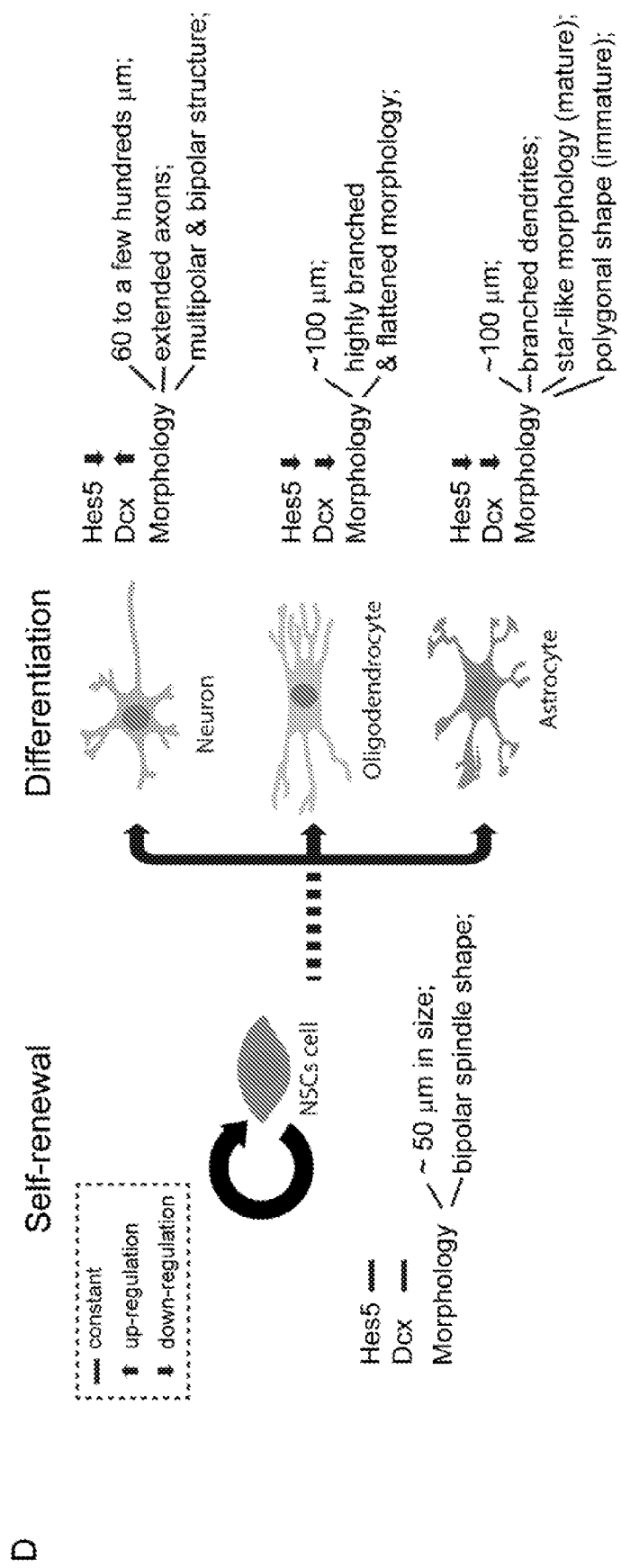

High Hes5 expression in NSCs indicates maintenance of the stem cell state, while reduced Hes5 indicates progression towards differentiation (Basak, et al., 2007). The inventors found many culture experiments where entire populations progressed towards differentiation (FIG. 6A-6C). Nevertheless, there is significant variability at the single cell level in a given culture condition (FIG. 6C-6E). Distinct proliferation patterns were observed in spite of similar Hes5-GFP levels (FIG. 6D, 6E). Overall, NSCs proliferate at different rates depending on initial cell density, with higher densities leading to higher proliferation rates (FIG. 6E). Mean Hes5 expression levels and single-cell heterogeneity strongly depended on the signaling inputs received by each NSC culture.

Figure 8A:
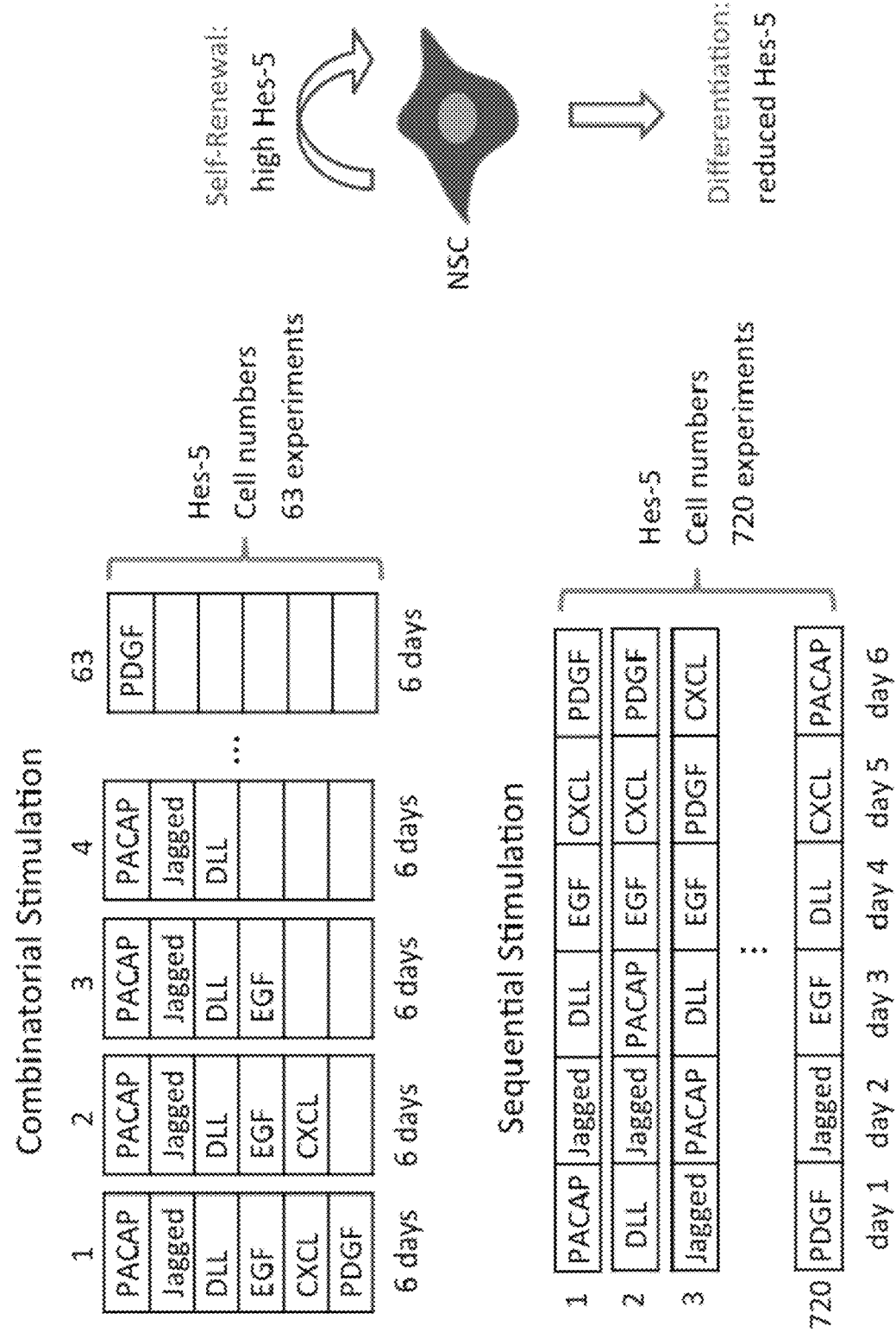
Figure 8B:
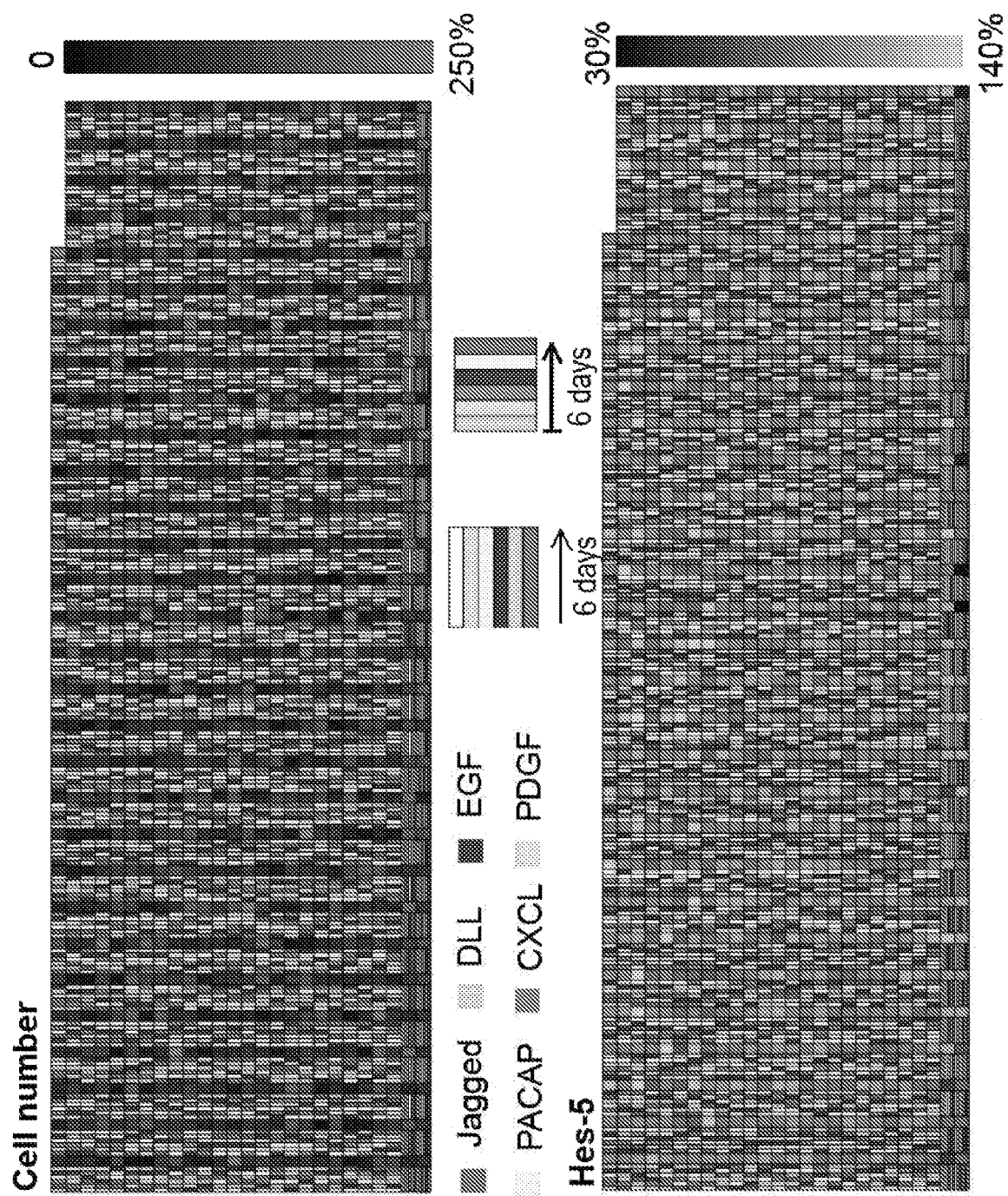

To investigate the role of combinatorial or temporal ordering of signals in NSC differentiation, the inventors cultured NSCs under combinatorial and sequential applications of the six regulatory ligands (FIG. 8A, FIGS. 22 and 23). For each independent NSC culture on the chip, the inventors introduced either one ligand each day (sequential inputs), or a combination of the selected ligands over a six-day period (combinatorial inputs). The inventors measured the ratio of the ligand-treated cells to untreated control for cell number and Hes5-GFP expression intensity. Each chip experiment consisted of 63 combinatorial and 720 sequential stimulation experiments, with duplicates (FIG. 8B). Multiple experiments were repeated resulting in nearly 3000 dynamic cultures analyzed. The inventors subjected all experimental outputs of NSC cell numbers and Hes5 expression to regression and classification tree analyses. NSCs' cellular states were categorized into two groups: differentiation (with decreased Hes5 level and cell numbers) and self-renewal (with increased Hes5 level and cell numbers) (FIG. 8D).

Figures 2, 8C:
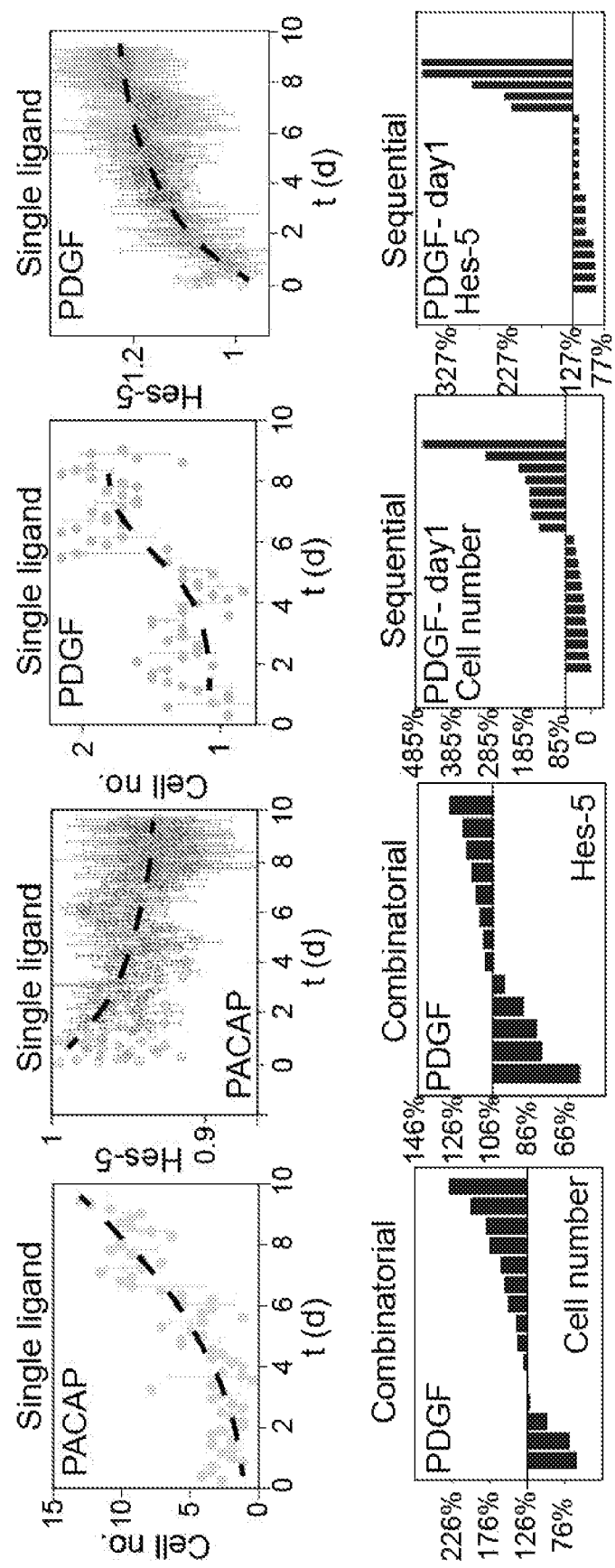

The inventors' computational analysis revealed the overall role of each ligand in hundreds of complex experiments (FIG. 8C). In single ligand experiments, cells were stimulated with only one ligand and cell numbers and Hes5 levels were recorded. In combinatorial and sequential stimulation experiments, the ligands of interest were present in a complex mixture of other ligands, and the inventors identified its overall effect by averaging over groups of experiments. The role of each ligand depended on whether it was delivered alone, or in combination with other ligands. The variation between individual experiments using the same ligand indicated that the role of a ligand is highly context dependent, and the presence of other ligands can switch the role of that signaling molecule. For example, PACAP leads to decreased cell numbers in certain combinatorial experiments, but it also leads to increased cell numbers in other combinations, depending on its partner ligands (FIG. 8C). Similar role-switching behavior was also seen on Hes5 expression under PDGF stimulation.

Figures 2, 8D:
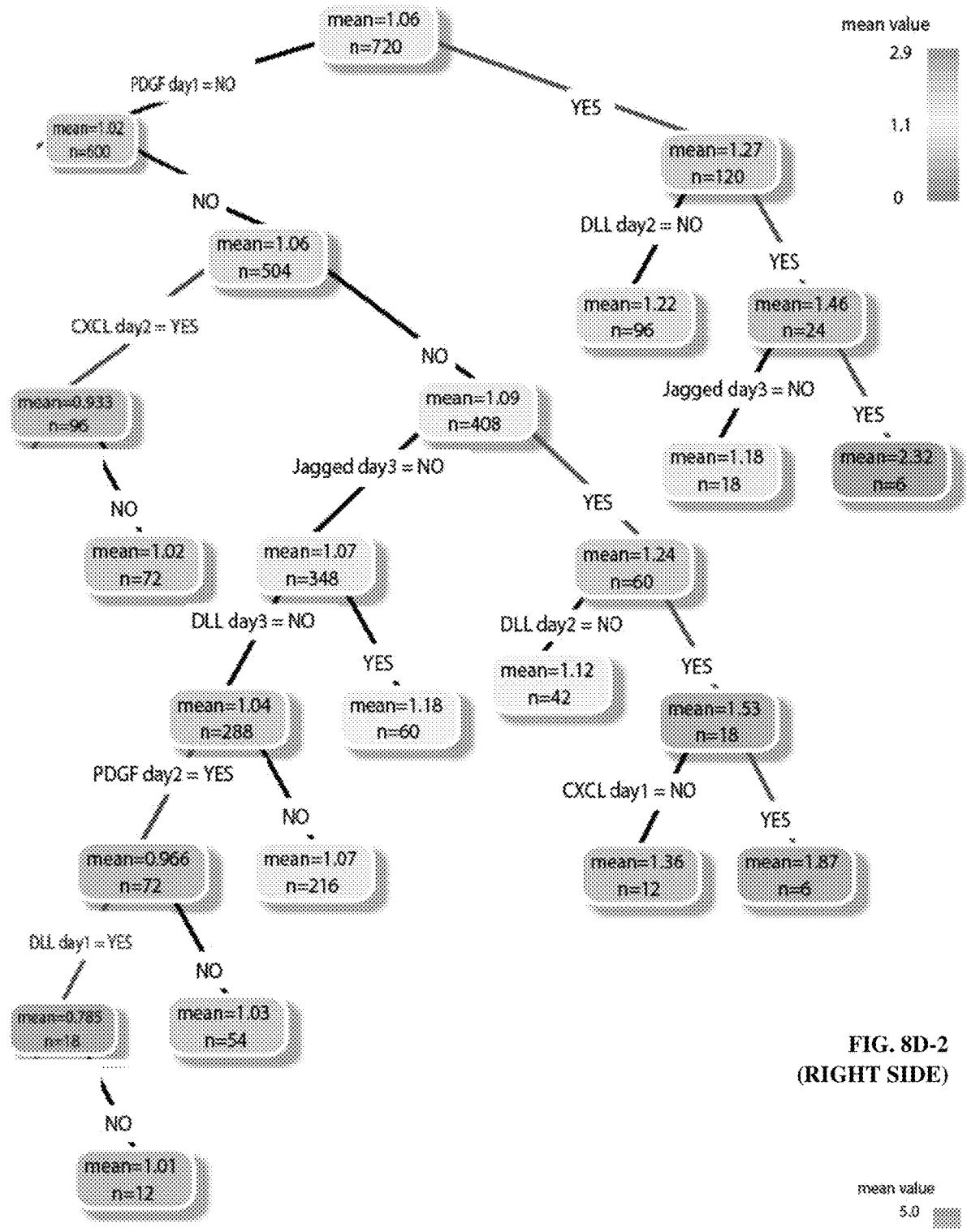

Decision tree analysis, described in more detail below, resulted in distinct and nontrivial "cellular logic rules" leading to the two cell fate outcomes (FIG. 8D, 8E, and FIG. 18). For example, the inventors found that the simple presence of PACAP or PDGF on the 1st day of culture was enough to drive high cell proliferation or high Hes5 expression levels, respectively. Another notable and rather complex input sequence leading to higher cell proliferation includes [Jagged at day 1, EGF at day 2, CXCL at day 4]. On the other hand, input sequences such as [DLL at day 1] or [EGF at day 1, PACAP at day 2] were found to preferentially cause differentiation. The existence of both simple and complex rules leading to the same outcome indicates redundancy in signaling pathways controlling cell fate decisions.

The summary of signaling principles in NSCs differentiation and self-maintenance, as uncovered by dynamical single-cell culture and decision tree analysis, is described in FIG. 9A-9H. These principles pertaining to the role of signaling inputs first highlight the importance of the environmental context and signal timing in NSC differentiation. For example, NSCs are directed to either self-renewal (high Hes5 expression) or differentiation (low Hes5 expression) by changing only one ligand within the combination (Jagged to DLL, FIG. 9A). Similarly, changing the temporal order of a single ligand can direct NSCs to different cell fates (FIG. 9B): delivering EGF on day 2 led to high Hes5 expression levels and unchanged cell numbers indicating maintenance of the stem cell pool, whereas moving the application of EGF to day 6 led to a significant reduction in Hes5 expression indicative of differentiation.

Figure 9A:
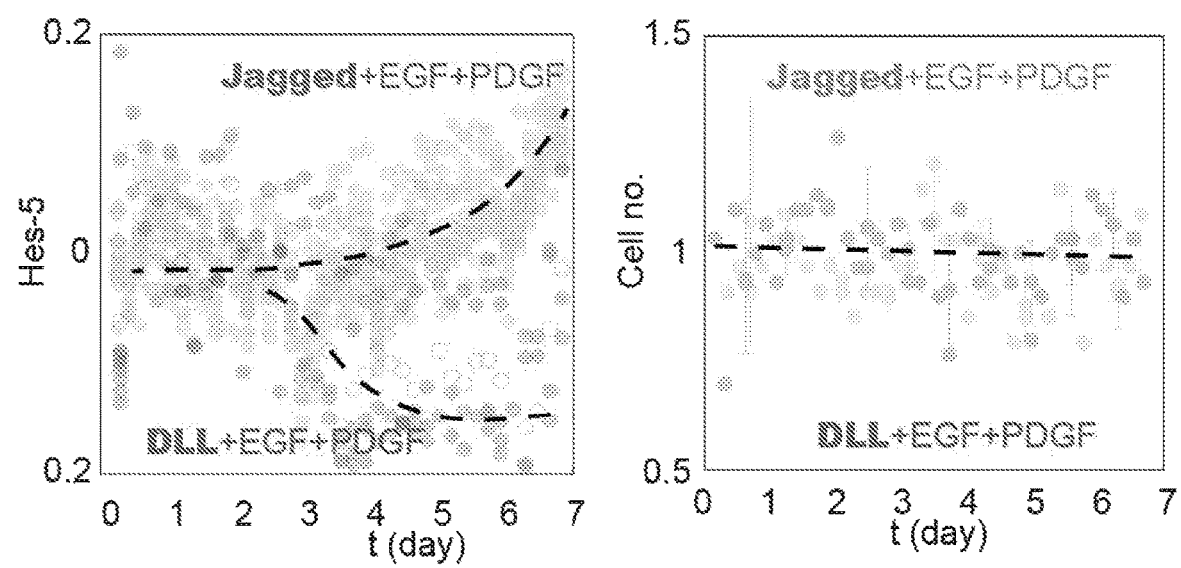
Figure 9B:
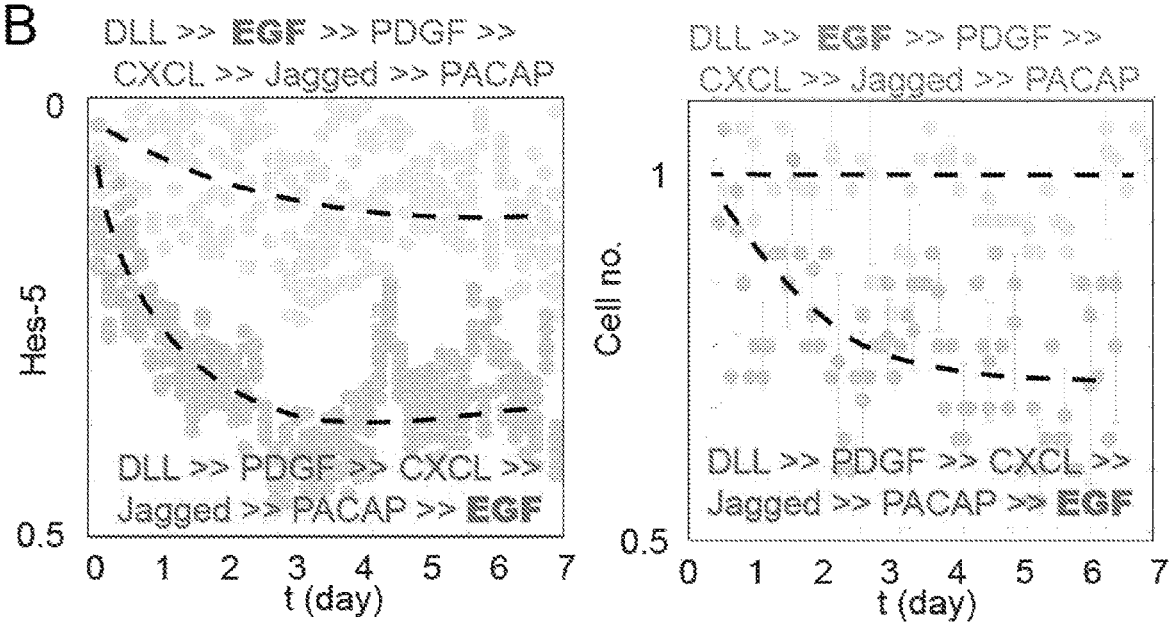
Figures 9C, 9D:
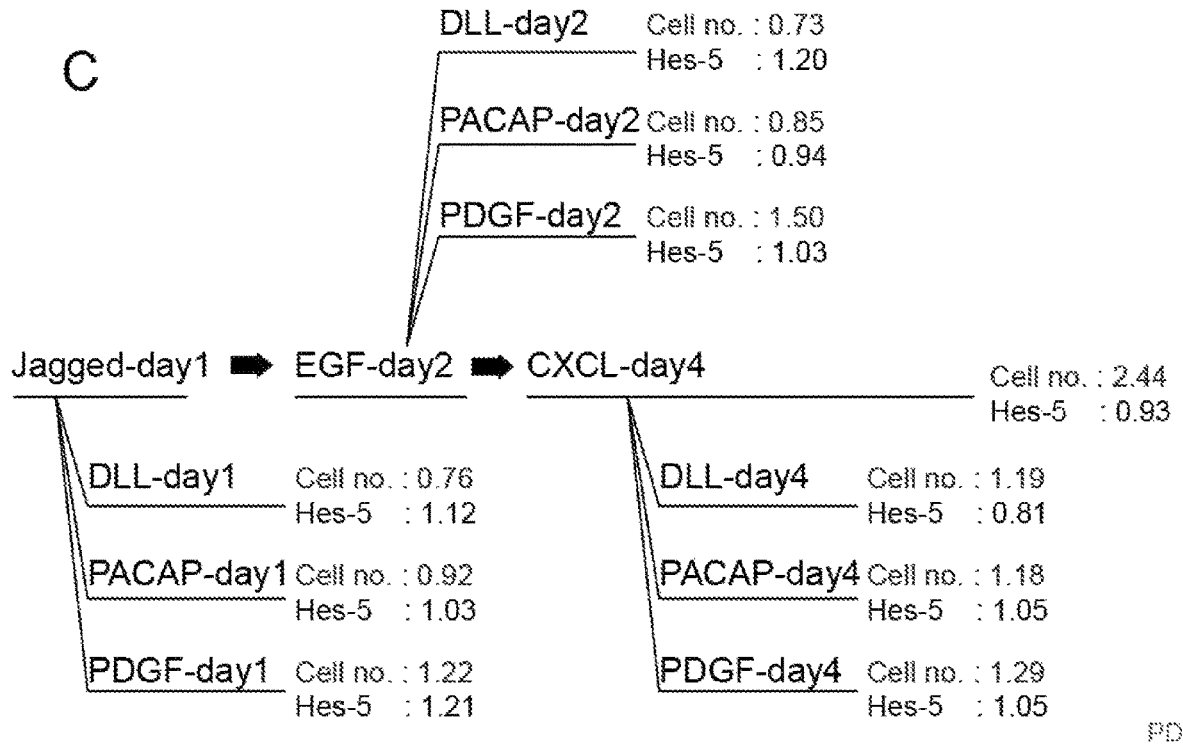

Decision-tree analysis of sequential stimulation experiments showed that there are optimal signaling routes to different outcomes. For example, the optimal route of signal input sequence leading to NSCs self-renewal was found to be Jagged (day 1) >>EGF (day2) >>CXCL (day4). Any deviation from this route (i.e. changing the ligand order) led to a reduction in the corresponding effect (FIG. 9C). The inventors also found that many signaling molecules show synergistic or antagonistic effects on NSCs proliferation or Hes5 expression (FIG. 9C). The combination of any 2 ligands may lead to either enhanced (synergistic) or reduced (antagonistic) effects compared to experiments that use these ligands in isolation. For example, experiments with DLL+ EGF induce an increased cell number of 250%, more than the total of experiments that used only DLL or EGF (100% and 60%, respectively).

Figures 1, 9E:
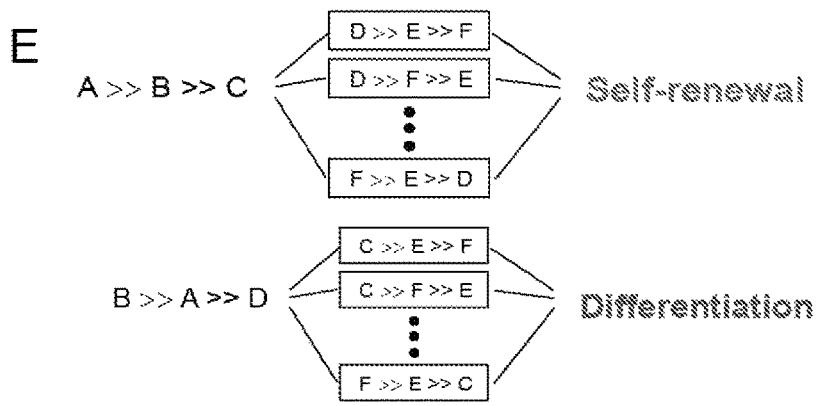
Figures 2, 9E:
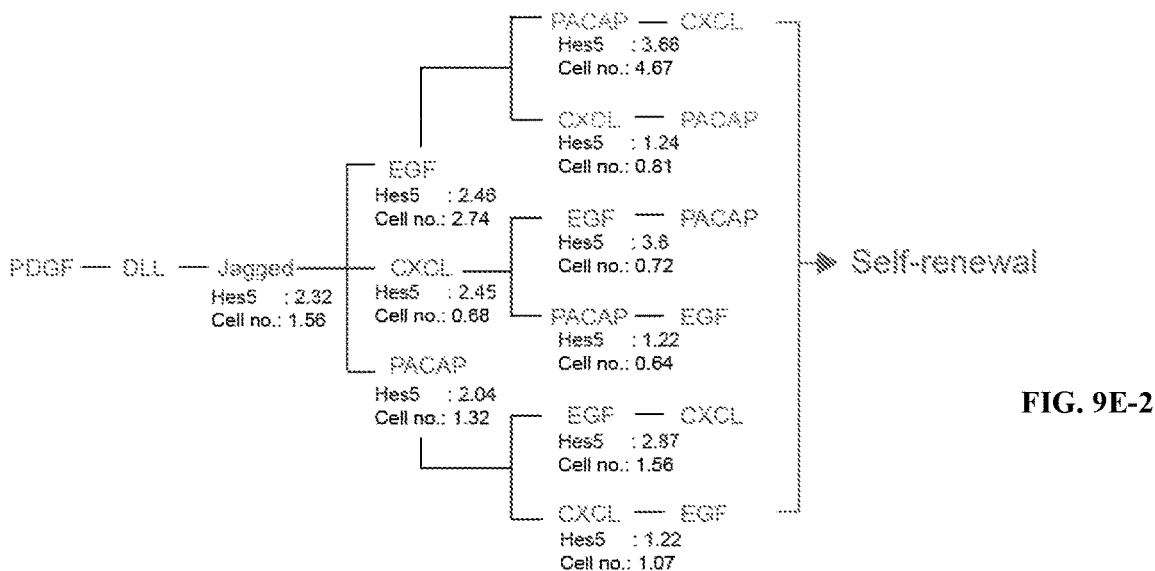
Figures 3, 9E:
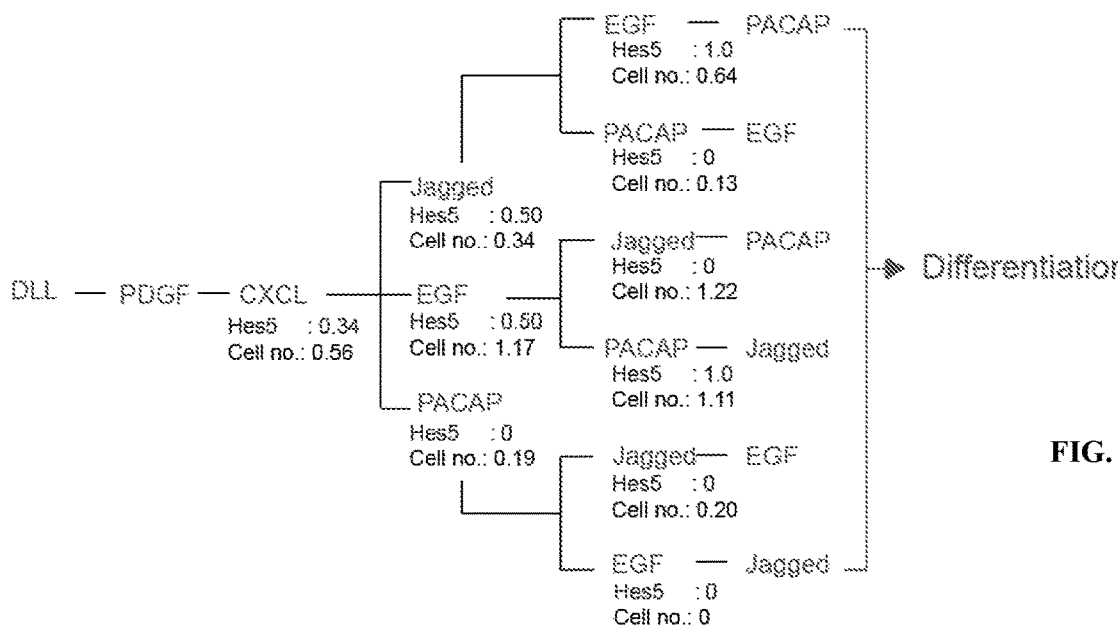

Another principle that emerged from the inventors' analysis was cellular commitment. Under specific inputs, the inventors found that cells at various decision points committed towards to either differentiation or self-renewal, and ignored the signals that come came afterwards. FIG. 9E shows actual input sequences that indicate commitment for self-renewal and differentiation. For example, after cells received PDGF-DLL-Jagged, all other signal combinations lead to high Hes5 expression and high cell numbers, indicating maintenance of the stem cell state. Similarly, after delivery of DLL-PDGF-CXCL, most signal combinations lead to low Hes5 expression and low cell numbers indicating differentiation. Therefore, the inventors found that under certain stimulation conditions NSCs cell fate can be determined mostly by the sequence of ligand inputs within the first 3 days of culture, and the inputs received during the last 3 days do not change the determined cell fate.

The inventors also found that signaling molecules can act bi-directionally on stem cell fate, and the exact role of a given signaling molecule is determined by either timing of that molecule, or by its pre-conditions (FIG. 9F). For example, PDGF introduced on the day-1 leads to NSCs self-renewal in most sequential experiments. However, moving PDGF to day-2 and introducing DLL in day-1 switches the role of PDGF and leads to promoting differentiation. A similar bi-directionality was also found for signaling molecules CXCL, and PDGF.

The inventors found that increasing environmental complexity (i.e. increasing the number of ligands) generally suppressed NSCs proliferation, however, reducing the input complexity enhanced the stem cell pool (FIG. 9G). Including more ligands in either in combination or sequentially led to an overall reduction of the proliferation rate compared to control, while the Hes5 expression levels remained relatively unchanged. This finding indicates that if the signaling environment becomes increasingly complex, stem cells commit and differentiate. Finally, the inventors' analyses reveal that signaling pathways that promote self-renewal and differentiation are highly redundant reflecting the intrinsic flexibility of stem cells to respond to their dynamic environment and niche (FIG. 9H). The inventors find multiple combinatorial and sequential input conditions that lead to the same cell fate (for example, similar Hes5 level and cell numbers at day 6), which suggests redundancy in NSC signaling.

In this study, the inventors present an ultra-multiplexed microfluidic technology with unprecedented capabilities for high-throughput live cell analysis under complex and dynamic signals. In record-breaking fashion, the present microfluidic system mapped the signaling landscape of NSC differentiation in 3,000 distinct microenvironments that mimic the dynamical stem cell niche. By computational and statistical analyses of thousands of live-cell experiments, the inventors identified cellular decision points and differentiation trajectories. The present microfluidic system greatly shortens the time-span and improves the reproducibility of high-throughput screening processes with live cells. This technology allows the analysis of unprecedented combinatorial complexity, which may have relevance for the dynamic and regulated microenvironment of the tissue during homeostasis and regeneration.

Decision Tree Analysis

In this work, the inventors use decision tree analysis to generate descriptive and predictive models which map measurements about cell phenotypic features (i.e., cell count and Hes5-GFP expression) to experimental conditions (i.e., sequential and combinatorial application of six regulatory ligands) (Breiman, 1984). The built decision trees partition the data space recursively according to evolving decisions on current best split (Therneau, et al. 2017).

Here, variance $Var(X)$ is used as a measure of heterogeneity for the dataset $X$ with n samples, which can be formulated as:

$$Var(X) = \frac{1}{n^2}\sum_{i=1}^{n}\sum_{j=1}^{n}\frac{1}{2}(x_i - x_j)^2.$$

From the parental to the children sets, the goal is to reduce the variance as much as possible. The inventors quantify the change in variance from a prior state to a state given a decision attribute $\alpha$ (i.e., the choice of experimental conditions) using Variance Reduction $VR(X, \alpha)$ as shown in the equation:

$$VR(X,\alpha) = Var(X) - Var(X|\alpha)$$

The decision attribute coming with the largest VR value is deemed to be a dominant factor. One can select the 'best' split accordingly, in which the reduction of variance is maximal and the most significant change in NSCs status is observed, by comparing the resulting VR values for all possible decision attributes. For example, in this study, the decisions are True/False statements on the presence of 6 ligands—Jagged, DLL, EGF, PACAP, CXCL, PDGF (combinatorial inputs) and the sequence of ligand additions with time coordinates assigned (sequential inputs). Based on the model, the inventors can identify casual factors that determine the fate of NSCs: self-renewal, proliferation and differentiation.

Decision tree results were cross-validated 10 times by R rpart package and at each time 1/10 of the data are randomly selected and held for validating the prediction accuracy. The R rpart implementation first fits a fully grown tree on the entire data D with T terminal nodes. After this step, the tree is pruned to the smallest tree with lowest miss-classification loss. The following steps are implemented:

1. The data is split into n (default=10) randomly selected folds: F1 to F10
2. It then uses 10-fold cross-validation and fits each sub-tree T1 . . . Tm on each training fold Ds.
3. The corresponding miss-classification loss (risk) Rm for each sub-tree is then calculated by comparing the class predicted for the validation fold vs. actual class; and this risk value for each sub-tree is summed up for all folds.
4. The complexity parameter $\beta$ giving the lowest total risk over the whole dataset is finally selected.
5. The full data is then fit using this complexity parameter and this tree is selected as the best trimmed tree.

Permutation Test

One-tailed permutation test is used to examine statistical significance ($p<0.05$ and relative increase of means >5%, or $p<0.05$ and relative decrease of means >5%) of biological findings under sequential and combinatorial inputs, and it builds (rather than assumes) sampling distribution through bootstrapping (Good, 2005).

Permutation Test and Decision Tree Analysis of Sequential Inputs on NSCs Hes-5 Level The effect of ligands on NSCs fate decision is dynamically sampled and integrated temporally within the reconstructed micro-environment, which is composed of architectural (e.g. surface, ECM, etc.) and other participating molecules throughout the developmental process. By tracking averaged NSCs Hes5 and Dcx level, as well as proliferation results within the categorized groups from the present dynamic input experiment, the inventors found rather complex but intriguing patterns individual ligands possesses on NSCs' differentiation and self-renewal. Below shows the list of individual ligands' effect based on NSCs Hes5 expression in the present sequential input experiment.

1.1. DLL tends to drive NSC to self-renewal, but it requires favorable pre-conditions:

Evidence a: Adding DLL at day 1 makes no significant impact;

Evidence b: With CXCL or PDGF added at day 1, applying DLL on the following day increases Hes5 expression considerably by a factor of 1.10 or 1.16.

1.2. The function of Jagged can be bi-directional, depending on pre-conditions:

Evidence a: Adding Jagged at day 1 decreases Hes5 expression to 94.5% of the control, driving NSCs to differentiation;

Evidence b: However, Jagged will turn to enhance Hes5 expression, as long as DLL is added before Jagged in the first 3 days, no matter which scenarios as follows: DLL day 1→Jagged day2; DLL day 1→any other ligands day 2→Jagged day 3; any other ligands day 1→DLL day2→Jagged day 3. These suggest that DLL can reshape Jagged's role played in Hes5-expression.

1.3. EGF exerts differentiation-preferable influence, if applied on the first day:

Evidence a: Adding EGF at day 1 decreases Hes5 expression to 86.8% of the control level, the largest reduction seen in all 6 ligands if applied at day 1, driving NSC to differentiation.

1.4. PACAP's inhibitory effect on Hes5 expression is conditional:

Evidence a: Adding PACAP at day 1 makes no significant impact;

Evidence b: With EGF added at day 1, the Hes5 expression would drop dramatically to 17.7% of the control level, if PACAP is given on the following day, strongly driving NSCs to differentiation;

1.5. CXCL can also function in two directions given different pre-conditions:

Evidence a: Adding CXCL at day 1 increases Hes5 expression to 117.7% of the control level, favoring self-renewal;

Evidence b: However, adding Jagged at day 1, which drives NSC to differentiation, also steers CXCL, if applied on the next day, to function in the same way, decreasing the Hes5 expression to 68.1% of the control level.

1.6. Similarly, PDGF is also bi-functional:

Evidence a: Adding PDGF at day 1 increases the Hes5 expression to 126.6% of the control level, the largest increase seen in all 6 ligands if applied at day 1, strongly favoring self-renewal;

Evidence b: Its role turns to be opposite if applied at day 2 with DLL added at day 1, and the Hes5 expression drops to 89.2% of the control level.

Below are the routes obtained through decision tree analysis leading to largest increase/decrease of Hes5 expression:

2.1. The route "PDGF at day 1→DLL at day 2→Jagged at day 3" leads to a monotonic increase of Hes5 expression, and its mean ratio relative to control raises incrementally from 1.06 to 1.27, 1.46 and 2.32 (as shown in FIG. 8D);

2.2. The route "CXCL at day 1→DLL at day 2→Jagged at day 3" also leads to a monotonic increase of Hes5 expression till 1.87 times of the control level (as shown in FIG. 8D);

2.3. On the other hand, the route "EGF at day 1→PACAP at day 2" leads to a monotonic decrease of Hes5 expression till 17.7% of the control level, strongly driving NSCs to differentiation (as shown in FIG. 8D);

2.4. The route "Jagged at day 1→CXCL at day 2" leads to a monotonic decrease of Hes5 expression till 68.1% of the control level (as shown in FIG. 8D);

2.5. Finally, the route "DLL at day 1→PDGF at day 2→CXCL at day 3 leads to a monotonic decrease of Hes5 expression till 33.5% of the control level (as shown in FIG. 8D).

Permutation Test and Decision Tree Analysis of Sequential Inputs on NSCs Proliferation NSCs proliferation, as another character for stemness, is subjected to the same decision tree and perturbation test as well. Ligands, which are capable of promoting and inhibiting NSCs proliferation, are defined as 'activator' and 'inhibitor', respectively. The obtained single ligands effect and cellular rules are listed below:

1.1. Activator: Jagged

Evidence a: Adding Jagged at day 1 increases cell number to 111.0% of the control.

1.2. Inhibitor: DLL and PDGF

Evidence a: Adding DLL at day 1 decreases cell number to 90.0% of the control level.

Evidence b: Adding PDGF at day 1 decreases cell number to 85.4% of the control level.

1.3. Conditional activator: EGF

Evidence a: Adding EGF at day 1 alone does not introduce significant increase of cell number;

Evidence b: On top of added Jagged or CXCL at day 1, adding EGF at day 2 further raises cell number by a factor of 1.38 or 1.19.

1.4. Conditional and bi-directional: CXCL

Evidence a: Adding CXCL at day 1 alone does not introduce significant increase of cell number;

Evidence b: With EGF added at day 1, introducing CXCL on the following day would increases cell number by a factor of 1.20.

Evidence c: Whereas if DLL and PDGF are applied on the first two days, CXCL would exert proliferation-inhibitory effect if added at day 3, and the cell number is thus reduced to 56.9% of the control level.

1.5. Bi-directional: PACAP

Evidence a: Adding PACAP at day 1 increases cell number to 115.4% of the control;

Evidence b: However, with PDGF added at day 1, applying PACAP on the next day would decrease the cell number to 67.8% of the control level.

Below are the routes selected from decision tree analysis leading to increased/decreased NSCs proliferation:

2.1. The route "PACAP at day 1→EGF at day 3" leads to increases of NSC cell number, and its mean ratio relative to control raises from 0.989 to 1.15 and 1.46, strongly promoting cell proliferation (as shown in FIG. 8D);

2.2. Alternatively, the route "Jagged at day 1→EGF at day 2→CXCL at day 4" also leads to a monotonic increase of NSC cell number till 2.44 times of the control level (as shown in FIG. 8D).

Permutation Test and Decision Tree Analysis of Combinatorial Inputs

Subjecting combinatorial inputs to permutation test and decision tree analysis, rules of single and combined ligands are obtained on NSCs differentiation and self-renewal.

Subjecting NSCs Hes5 Expression Results to Permutation Test 1.1. Among all 6 ligands, only PDGF can make significant impact alone and tends to drive NSC to self-renewal, increasing Hes5 expression by a factor of 1.06. However, such increase would be offset if combined with DLL, dropping back to 99.3% of the control level.

1.2. For the other ligands, a combination of at least two ligands are required to drive NSC to self-renewal. Such exemplar pairs are: DLL+Jagged, and EGF+Jagged, which are capable to increase the Hes5 expression by a factor of 1.08, and 1.06, respectively, suggesting that they may function synergistically.

Subjecting NSCs Hes5 Expression Results to Decision Tree Analysis 2.1. PDGF is identified to be most dominant ligand in enhancing Hes5 expression, because its presence guarantees that the mean ratio relative to control increases at least to 1.11. If the following conditions are further satisfied in an additive manner, that is 'without DLL, CXCL or EGF", this mean ratio would rise incrementally from 1.11 to 1.22, 1.37 and till 1.56 (as indicated in FIG. 18A);

2.2. Without PDGF's presence, which results in a reduction of Hes5 expression to 98.7% of the control level, it is DLL that subsequently determines NSCs' fate in the following way: if DLL is again missing, the Hes5 expression drops further to 94.3% and NSCs are approaching to differentiation (as indicated in FIG. 18B). Conversely, if DLL is present, the Hes5 expression would start to take off and the mean ratio relative to control increases to 1.03. This ratio will further increase to 1.10 if accompanied with CXCL, and even more to 1.22 if Jagged is also added (as indicated in FIG. 18B).

Subjecting NSCs Proliferation Results to Permutation Test 1.1. Among all 6 ligands, only PACAP can make significant impact alone and promotes NSCs' proliferation, increasing cell number by a factor of 1.12.

Subjecting NSCs Proliferation Results to Decision Tree Analysis 2.1. PACAP is identified to be most dominant ligand in promoting cell proliferation, because its presence guarantees that the mean ratio relative to control increases at least to 1.57. If the following conditions are further satisfied in an additive manner, that is 'without PDGF, DLL or Jagged", this mean ratio would rise incrementally from 1.57 to 1.77, 2.02 and till 2.33 (as shown in FIG. 18A);

2.2. Without PACAP's presence, Jagged can reduce the mean ratio of cell number relative to control to 1.14, and further down to 1.08 if DLL is also added, down-regulating cell proliferation (as shown in FIG. 18A).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means plus- or step-plus-function limitations, unless such a limitation is explicitly recited in a given claim using the phrase(s) "means for" or "step for," respectively.

REFERENCES

1. Klein, A. M., Mazutis, L., Akartuna, I., Tallapragada, N., Veres, A., Li, V, Peshkin, L., Weitz, D. A., and Kirschner, M. W. (2015). Droplet barcoding for single-cell transcriptomics applied to embryonic stem cells. *Cell* 161, 1187-1201.
2. Jeong, J. W., McCall, J. G., Shin, G., Zhang, Y, Al-Hasani, R., Kim, M., Li, S., Sim, J. Y., Jang, K. I., Shi, Y., et al. (2015). Wireless Optofluidic Systems for Programmable In Vivo Pharmacology and Optogenetics. *Cell* 162, 662-674.
3. Occhetta, P., Centola, M., Tonnarelli, B., Redaelli, A., Martin, I., and Rasponi, M. (2015). High-Throughput Microfluidic Platform for 3D Cultures of Mesenchymal Stem Cells, Towards Engineering Developmental Processes. *Sci. Rep.* 5, 10288.
4. Sarioglu, a F., Aceto, N., Kojic, N., Donaldson, M. C., Zeinali, M., Hamza, B., Engstrom, A., Zhu, H., Sundaresan, T. K., Miyamoto, D. T., et al. (2015). A microfluidic device for label-free, physical capture of circulating tumor cell clusters. *Nat. Methods* 12, 1-10.
5. Cao, Z., Chen, C., He, B., Tan, K., and Lu, C. (2015). A microfluidic device for epigenomic profiling using 100 cells. *Nat. Methods* 12, 959-962.
6. Kolch, W., Halasz, M., Granovskaya, M., and Kholodenko, B. N. (2015). The dynamic control of signal transduction networks in cancer cells. *Nat. Publ. Gr.* 15, 515-527.
7. Kellogg, R. A., and Tay, S. (2015). Noise facilitates transcriptional control under dynamic inputs. *Cell* 160, 381-392.
8. Judge, A. D., Sood, V, Shaw, J. R., Fang, D., McClintock, K., and MacLachlan, I. (2005). Sequence-dependent stimulation of the mammalian innate immune response by synthetic siRNA. *Nat Biotechnol* 23, 457-462.
9. Ying, Q. L., Nichols, J., Chambers, I., and Smith, A. (2003). BMP induction of Id proteins suppresses differentiation and sustains embryonic stem cell self-renewal in collaboration with STAT3. *Cell* 115, 281-292.
10. Ludwig, T. E., Levenstein, M. E., Jones, J. M., Berggren, W. T., Mitchen, E. R., Frane, J. L., Crandall, L. J., Daigh, C., Conard, K. R., Piekarczyk, M. S., et al. (2006). Derivation of human embryonic stem cells in defined conditions. *Nat. Biotechnol.* 24, 185-187.

11. Ghasemi-Dehkordi, P., Allahbakhshian-Farsani, M., Abdian, N., Mirzaeian, A., Hashemzadeh-Chaleshtori, M., and Jafari-Ghahfarokhi, H. (2015). Effects of Feeder Layers, Culture Media, Conditional Media, Growth Factors, and Passages Number on Stem Cell Optimization. Proc. Natl. *Acad. Sci. India Sect. B—Biol. Sci.* 85, 711-717.

12. Tay, S., Hughey, J. J., Lee, T. K., Lipniacki, T., Quake, S. R., and Covert, M. W. (2010). Single-cell NF-kappaB dynamics reveal digital activation and analogue information processing. *Nature* 466, 267-271.

13. Wolfe, R. P., and Ahsan, T. (2013). Shear stress during early embryonic stem cell differentiation promotes hematopoietic and endothelial phenotypes. *Biotechnol. Bioeng.* 110, 1231-1242.

14. Ohtsuka, T., Sakamoto, M., Guillemot, F., and Kageyama, R. (2001). Roles of the Basic Helix-Loop-Helix Genes Hes1 and Hes5 in Expansion of Neural Stem Cells of the Developing Brain. *J. Biol. Chem.* 276, 30467-30474.

15. Woo, S.-M., Kim, J., Han, H.-W., Chae, J.-I., Son, M.-Y, Cho, S., Chung, H.-M., Han, Y-M., and Kang, Y-K. (2009). Notch signaling is required for maintaining stem-cell features of neuroprogenitor cells derived from human embryonic stem cells. *BMC Neurosci.* 10, 97.

16. Lecault, V, VanInsberghe, M., Sekulovic, S., Knapp, D., Wohrer, S., Bowden, W., Viel, F., McLaughlin, T., Jarandehei, A., Miller, M., et al. (2011). High-throughput analysis of single hematopoietic stem cell proliferation in microfluidic cell culture arrays. *Nat. Methods* 8, 581-U93.

17. Chung, H. H., Chan, C. K., Khire, T. S., Marsh, G. a, Clark, A., Waugh, R. E., and McGrath, J. L. (2014). Highly permeable silicon membranes for shear free chemotaxis and rapid cell labeling. *Lab Chip* 14, 2456-2468.

18. Unger, M. A., Chou, H. P., Thorsen, T., Scherer, A., Quake, S. R., (2000). Monolithic Microfabricated Valves and Pumps by Multilayer Soft Lithography. *Science.* 288, 113-116.

19. https://sites.google.com/site/rafaelsmicrofluidicspage/valve-controllers/usb-based-controller 20. Lee, S. S., Sharifian, H., Ryu, H. R., Park, J. W., Jeon, N. L., and Peter, M. (2014). *Quantitative Analysis of Cell Signalling Dynamics.* 624-626.

21. Quinlan, J. R. (1986). *Induction of Decision Trees. Mach. Learn.* 1, 81-106.

22. Dorshkind, K. (2010). Not a split decision for human hematopoiesis. *Nat. Immunol.* 11, 569-570.

23. Luni, C., Giulitti, S., Serena, E., Ferrari, L., Zambon, A., Gagliano, O., Giobbe, G. G., Michielin, F., Knöbel, S., Bosio, A., et al. (2016). High-efficiency cellular reprogramming with microfluidics. *Nat. Methods* 13, 446-452.

24. Basak, O., Taylor, V. (2007). Identification of self-replicating multipotent progenitors in the embryonic nervous system by high Notch activity and Hes5 expression. *Eur J Neurosci.* 25, 1006-1022.

25. Giachino, C., Basak, O., Taylor, V (2009) Isolation and manipulation of mammalian neural stem cells in vitro. *Methods Mol Biol.* 482, 143-158.

26. Tay, S., Hughey, J. J., Lee, T. K., Lipniacki, T., Quake, S. R., and Covert, M. W. (2010). Single-cell NF-kappaB dynamics reveal digital activation and analogue information processing. *Nature* 466, 267-271.

27. Xiong, Z., Zhao, S., Mao, X., Lu, X., He, G., Yang, G., Chen, M., Ishaq, M., and Ostrikov, K. (2014). Selective neuronal differentiation of neural stem cells induced by nanosecond microplasma agitation. *Stem Cell Res.* 12, 387-399.

28. Otify, D. Y, Youssef, E., Nagy, N. B., Marei, M. K., and Youssif, M. I. (2014). Transdifferentiation of Bone Marrow Mesenchymal Stem Cells into Neural Cells via Cerebrospinal Fluid. *Biomed. Biotechnol.* 2, 66-79.

29. Mehling, M., and Tay, S. (2014). Microfluidic cell culture. *Curr. Opin. Biotechnol.* 25, 95-102.

30. Tay, S., Hughey, J. J., Lee, T. K., Lipniacki, T., Quake, S. R., and Covert, M. W. (2010). Single-cell NF-kappaB dynamics reveal digital activation and analogue information processing. *Nature* 466, 267-271.

31. Gomez-Sjoberg, R., Leyrat, A. a, Pirone, D. M., Chen, C. S., and Quake, S. R. (2007). Versatile, fully automated, microfluidic cell culture system. *Anal. Chem.* 79, 8557-8563.

32. Mohabbat, A. B., Sandborn, W. J., Loftus, E. V. J., Wiesner, R. H., and Bruining, D. H. (2012). Anti-tumour necrosis factor treatment of inflammatory bowel disease in liver transplant recipients. *Aliment. Pharmacol. Ther.* 36, 569-574.

33. Hemberger, M., Dean, W. & Reik, W. Epigenetic dynamics of stem cells and cell lineage commitment?: digging Waddington's canal. *Nat. Rev. Mol. Cell Biol.* 10, 526-537 (2009).

34. Millet, L. J., Gilette, M. U. New perspectives on neuronal development via microfluidic environments. Trends in *Neurosci* 35, 752-761 (2012).

35. Sackmann, E. K., Fulton, A. L. & Beebe, D. J. The present and future role of microfluidics in biomedical research. *Nature* 507, 181-189 (2014).

36. Millet, L. J., Stewart, M. E., Sweedler, J. V, Nuzzo, G. & Gillette, M. U. Microfluidic devices for culturing primary mammalian neurons at low densities. *Lab Chip* 7, 987-994 (2007).

37. Haas, C. A. et al. Quiescent and Active Hippocampal Neural Stem Cells with Distinct Morphologies Respond Selectively to Physiological and Pathological Stimuli and Aging. *Cell Stem Cell* 445-456 (2010). doi:10.1016/j.stem.2010.03.01.

38. Basak, O., Giachino, C., Fiorini, E., Macdonald, H. R. & Taylor, V. Neurogenic Subventricular Zone Stem/Progenitor Cells Are Notch1-Dependent in Their Active But Not Quiescent State. *J. Neurosci.* 32, 5654-5666 (2012).

39. Sykova, E. & Forostyak, S. Stem Cells in Regenerative Medicine. Laser Ther. 87-92 (2013).

40. Behnan, J., Grieg, Z., Joel, M., Ramsness, I. & Stangeland, B. Neuroepigenetics Gene knockdown of CENPA reduces sphere forming ability and stemness of glioblastoma initiating cells. Neuroepigenetics 7, 6-18 (2016).

41. ATLAS, A. B. (2017). Allen Brain Atlas—Home. BrainMap.org.

42. C. Giachino and V. Taylor, "Lineage analysis of quiescent regenerative stem cells in the adult brain by genetic labelling reveals spatially restricted neurogenic niches in the olfactory bulb. *Eur. J. Neurosci.* 30, 9 (2009).

43. L. Breiman, Classification and regression trees. Wadsworth statistics/probability series (Wadsworth International Group, Belmont, Calif., 1984), pp. x, 358 p.

44. T. Therneau, B. Atkinson, B. Ripley, rpart: Recursive Partitioning and Regression Trees. R package version 4.1-11. https://cran.r-project.org/package=rpart, (2017).

45. P. I. Good, Permutation, parametric and bootstrap tests of hypotheses. Springer series in statistics (Springer, New York, ed. 3rd, 2005), pp. xix, 315 p.

46. N. Urban and F. Guillemot, Neurogenesis in the embryonic and adult brain: same regulators, different roles, Front. Cell. *Neurosci.* 8, 1-19 (2014).

The invention claimed is:
1. A microfluidic device comprising:
a body defining a plurality of chamber units, each chamber unit comprising:
an inlet;
an outlet;
a recess defining a chamber with a length in an x direction, a width in a y direction that is perpendicular to the x direction, the chamber having a first portion and a second portion, the first portion having a first depth in a z direction which is perpendicular to each of the x direction and the y direction, and the second portion having a second depth in the z direction that is greater than the first dept;
a first port in the first portion of the chamber;
a first channel extending between the inlet and the first port;
a first valve (Valve 1) in fluid communication with the first port and configured to be selectively opened to permit fluid communication between the first port and the first channel;
a second port in the first portion of the chamber;
a second valve (Valve 2) in fluid communication with the second port and configured to be selectively opened to permit fluid communication with the second port;
a third port in the first portion of the chamber;
a third valve (Valve 3) in fluid communication with the third port and configured to be selectively opened to permit fluid communication with the third port;
a fourth port in the second portion of the chamber;
a fourth valve (Valve 4) in fluid communication with the fourth port and configured to be selectively opened to permit fluid communication with the fourth port;
a second channel sequentially connecting:
the first channel between inlet and the first valve,
the second valve such that the second channel fluidly communicates with the second port when the second valve is open,
the outlet at a point farther from the fourth port than is the fourth valve, and
the third valve such that the second channel fluidly communicates with the third port when the second valve is open;
a fifth valve (Valve 5) disposed in the second channel and configured to be selectively closed to prevent fluid communication between the second valve and the outlet;
a third channel connecting:
the first channel at the first valve such that the third channel fluidly communicates with the first port when the first valve is open, and
the second valve such that the third channel fluidly communicates with the second port when the second valve is open;
a fourth channel connecting:
the second valve such that the fourth channel fluidly communicates with the second port and the third channel when the second valve is open, and
the fourth valve such that the fourth channel fluidly communicates with the fourth port and the outlet when the fourth valve is open;
a fifth channel connecting:
the third valve such that the fifth channel fluidly communicates with the third port when the third valve is open, and
the fourth valve such that the fifth channel fluidly communicates with the outlet when the fourth valve is open;
a sixth channel connecting:
the first valve such that the sixth channel fluidly communicates with the first port when the first valve is open, and
the third valve such that the sixth channel fluidly communicates with the third port when the third valve is open;
feed channels connecting at least two reservoirs to the respective inlets of at least two of the plurality of chamber units; and
a multiplexer between the feed channels and the respective inlets and configured to vary the ratio of at least two substances flowing between the at least two reservoirs and each of the respective inlets;
a valve control system capable of independently controlling flow through each of the valves.

2. The microfluidic device of claim 1, wherein each of the valves when open permits fluid flow between all of the channels that connect with or intersect the respective valve, and is further configured to be closed to prevent fluid flow between all of the channels that connect with or intersect the respective valve.

3. The microfluidic device of claim 1, wherein the second depth is at least any one of, or between any two of 1.1, 1.2, 1.3, 1.4, 1.5, 1.6, 1.7, 1.8, 1.9, 2.0, 2.1, 2.2, 2.3, 2.4, and/or 2.5 times the first depth.

4. The microfluidic device of claim 1, wherein the valves comprise membrane valves.

5. The microfluidic device of claim 1, wherein each chamber is rectangular along x and y directions.

6. The microfluidic device of claim 1, wherein the first port of each chamber unit is disposed on an opposite side of the respective chamber from the fourth port.

7. The microfluidic device of claim 1, wherein the second port of each chamber unit is disposed on an opposite side of the first portion of the respective chamber from the third port.

8. The microfluidic device of claim 1, wherein fourth port has a depth in the z direction that is no more than the first depth of the first portion of the respective chamber.

9. The microfluidic device of claim 1, wherein the fourth port of each chamber unit has a depth in the z direction that is no more than 70%, 60%, 50%, 40%, 30%, or 20% of the first depth of the first portion of the respective chamber.

10. The microfluidic device of claim 1, where the body defines a number of chamber units that is at least as great as any one of, or between any two of: 100, 200, 300, 400, 500, 600, 700, 800, 900, 1,000, 1,250, 1,500, 2,000, 2,500, 5,000 and/or 10,000.

11. The microfluidic device of claim 1 wherein the z dimension of the second portion of each chamber is at least as great as any one of, or between any two of: 100, 200, 300, 400, 500, 600, 700, 800, 900, 1,000, 1,250, 1,500, 2,000, 2,500, 5,000, and/or 10,000 microns.

12. The microfluidic device of claim 1 wherein an x dimension of each chamber is at least as great as any one of, or between any two of: 100, 200, 300, 400, 500, 600, 700, 800, 900, 1,000, 1,250, 1,500, 2,000, 2,500, 5,000, and/or 10,000 microns.

13. The microfluidic device of claim 1 wherein a y dimension of each chamber is at least as great as any one of, or between any two of: 10, 20, 25, 30, 35, 40, 45, 50, 55, 60, 65, 70, 75, 80, 85, 90, 95, 100, 125, 150, 200, 250, and/or 500 microns.

14. The microfluidic device of claim 1 wherein the body comprises glass, silicon, and/or plastic.

15. The microfluidic device of claim 1 wherein the body comprises silicone.

16. The microfluidic device of claim 1 wherein the body comprises polydimethylsilicone.

17. The microfluidic device of claim 1, further comprising a computer configured to control the valve control system and/or the multiplexer.

18. The device of claim 1, further comprising a microscope configured to observe the contents of at least one chamber.

19. The device of claim 18, further comprising a camera configured to record an image of the contents of the at least one chamber.

20. The device of claim 19, further comprising a computer configured to analyze the image.

21. A method of loading cells into at least one chamber unit of the device of claim 1, the method comprising:
closing Valves 2, 3, and 5;
opening Valves 1 and 4; and
flowing a fluid containing cells through the at least one chamber unit via sequentially: Valve 1, the first port, the respective chamber of the at least one chamber unit, the fourth port, Valve 4, and the outlet.

22. The method of claim 21, wherein after loading the loaded at least one chamber unit contains at least one of, or between any two of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 cells.

23. The method of claim 21, wherein the cells comprise eukaryotic or prokaryotic cells.

24. The method of claim 23, wherein the cells comprise human cells or cells derived from human cells.

25. A method of dispensing a substance into at least one chamber unit of the device of claim 1, the method comprising:
closing Valves 1, 4 and 5;
opening Valves 2 and 3; and
flowing a fluid containing the substance through the at least one chamber unit via sequentially: Valve 2, the second port, the respective chamber of the at least one chamber unit, the third port, Valve 3, and the outlet.

26. The method of claim 21, further comprising:
retrieving the cells from the at least one chamber unit by:
closing Valves 2, 3, and 5;
opening Valves 1 and 4; and
flowing fluid through the at least one chamber unit via sequentially: Valve 1, the first port, the respective chamber of the at least one chamber unit, the fourth port, Valve 4, and the outlet.

* * * * *

UNITED STATES PATENT AND TRADEMARK OFFICE
CERTIFICATE OF CORRECTION

PATENT NO. : 11,912,970 B2
APPLICATION NO. : 16/614174
DATED : February 27, 2024
INVENTOR(S) : Ce Zhang and Savas Tay Page 1 of 1

It is certified that error appears in the above-identified patent and that said Letters Patent is hereby corrected as shown below:

In the Claims

In Claim 1, Column 31, Line 18, please replace "the first dept;" with --the first depth;-- therefor.

Signed and Sealed this
Seventh Day of May, 2024

Katherine Kelly Vidal
*Director of the United States Patent and Trademark Office*